United States Patent

Reitz

Patent Number: 5,229,406
Date of Patent: Jul. 20, 1993

[54] 1,3,5-TRISUBSTITUTED-1,2,4-TRIAZOLE COMPOUNDS FOR TREATMENT OF CIRCULATORY DISORDERS

[75] Inventor: David B. Reitz, Chesterfield, Mo.

[73] Assignee: G. D. Searle & Co., Chicago, Ill.

[21] Appl. No.: 840,486

[22] Filed: Feb. 24, 1992

Related U.S. Application Data

[62] Division of Ser. No. 585,833, Sep. 19, 1990, Pat. No. 5,140,036.

[51] Int. Cl.⁵ .............................. A61K 31/41
[52] U.S. Cl. ........................ 514/381; 514/383
[58] Field of Search .................. 548/325.1, 253; 514/381, 383

[56] References Cited

U.S. PATENT DOCUMENTS

| 4,816,463 | 3/1989 | Blankley et al. | 514/293 |
| 4,880,804 | 11/1989 | Carini et al. | 514/234.5 |

FOREIGN PATENT DOCUMENTS

| 621842 | 2/1963 | Belgium . |
| 806146 | 10/1972 | Belgium . |
| 7180 | 6/1978 | European Pat. Off. . |
| 283310 | 3/1987 | European Pat. Off. . |
| 253310 | 1/1988 | European Pat. Off. . |
| 323841 | 7/1989 | European Pat. Off. . |
| 160447 | 8/1983 | German Democratic Rep. . |

OTHER PUBLICATIONS

P. C. Wong et al., *J. Pharmacol. Exp. Ther.*, 247(1), 1-7 (1988).
A. T. Chiu et al., *European J. Pharmacol.*, 157, 13-21 (1988).
A. T. Chiu et al., *J. Pharmacol. Exp. Ther.*, 250 (3), 867-874 (1989).

Primary Examiner—David B. Springer
Attorney, Agent, or Firm—J. Timothy Keane; Paul D. Matukaitis

[57] ABSTRACT

A class of 1,3,5-trisubstituted-1,2,4-triazole compounds is described for use in treatment of circulatory disorders. Compounds of particular interest are angiotensin II antagonists of the formula

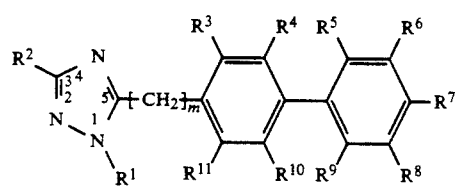

wherein m is one; wherein R¹ is selected from ethyl, n-propyl, isopropyl, butyl, isobutyl, tert-butyl, 4-methylbutyl, n-pentyl, neopentyl, benzyl, cyclohexyl, cyclohexylmethyl, 2-butenyl, 3-butenyl, 2-butynyl, 3-butynyl and 2-hydroxybutyl; wherein R² is selected from ethyl, n-propyl, isopropyl, n-butyl, sec-butyl, isobutyl, 4-methylbutyl, tert-butyl, n-pentyl, neo-pentyl, 1-oxoethyl, 1-oxopropyl, 1-oxobutyl, 1-oxopentyl, 1,1-dimethoxypropyl, 1,1-dimethoxypentyl, halo, difluoromethyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein each of R³ through R¹¹ is hydrido with the proviso that at least one of R⁵ and R⁹ must be selected from COOH, SH, PO₃H₂, SO₃H, CONHNH₂, CONHNHSO₂CF₃, OH,

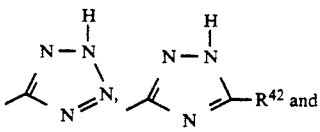

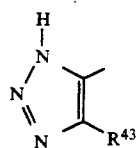

wherein each of R⁴² and R⁴³ is independently selected from chloro, cyano, nitro, trifluoromethyl, methoxycarbonyl and trifluoromethylsulfonyl. These compounds are particularly useful in treatment or control of hypertension and congestive heart failure.

5 Claims, No Drawings

1,3,5-TRISUBSTITUTED-1,2,4-TRIAZOLE COMPOUNDS FOR TREATMENT OF CIRCULATORY DISORDERS

RELATED APPLICATION

This is a divisional application of U.S. application Ser. No. 07/585,833 filed 19 Sep. 1990, now U.S. Pat. No. 5,140,036 which issued 18 Aug. 1992.

FIELD OF THE INVENTION

Non-peptidic 1,3,5-trisubstituted-1,2,4-triazole compounds are described for use in treatment of circulatory disorders such as hypertension and congestive heart failure. Of particular interest are angiotensin II antagonist compounds provided by 1,2,4-triazoles having a biphenylmethyl moiety attached to the carbon atom at the five-position of the 1,2,4-triazole.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247 (1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 1321 (1988)]. A family of 1-benzylimidazole-5-acetate derivatives has been shown to have competitive angiotensin II antagonist properties [A. T. Chiu et al, *J. Pharmacol. Exp. Ther.*, 250 (3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841 published 12 Jul. 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of known compounds having one or two oxo substituents on the triazole ring. For example, East German Patent No. 160,447 published 3 Aug. 1983 describes a family of 1,2,4-triazolin-5-one compounds, specifically 2,4-dihydro-4,5-bis(phenylmethyl)-H-1,2,4-triazol-3-one, for use as herbicides. Belgian Patent No. 806,146 published 16 Oct. 1972 describes a family of triazolinone compounds, including the compound (3-(4-m-chlorophenyl-1-piperazinyl)-propyl)-3,4-diethyl-1,2,4-triazolin-5-one, having tranquilizer, hypotensive and analgesic activities. Belgian Patent No. 631,842 published 28 Feb. 1963 describes a family of 1,2,4-triazolones having hypnotic, tranquilizer, narcotic, sedative and analgetic activities, which includes a class of 4-N-aralkyl-1,2,4-triazol-5-one compounds. EP #7,180 published 15 Jun. 1978 describes a family of 1,2-disubstituted-4-alkyl-1,2,4-triazolidine-3,5-dione compounds having a wide variety of activities, such as antiulcer, bronchodilator, antifertility and cardiovascular-related activities which include antihypertensive, antiarrhythmic, platelet aggregation inhibition and smooth muscle activities. EP #283,310 published 18 Mar. 1987 describes a family of $N^1$-diarylmethyl-$N^2$-aminoalkyl-diaza-heterocyclic derivatives for treating cerebral vascular and ischemic diseases and for protecting against anoxia.

DESCRIPTION OF THE INVENTION

A class of biphenylalkyl 1,3,5-trisubstituted-1,2,4-triazole compounds useful in treating circulatory disorders, particularly cardiovascular disorders, is defined by Formula I:

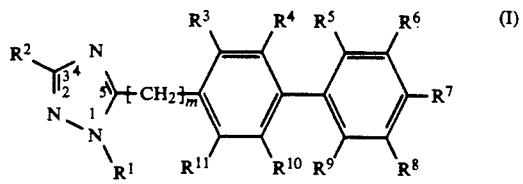

wherein m is a number selected from one to four, inclusive;

wherein $R^1$ is selected from hydrido, alkyl, hydroxyalkyl, haloalkyl, cycloalkyl, cycloalkylalkyl, formyl, aralkyl, aryl, aroyl, alkoxyalkyl, alkylcarbonyl, alkylcarbonylalkyl, alkoxycarbonyl, alkenyl, cycloalkenyl, aralkoxycarbonyl, alkynyl, alkylthiocarbonyl, alkylthiothiocarbonyl, arylthiocarbonyl, arylthiothiocarbonyl, aralkylthiocarbonyl, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amido radicals of the formula

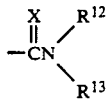

wherein X is oxygen atom or sulfur atom;

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together may form a heterocyclic group having five to seven ring members including the nitrogen atom of said amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together may form an aromatic heterocyclic group having five ring members including the nitrogen atom of said amido radical and which aromatic heterocyclic group may further contain one or more additional nitrogen atoms;

wherein each of $R^2$ through $R^{11}$ is independently selected from hydrido, alkyl, hydroxyalkyl, halo, haloalkyl, cycloalkyl, cycloalkylalkyl, cycloalkylhaloalkyl, cycloalkylcarbonyl, formyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^2$ through $R^{11}$ may be further independently selected from amino and amido radicals of the formula

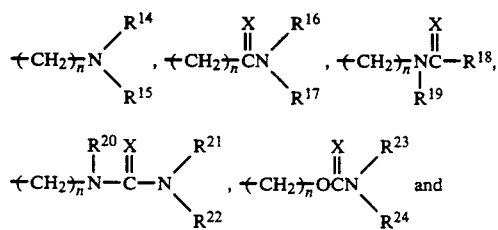

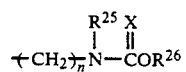

wherein X is oxygen atom or sulfur atom;

wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{14}$ and $R^{15}$ taken together, $R^{16}$ and $R^{17}$ taken together, $R^{18}$ and $R^{19}$ taken together, $R^{21}$ and $R^{22}$ taken together and $R^{23}$ and $R^{24}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{14}$ and $R^{15}$ taken together, $R^{16}$ and $R^{17}$ taken together, $R^{21}$ and $R^{22}$ taken together and $R^{23}$ and $R^{24}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

and wherein each of $R^3$ through $R^{11}$ may be further independently selected from hydroxy and acidic moieties of the formula $$-Y_nA$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{26}$, Y and A groups having a substitutable position may be substituted by one or more groups independently selected from hydroxy, alkyl, alkenyl, alkynyl, aralkyl, hydroxyalkyl, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

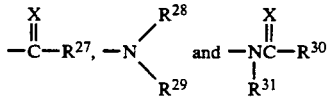

wherein X is oxygen atom or sulfur atom; wherein each of $R^{27}$ through $R^{31}$ is independently selected from hydrido, alkyl, cycloalkyl, cycloalkylalkyl, aralkyl, aryl, DR$^{32}$ and

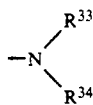

wherein D is selected from oxygen atom and sulfur atom and R$^{32}$ is selected from hydrido, alkyl, cycloalkyl, cycloalkylalkyl, aralkyl and aryl; wherein each of R$^{27}$, R$^{28}$, R$^{29}$, R$^{30}$, R$^{31}$, R$^{33}$ and R$^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of R$^{27}$, R$^{28}$, R$^{29}$, R$^{30}$, R$^{31}$R$^{33}$ and R$^{34}$ is further independently selected from amino and amido radicals of the formula

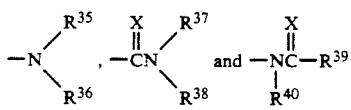

wherein X is oxygen atom or sulfur atom; wherein each of R$^{35}$, R$^{36}$, R$^{37}$, R$^{38}$, R$^{39}$ and R$^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl, and wherein each of R$^{28}$ and R$^{29}$ taken together and each of R$^{30}$ and R$^{31}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of R$^{28}$ and R$^{29}$ taken together and each of R$^{33}$ and R$^{34}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms; or a tautomer thereof or a pharmaceutically-acceptable salt thereof.

Compounds of Formula I would be useful in treating a variety of circulatory disorders, including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension.. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

The phrase "acidic group selected to contain at least one acidic hydrogen atom", as used to define the —Y$_n$A moiety, is intended to embrace chemical groups which, when attached to any of the R$^3$ through R$^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a pK$_a$ in a range from about one to about twelve. More typically, the Formula I compound would have a pK$_a$ in a range from about two to about seven. An example of an acidic group containing at least one acidic hydrogen atom is carboxyl group (—COOH). Where n is zero and A is —COOH, in the —Y$_n$A moiety, such carboxyl group would be attached directly to one of the R$^3$ through R$^{11}$ positions. The Formula I compound may have one —Y$_n$A moiety attached at one of the R$^3$ through R$^{11}$ positions, or may have a plurality of such —Y$_n$A moieties attached at more than one of the R$^3$ through R$^{11}$ positions, up to a maximum of nine such —Y$_n$A moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the —Y$_n$A moiety attached at one of positions R$^5$, R$^6$, R$^8$ and R$^9$ would be expected to have preferred properties, while attachment at R$^5$ or R$^9$ would be more preferred.

A preferred class of compounds consists of those compounds of Formula I wherein m is one; wherein R$^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylthiocarbonyl, arylthiocarbonyl, arylthiothiocarbonyl, aralkylthiocarbonyl, alkylsulfonyl, aralkylsulfonyl, arylsulfonyl, heteroaryl having one or more ring atoms selected from oxygen, sulfur and nitrogen atoms, and amido radicals of the formula

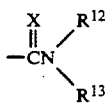

wherein X is oxygen atom or sulfur atom; wherein each of R$^{12}$ and R$^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein R$^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

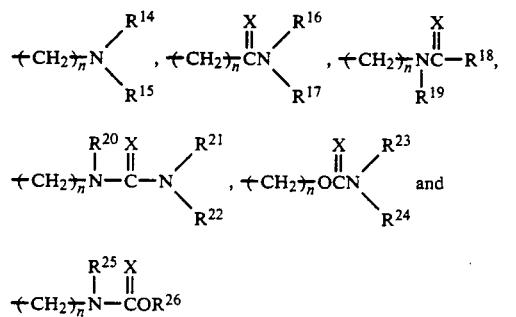

wherein X is selected from oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, arylthio, arylthiocarbonyl, arylcarbonylthio, arylthiocarbonyloxy, arylthiothiocarbonyl, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfonyl, aralkylsulfonyl and arylsulfonyl, and amino and amido radicals of the formula

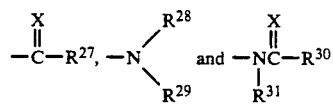

wherein X is oxygen atom or sulfur atom; wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;
and wherein each of $R^3$ through $R^{11}$ may be further independently selected from acidic moieties of the formula

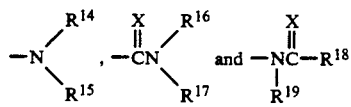

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

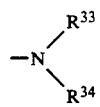

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and $$-N\begin{matrix}R^{33}\\R^{34}\end{matrix}$$

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

A more preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylsulfonyl, aralkylsulfonyl and arylsulfonyl, and amido radicals of the formula

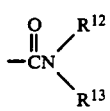

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein R² is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalklylcarbonylalkyl wherein each of said heteroaryl- and cycloheteroalkyl-containing groups has one or more hetero ring atoms selected from oxygen, sulfur and nitrogen atoms, and wherein R² may be further selected from amino and amido radicals of the formula

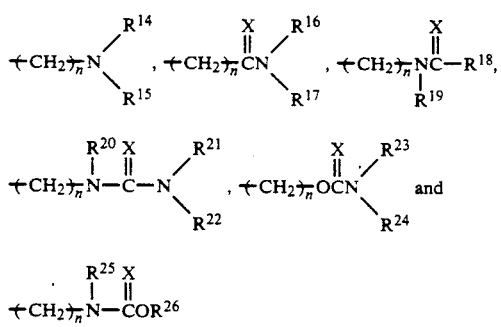

wherein X is selected from oxygen atom or sulfur atom;

wherein each n is a number independently selected from zero to six, inclusive;

wherein each of R¹⁴ through R²⁶ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of R³ through R¹¹ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amino and amido radicals of the formula

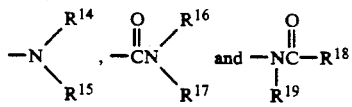

wherein each of R¹⁴, R¹⁵, R¹⁶, R¹⁷, R¹⁸ and R¹⁹ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of R³ through R¹¹ may be further independently selected from acidic moieties of the formula —Y$_n$A wherein n is a number selected from zero through three, inclusive;

wherein A is selected from carboxylic acid and bioisosteres of carboxylic acid selected from

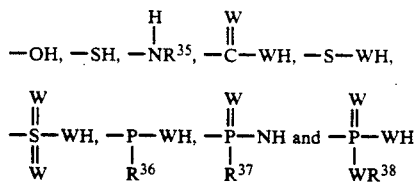

wherein each W is independently selected from oxygen atom, sulfur atom and NR³⁹; wherein each of R³⁵, R³⁶, R³⁷, R³⁸ and R³⁹ is independently selected from hydrido, alkyl, haloalkyl, haloalkylsulfonyl, haloalkylcarbonyl, cycloalkyl, cycloalkylalkyl, aryl and aralkyl; wherein each of R³⁵, R³⁶, R³⁷ and R³⁹ may be further independently selected from amino radical of the formula

wherein each of R⁴⁰ and R⁴¹ is independently selected from hydrido, alkyl, cycloalkyl, hydroxyalkyl, haloalkyl, cycloalkylalkyl, alkoxyalkyl, aralkyl and aryl, and wherein R⁴⁰ and R⁴¹ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein R⁴⁰ and R⁴¹ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of R³⁶ and R³⁷ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from R³ through R¹¹ or may be attached at any two adjacent positions selected from R³ through R¹¹ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing R¹ through R²⁶ and R³⁵ through R⁴¹, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

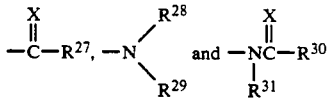

wherein X is selected from oxygen atom and sulfur atom; wherein $R^{27}$ is selected from hydrido, alkyl, cycloalkyl, cycloalkylalkyl, aralkyl, aryl and $DR^{32}$ and

wherein D is selected from oxygen atom and sulfur atom; wherein $R^{32}$ is selected from hydrido, alkyl, cycloalkyl, cycloalkylalkyl, aralkyl and aryl;
wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;
or a tautomer thereof or a pharmaceutically-acceptable salt thereof.

An even more preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, cycloalkenyl, alkynyl, mercaptocarbonyl, alkylsulfonyl, aralkylsulfonyl, arylsulfonyl and amido radicals of the formula

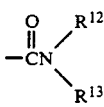

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

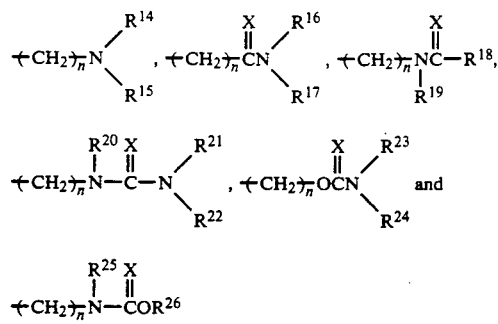

wherein X is selected from oxygen atom and sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;
and wherein each of $R^3$ through $R^{11}$ may be further independently selected from acidic moieties of the formula $$-Y_nA$$

wherein n is a number selected from zero through three, inclusive; wherein A is selected from carboxylic acid and bioisosteres of carboxylic acid selected from

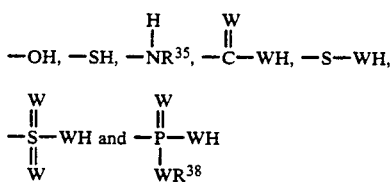

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$ and $R^{39}$ may be further independently selected from amino radical of the formula

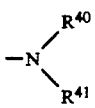

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein each of $R^1$ through $R^{26}$, $R^{35}$ and $R^{38}$ through $R^{41}$, Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

A highly preferred class of compounds within Formula I consists of those compounds wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, alkynyl, alkylsulfonyl, aralkylsulfonyl, arylsulfonyl and amido radicals of the formula

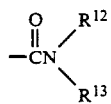

wherein each of $R^{12}$ and $R^{13}$ is independently selected from hydrido, alkyl, cycloalkyl, cyano, amino, hydroxyalkyl, alkoxyalkyl, phenalkyl and phenyl;

wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

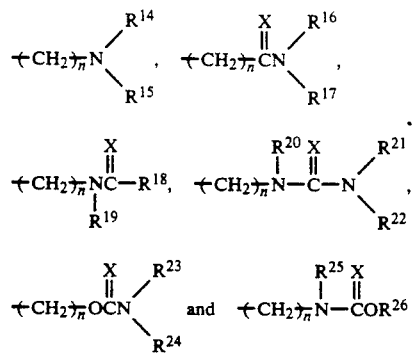

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;

and wherein each of $R^3$ through $R^{11}$ may be further independently selected from acidic moieties of the formula $$-Y_nA$$

wherein n is a number selected from zero through two, inclusive; wherein A is selected from carboxylic acid and bioisosteres of carboxylic acid selected from

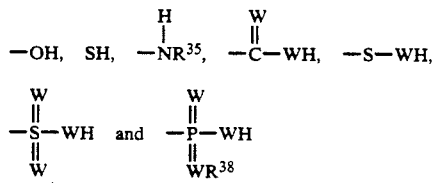

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, phenyl and benzyl; wherein each of $R^{35}$ and $R^{39}$ may be further independently selected from amino radical of the formula

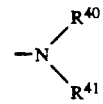

wherein each of $R^{40}$ and $R^{41}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;

wherein each of $R^1$ through $R^{26}$, $R^{35}$ and $R^{38}$ through $R^{41}$, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

An even more highly preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, benzoyl, alkoxyalkyl, alkylcarbonyl, alkoxycarbonyl, alkenyl and alkynyl;

where $R^2$ is selected from alkyl, aminoalkyl, hydroxyalkyl, halo, haloalkyl, cycloalkyl, cycloalkylalkyl, alkylcarbonyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and amino and amido radicals of the formula

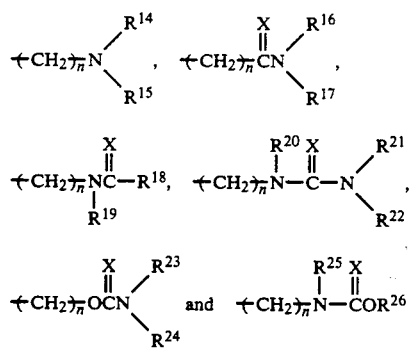

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro, carboxyl, alkylthio and mercapto;

and wherein each of $R^3$ through $R^{11}$ may be further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$,

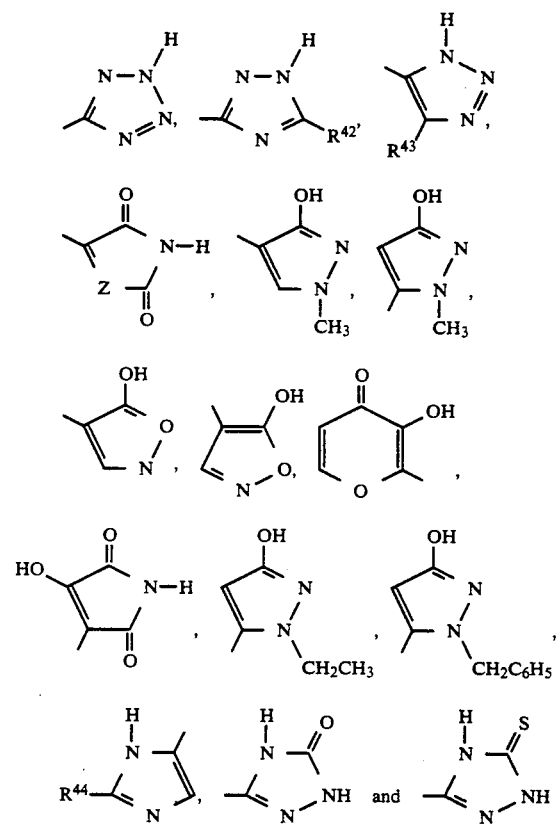

wherein each of $R^{42}$, $R^{43}$ and $R^{44}$ is independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CF_3$ and $SO_2C_6F_5$; wherein Z is selected from O, S, $NR^{45}$ and $CH_2$; wherein $R^{45}$ is selected from hydrido, $CH_3$ and $CH_2C_6H_5$; and wherein said acidic moiety may be a heterocyclic acidic group attached at any two adjacent position of $R^3$ through $R^{11}$ so as to form a fused ring system with one of the phenyl rings of the biphenyl moiety of Formula I, said biphenyl fused ring system selected from

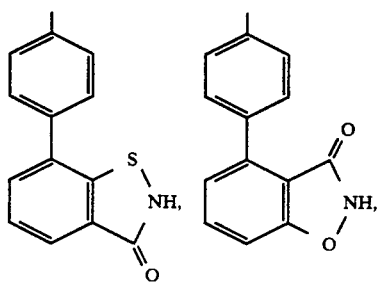

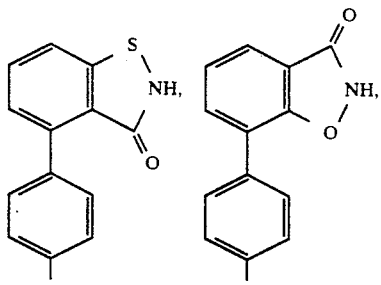

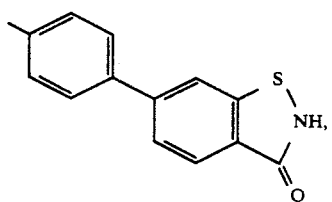

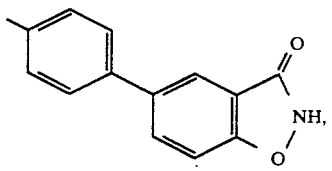

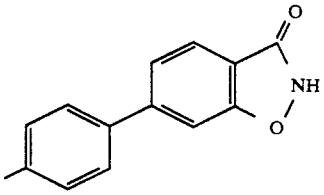

and the esters, amides and salts of said acidic moieties; or a tautomer thereof or a pharmaceutically-acceptable salt thereof.

A class of compounds of particular interest consists of those compounds of Formula I wherein m is one; wherein $R^1$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from $C_4H_9(n)$, $CH_3CH_2CH=CH$, $C_3H_7(n)$, $SC_3H_7$,

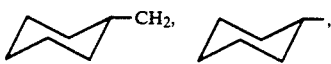

$C_2H_5$, $C_5H_{11}(n)$, $C_6H_{13}(n)$, $SC_4H_9$,

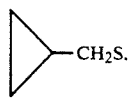

$CH_3CH=CH$, $CH_3CH_2CH_2CH=CH-$, amino, aminomethyl, aminoethyl, aminopropyl, $CH_2OH$, $CH_2OCOCH_3$, $CH_2Cl$, $Cl$, $CH_2OCH_3$, $CH_2OCH(CH_3)_2$, $I$, $CHO$, $CH_2CO_2H$, $CH(CH_3)CO_2H$, $NO_2$, $Cl$,

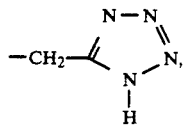

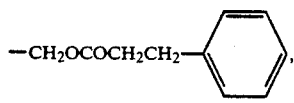

$-CO_2CH_3$, $-CONH_2$, $-CONHCH_3$, $CON(CH_3)_2$, $-CH_2-NHCO_2C_2H_5$,

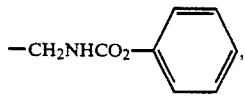

$-CH_2NHCO_2CH_3$, $-CH_2NHCO_2C_3H_7$, $-CH_2NHCO_2CH(CH_3)_2$, 13 $CH_2NHCO_2C_4H_9$, $CH_2NHCO_2$-adamantyl, $-CH_2NHCO_2$-(1-napthyl), $-CH_2NHCONHCH_3$, $-CH_2NHCONHC_2H_5$, $-CH_2NHCONHC_3H_7$, $-CH_2NHCONHC_4H_9$, $-CH_2NHCONHCH(CH_3)_2$, $-CH_2NHCONH(1-napthyl)$, $-CH_2NHCONH(1-adamantyl)$, $CO_2H$,

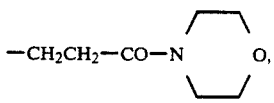

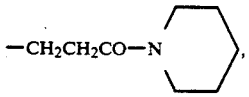

$-CH_2CH_2CH_2CO_2H$, $-CH_2CH_2F$, $-CH_2OCONHCH_3$, $-CH_2OCSNHCH_3$, $-CH_2NHCSOC_3H_7$, $-CH_2CH_2CH_2F$, $-CH_2ONO_2$,

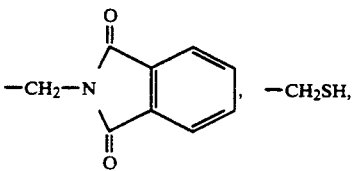

H, Cl, NO$_2$, CF$_3$, CH$_2$OH, Br, F, I, methyl, ethyl, n-propyl, isopropyl, n-butyl, sec-butyl, isobutyl, tert-butyl, n-pentyl, isopentyl, neopentyl, phenyl, cyclohexyl, cyclohexylmethyl, 1-oxoethyl, 1-oxopropyl, 1-oxobutyl, 1-oxopentyl, 1,1-dimethoxypropyl, 1,1-dimethoxypentyl, hydroxyalkyl, halo, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl and difluoromethyl; wherein each of R$^3$ through R$^{11}$ is hydrido with the proviso that at least one of R$^5$, R$^6$, R$^8$ and R$^9$ is an acidic group selected from CO$_2$H, SH, PO$_3$H$_2$, SO$_3$H, CONHNH$_2$, CONHNHSO$_2$CF$_3$, OH,

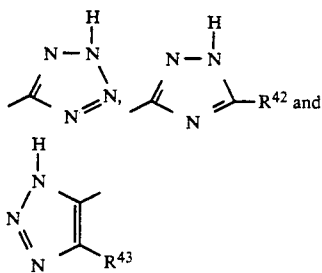

wherein each of R$^{42}$ and R$^{43}$ is independently selected from chloro, cyano, nitro, trifluoromethyl, methoxycarbonyl and trifluoromethylsulfonyl;
or a tautomer thereof or a pharmaceutically-acceptable salt thereof.

A class of compounds of more particular interest consists of those compounds of Formula I wherein m is one; wherein R$^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein R$^2$ is selected from ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein each of R$^3$ through R$^{11}$ is hydrido with the proviso that at least one of R$^5$, R$^6$, R$^8$ and R$^9$ is an acidic group selected from CO$_2$H, SH, PO$_3$H$_2$, SO$_3$H, CONHNH$_2$, CONHNHSO$_2$CF$_3$, OH,

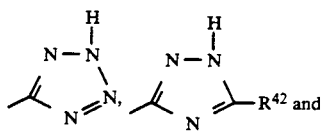

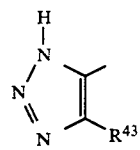

wherein each of R$^{42}$ and R$^{43}$ is independently selected from chloro, cyano, nitro, trifluoromethyl, methoxycarbonyl and trifluoromethylsulfonyl;
or a tautomer thereof or a pharmaceutically-acceptable salt thereof.

A class of compounds of even more particular interest consists of those compounds of Formula I wherein m is one; wherein R$^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3--butenyl, 2-butynyl, 3-butynyl and 2-hydroxybutyl; wherein R$^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein each of R$^3$, R$^4$, R$^6$, R$^7$, R$^8$, R$^{10}$ and R$^{11}$ is hydrido; wherein one of R$^5$ and R$^9$ is hydrido and the other of R$^5$ and R$^9$ is an acidic group selected from CO$_2$H and

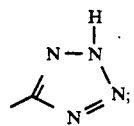

or a tautomer thereof or a pharmaceutically-acceptable salt thereof.

A family of specific compounds of particular interest within Formula I consists of compounds and pharmaceutically-acceptable salts thereof as follows:
4'-[(1-butyl-3-ethyl-1H-1,2,4-triazol-5-yl)methyl][1,1'-biphenyl]-2-carboxylic acid;
4'-[(1-butyl-3-propyl-1H-1,2,4-triazol-5-yl)methyl][1,1'-biphenyl]-2-carboxylic acid;
4'-[(1-butyl-3-isopropyl-1H-1,2,4-triazol-5-yl)methyl][1,1'-biphenyl]-2-carboxylic acid;
4'-[(1,3-dibutyl-1H-1,2,4-triazol-5-yl)methyl][1,1'-biphenyl]-2-carboxylic acid;
4'-[(1-butyl-3-secbutyl-1H-1,2,4-triazol-5-yl)methyl][1,1'-biphenyl]-2-carboxylic acid;
4'-[(1-butyl-3-isobutyl-1H-1,2,4-triazol-5-yl)methyl][1,1'-biphenyl]-2-carboxylic acid;
4'-[(1-butyl-3-tertbutyl-1H-1,2,4-triazol-5-yl)methyl][1,1'-biphenyl]-2-carboxylic acid;
4'-[(1-butyl-3-pentyl-1H-1,2,4-triazol-5-yl)methyl][1,1'-biphenyl]-2-carboxylic acid;
4'-[(1-butyl-3-isopentyl-1H-1,2,4-triazol-5-yl)methyl][1,1'-biphenyl]-2-carboxylic acid;
4'-[(1-butyl-3-mercapto-1H-1,2,4-triazol-5-yl)methyl][1,1'-biphenyl]-2-carboxylic acid;
4'-[(1-butyl-3-thiomethyl-1H-1,2,4-triazol-5-yl)methyl][1,1'-biphenyl]-2-carboxylic acid;

4'-[(1-butyl-3-thioethyl-1H-1,2,4-triazol-5-yl)methyl][1,1'-biphenyl]-2-carboxylic acid;
4'-[(1-butyl-3-thiopropyl-1H-1,2,4-triazol-5-yl)methyl[]1,1'-biphenyl]-2-carboxylic acid;
4'-[(1-butyl-3-hydroxy-1H-1,2,4-triazol-5-yl)methyl][1,1'-biphenyl]-2-carboxylic acid;
4'-[(1-butyl-3-methoxy-1H-1,2,4-triazol-5-yl)methyl][1,1'-biphenyl]-2-carboxylic acid;
4'-[(1-butyl-3-ethoxy-1H-1,2,4-triazol-5-yl)methyl][1,1'-biphenyl]-2-carboxylic acid;
4'-[(1-butyl-3-propoxy-1H-1,2,4-triazol-5-yl)methyl][1,1'-biphenyl]-2-carboxylic acid;
4'-[(1-butyl-3-butoxy-1H-1,2,4-triazol-5-yl)methyl][1,1'-biphenyl]-2-carboxylic acid;
4'-[(1-butyl-3-cyclohexyl-1H-1,2,4-triazol-5-yl)methyl][1,1'-biphenyl]-2-carboxylic acid;
4'-[(1-butyl-3-cyclohexylmethyl-1H-1,2,4-triazol-5-yl)methyl][1,1'-biphenyl]-2-carboxylic acid;
4'-[[1-butyl-3-(2-cyclohexylethyl))-1H-1,2,4-triazol-5-yl]methyl][1,1'-biphenyl]-2-carboxylic acid;
4'-[[1-(2-butyl)-3-(1,1-difluoro-2-cyclohexylethyl)-1H-1,2,4-triazol-5-yl]methyl][1,1'-biphenyl]-2-carboxylic acid;
4'-[[1-(2-butyl)-3-(1,1-difluoro-3-cyclohexylpropyl)-1H-1,2,4-triazol-5-yl]methyl][1,1'-biphenyl]-2-carboxylic acid;
4'-[(1-butyl-3-cyclohexanoyl-1,2,4,-triazol-5-yl)methyl][1,1'-biphenyl]-2-carboxylic acid;
4'-[[1-butyl-3-(1-oxo-2-cyclohexylethyl)-1H-1,2,4-triazol-5-yl]methyl][1,1'-biphenyl]-2-carboxylic acid;
4'-[(1-butyl-3-phenyl-1,2,4,-triazol-5-yl)methyl][1,1'-biphenyl]-2-carboxylic acid;
4'-[(1-butyl-3-phenylmethyl-1,2,4,-triazol-5-yl)methyl][1,1'-biphenyl]-2-carboxylic acid;
4'-[(1-butyl-1,2,4,-triazol-5-yl)methyl][1,1'-biphenyl]-2-carboxylic acid;
4'-[(3-butyl-1,2,4,-triazol-5-yl)methyl][1,1'-biphenyl]-2-carboxylic acid;
4'-[[1-butyl-3-(2-phenylethyl)-1H-1,2,4-triazol-5-yl]methyl][1,1'-biphenyl]-2-carboxylic acid;
4'-[[1-butyl-3-(1,1-difluoro-2-phenylethyl)-1H-1,2,4-triazol-5-yl]methyl][1,1'-biphenyl]-2-carboxylic acid;
4'-[[1-butyl-3-(1,1-difluoro-3-phenylpropyl)-1H-1,2,4-triazol-5-yl]methyl][1,1'-biphenyl]-2-carboxylic acid;
4'-[(1-butyl-3-benzoyl-1,2,4,-triazol-5-yl)methyl][1,1'-biphenyl]-2-carboxylic acid;
4'-[[1-butyl-3-(1-oxo-2-phenylethyl)-1H-1,2,4-triazol-5-yl]methyl][1,1'-biphenyl]-2-carboxylic acid;
4'-[[1-butyl-3-(1,1-dimethoxypropyl)-1H-1,2,4-triazol-5-yl]methyl][1,1'-biphenyl]-2-carboxylic acid;
4'-[[1-butyl-3-(1,1-dimethoxybutyl)-1H-1,2,4-triazol-5-yl]methyl][1,1'-biphenyl]-2-carboxylic acid;
4'-[[1-butyl-3-(1,1-dimethoxypentyl)-1H-1,2,4-triazol-5-yl]methyl][1,1'-biphenyl]-2-carboxylic acid;
4'-[[1-butyl-3-(1-oxopropyl)-1H-1,2,4-triazol-5-yl]methyl][1,1'-biphenyl]-2-carboxylic acid;
4'-[[1-butyl-3-(1-oxobutyl)-1H-1,2,4-triazol-5-yl]methyl][1,1'-biphenyl]-2-carboxylic acid;
4'-[[1-butyl-3-(1-oxopentyl)-1H-1,2,4-triazol-5-yl]methyl][1,1'-biphenyl]-2-carboxylic acid;
4'-[[1-butyl-3-(1,1-difluoroethyl)-1H-1,2,4-triazol-5-yl]methyl][1,1'-biphenyl]-2-carboxylic acid;
4'-[[1-butyl-3-(1,1-difluoropropyl)-1H-1,2,4-triazol-5-yl]methyl][1,1'-biphenyl]-2-carboxylic acid;
4'-[[1-butyl-3-(1,1-difluorobutyl)-1H-1,2,4-triazol-5-yl]methyl][1,1'-biphenyl]-2-carboxylic acid;
4'-[[3-butyl-1-(1,1-difluorobutyl)-1H-1,2,4-triazol-5-yl]methyl][1,1'-biphenyl]-2-carboxylic acid;
4'-[[1-butyl-3-(1,1-difluoropentyl)-1H-1,2,4-triazol-5-yl]methyl][1,1'-biphenyl]-2-carboxylic acid;
4'-[(1-propyl-3-ethyl-1H-1,2,4-triazol-5-yl)methyl][1,1'-biphenyl]-2-carboxylic acid;
4'-[(1,3-dipropyl-1H-1,2,4-triazol-5-yl)methyl][1,1'-biphenyl]-2-carboxylic acid;
4'-[(1,3-isopropyl-1H-1,2,4-triazol-5-yl)methyl][1,1'-biphenyl]-2-carboxylic acid;
4'-[(1-propyl-3-isopropyl-1H-1,2,4-triazol-5-yl)methyl][1,1'-biphenyl]-2-carboxylic acid;
4'-[(1-propyl-3-butyl-1H-1,2,4-triazol-5-yl)methyl][1,1'-biphenyl]-2-carboxylic acid;
4'-[(1-propyl-3-secbutyl-1H-1,2,4-triazol-5-yl)methyl][1,1'-biphenyl]-2-carboxylic acid;
4'-[(1-propyl-3-isobutyl-1H-1,2,4-triazol-5-yl)methyl][1,1'-biphenyl]-2-carboxylic acid;
4'-[(1-propyl-3-tertbutyl-1H-1,2,4-triazol-5-yl)methyl][1,1'-biphenyl]-2-carboxylic acid;
4'-[(1-propyl-3-pentyl-1H-1,2,4-triazol-5-yl)methyl][1,1'-biphenyl]-2-carboxylic acid;
4'-[(1-propyl-3-isopentyl-1H-1,2,4-triazol-5-yl)methyl][1,1'-biphenyl]-2-carboxylic acid;
4'-[(1-propyl-3-mercapto-1H-1,2,4-triazol-5-yl)methyl][1,1'-biphenyl]-2-carboxylic acid;
4'-[(1-propyl-3-thiomethyl-1H-1,2,4-triazol-5-yl)methyl][1,1'-biphenyl]-2-carboxylic acid;
4'-[(1-propyl-3-thioethyl-1H-1,2,4-triazol-5-yl)methyl][1,1'-biphenyl]-2-carboxylic acid;
4'-[(1-propyl-3-thiopropyl-1H-1,2,4-triazol-5-yl)methyl][1,1'-biphenyl]-2-carboxylic acid;
4'-[(1-propyl-3-hydroxy-1H-1,2,4-triazol-5-yl)methyl][1,1'-biphenyl]-2-carboxylic acid;
4'-[(1-propyl-3-methoxy-1H-1,2,4-triazol-5-yl)methyl][1,1'-biphenyl]-2-carboxylic acid;
4'-[(1-propyl-3-ethoxy-1H-1,2,4-triazol-5-yl)methyl][1,1'-biphenyl]-2-carboxylic acid;
4'-[(1-propyl-3-propoxy-1H-1,2,4-triazol-5-yl)methyl][1,1'-biphenyl]-2-carboxylic acid;
4'-[(1-propyl-3-cyclohexyl-1H-1,2,4-triazol-5-yl)methyl][1,1'-biphenyl]-2-carboxylic acid;
4'-[(1-propyl-3-cyclohexylmethyl-1H-1,2,4-triazol-5-yl)methyl][1,1'-biphenyl]-2-carboxylic acid;
1-[4'-[[1-propyl-3-(2-cyclohexylethyl)-1H-1,2,4-triazol-5-yl]methyl][1,1'-biphenyl]-2-carboxylic acid;
4'-[(1-propyl-3-cyclohexanoyl-1-H-1,2,4-triazol-5-yl)methyl][1,1'-biphenyl]-2-carboxylic acid;
1-[4'-[[1-propyl-3-(1-oxo-2-cyclohexylethyl)-1-H-1,2,4-triazol-5-yl]methyl][1,1'-biphenyl]-2-carboxylic acid;
4'-[(1-propyl-3-phenyl-1H-1,2,4-triazol-5-yl)methyl][1,1'-biphenyl]-2-carboxylic acid;
4'-[(1-propyl-3-phenylmethyl-1H-1,2,4-triazol-5-yl)methyl][1,1'-biphenyl]-2-carboxylic acid;
4'-[(1-propyl-3-phenylethyl-1H-1,2,4-triazol-5-yl)methyl][1,1'-biphenyl]-2-carboxylic acid;
4'-[(1-propyl-3-benzoyl-1H-1,2,4-triazol-5-yl)methyl][1,1'-biphenyl]-2-carboxylic acid;
4'-[[1-propyl-3-(1-oxo-2-phenylethyl)-1H-1,2,4-triazol-5-yl]methyl][1,1'-biphenyl]-2-carboxylic acid;
4'-[[1-propyl-3-(1,1-dimethoxypropyl)-1H-1,2,4-triazol-5-yl]methyl][1,1'-biphenyl]-2-carboxylic acid;
4'-[[1-propyl-3-(1,1-dimethoxybutyl)-1H-1,2,4-triazol-5-yl]methyl][1,1'-biphenyl]-2-carboxylic acid;
4'-[[1-propyl-3-(1,1-dimethoxypentyl)-1H-1,2,4-triazol-5-yl]methyl][1,1'-biphenyl]-2-carboxylic acid;
4'-[[1-propyl-3-(1-oxyopropyl)-1H-1,2,4-triazol-5-yl]methyl][1,1'-biphenyl]-2-carboxylic acid;
4'-[[1-propyl-3-(1-oxyobutyl)-1H-1,2,4-triazol-5-yl]methyl][1,1'-biphenyl]-2-carboxylic acid;

4'-[[1-propyl-3-(1-oxypentyl)-1H-1,2,4-triazol-5-yl]methyl][1,1'-biphenyl]-2-carboxylic acid;
4'-[[1-propyl-3-(1,1-difluoroethyl)-1H-1,2,4-triazol-5-yl]methyl][1,1'-biphenyl]-2-carboxylic acid;
4'-[[1-cyclohexyl-3-heptafluoropropyl-1H-1,2,4-triazol-5-yl]methyl][1,1'-biphenyl]-2-carboxylic acid;
4'-[[1-propyl-3-(1,1-difluoropropyl)-1H-1,2,4-triazol-5-yl]methyl][1,1'-biphenyl]-2-carboxylic acid;
4'-[[1-propyl-3-(1,1-difluorobutyl)-1H-1,2,4-triazol-5-yl]methyl][1,1'-biphenyl]-2-carboxylic acid;
4'-[[1-propyl-3-(1,1-difluoropentyl)-1H-1,2,4-triazol-5-yl]methyl][1,1-biphenyl]-2-carboxylic acid;
4'-[(1,3-diethyl-1H-1,2,4-triazol-5-yl)methyl][1,1'-biphenyl]-2-carboxylic acid;
4'-[(1-ethyl-3-propyl-1H-1,2,4-triazol-5-yl)methyl][1,1'-biphenyl]-2-carboxylic acid;
4'-[(1-ethyl-3-isopropyl-1H-1,2,4-triazol-5-yl)methyl][1,1'-biphenyl]-2-carboxylic acid;
4'-[(1-ethyl-3-butyl-1H-1,2,4-triazol-5-yl)methyl][1,1'-biphenyl]-2-carboxylic acid;
4'-[(1-ethyl-3-secbutyl-1H-1,2,4-triazol-5-yl)methyl][1,1'-biphenyl]-2-carboxylic acid;
4'-[(1-ethyl-3-isobutyl-1H-1,2,4-triazol-5-yl)methyl][1,1'-biphenyl]-2-carboxylic acid;
4'-[(1-ethyl-3-tertbutyl-1H-1,2,4-triazol-5-yl)methyl][1,1'-biphenyl]-2-carboxylic acid;
4'-[(1-ethyl-3-pentyl-1H-1,2,4-triazol-5-yl)methyl][1,1'-biphenyl]-2-carboxylic acid;
4'-[(1-ethyl-3-isopentyl-1H-1,2,4-triazol-5-yl)methyl][1,1'-biphenyl]-2-carboxylic acid;
4'-[(1-ethyl-3-mercapto-1H-1,2,4-triazol-5-yl)methyl][1,1'-biphenyl]-2-carboxylic acid;
4'-[(1-ethyl-3-thiomethyl-1H-1,2,4-triazol-5-yl)methyl][1,1'-biphenyl]-2-carboxylic acid;
4'-[(1-ethyl-3-thioethyl-1H-1,2,4-triazol-5-yl)methyl][1,1'-biphenyl]-2-carboxylic acid;
4'-[(1-ethyl-3-thiopropyl-1H-1,2,4-triazol-5-yl)methyl][1,1'-biphenyl]-2-carboxylic acid;
4'-[(1-ethyl-3-hydroxy-1H-1,2,4-triazol-5-yl)methyl][1,1'-biphenyl]-2-carboxylic acid;
4'-[(1-ethyl-3-methoxy-1H-1,2,4-triazol-5-yl)methyl][1,1'-biphenyl]-2-carboxylic acid;
4'-[(1-ethyl-3-ethoxy-1H-1,2,4-triazol-5-yl)methyl][1,1'-biphenyl]-2-carboxylic acid;
4'-[(1-ethyl-3-propoxy-1H-1,2,4-triazol-5-yl)methyl][1,1'-biphenyl]-2-carboxylic acid;
4'-[(1-ethyl-3-cyclohexyl-1H-1,2,4-triazol-5-yl)methyl][1,1'-biphenyl]-2-carboxylic acid;
4'-[(1-ethyl-3-cyclohexylmethyl-1H-1,2,4-triazol-5-yl)methyl][1,1'-biphenyl]-2-carboxylic acid;
4'-[[1-ethyl-3-(2-cyclohexylethyl)-1H-1,2,4-triazol-5-yl]methyl][1,1'-biphenyl]-2-carboxylic acid;
4'-[(1-ethyl-3-cyclohexanoyl-1H-1,2,4-triazol-5-yl)methyl][1,1'-biphenyl]-2-carboxylic acid;
4'-[[1-ethyl-3-(1-oxo-2-cyclohexylethyl)-1H-1,2,4-triazol-5-yl]methyl][1,1'-biphenyl]-2-carboxylic acid;
4-[(1-ethyl-3-phenyl-1H-1,2,4-triazol-5-yl)methyl][1,1'-biphenyl]-2-carboxylic acid;
4-[(1-ethyl-3-phenylmethyl-1H-1,2,4-triazol-5-yl)methyl][1,1'-biphenyl]-2-carboxylic acid;
4-[[1-ethyl-3-(2-phenylethyl)-1H-1,2,4-triazol-5-yl]methyl][1,1'-biphenyl]-2-carboxylic acid;
4-[(1-ethyl-3-benzoyl-1H-1,2,4-triazol-5-yl)methyl][1,1'-biphenyl]-2-carboxylic acid;
4-[[1-ethyl-3-(1-oxo-2-phenylethyl)-1H-1,2,4-triazol-5-yl]methyl][1,1'-biphenyl]-2-carboxylic acid;
4'-[[1-ethyl-3-(1,1-dimethoxypropyl)-1H-1,2,4-triazol-5-yl]methyl][1,1'-biphenyl]-2-carboxylic acid;
4-[[1-ethyl-3-(1,1-dimethoxybutyl)-1H-1,2,4-triazol-5-yl]methyl][1,1'-biphenyl]-2-carboxylic acid;
4'-[[1-ethyl-3-(1,1-dimethoxypentyl)-1H-1,2,4-triazol-5-yl]methyl][1,1'-biphenyl]-2-carboxylic acid;
4'-[[1-ethyl-3-(1-oxopropyl)-1H-1,2,4-triazol-5-yl]methyl][1,1'-biphenyl]-2-carboxylic acid;
4-[[1-ethyl-3-(1-oxobutyl)-1H-1,2,4-triazol-5-yl]methyl][1,1'-biphenyl]-2-carboxylic acid;
4-[[1-ethyl-3-(1-oxopentyl)-1H-1,2,4-triazol-5-yl]methyl][1,1'-biphenyl]-2-carboxylic acid;
4-[[1-ethyl-3-(1,1-difluoroethyl)-1H-1,2,4-triazol-5-yl]methyl][1,1'-biphenyl]-2-carboxylic acid;
4-[[1-ethyl-3-(1,1-difluoropropyl)-1H-1,2,4-triazol-5-yl]methyl][1,1'-biphenyl]-2-carboxylic acid;
4-[[1-ethyl-3-(1,1-difluorobutyl)-1H-1,2,4-triazol-5-yl]methyl][1,1'-biphenyl]-2-carboxylic acid;
4-[[1-ethyl-3-(1,1-difluoropentyl)-1H-1,2,4-triazol-5-yl]methyl][1,1'-biphenyl]-2-carboxylic acid;
4-[(1-secbutyl-3-ethyl-1H-1,2,4-triazol-5-yl)methyl][1,1'-biphenyl]-2-carboxylic acid;
4-[(1-secbutyl-3-propyl-1H-1,2,4-triazol-5-yl)methyl][1,1'-biphenyl]-2-carboxylic acid;
4-[(1-secbutyl-3-isopropyl-1H-1,2,4-triazol-5-yl)methyl][1,1'-biphenyl]-2-carboxylic acid;
4-[(1-secbutyl-3-butyl-1H-1,2,4-triazol-5-yl)methyl][1,1'-biphenyl]-2-carboxylic acid;
4-[(1,3-disecbutyl-1H-1,2,4-triazol-5-yl)methyl][1,1'-biphenyl]-2-carboxylic acid;
4-[(1-secbutyl-3-isobutyl-1H-1,2,4-triazol-5-yl)methyl][1,1'-biphenyl]-2-carboxylic acid;
4'-[(1-secbutyl-3-tertbutyl-1H-1,2,4-triazol-5-yl)methyl][1,1'-biphenyl]-2-carboxylic acid;
4-[(1-secbutyl-3-pentyl-1H-1,2,4-triazol-5-yl)methyl][1,1'-biphenyl]-2-carboxylic acid;
4'-[(1-secbutyl-3-isopentyl-1H-1,2,4-triazol-5-yl)methyl][1,1'-biphenyl]-2-carboxylic acid;
4-[(1-secbutyl-3-mercapto-1H-1,2,4-triazol-5-yl)methyl][1,1'-biphenyl]-2-carboxylic acid;
4'-[(1-secbutyl-3-thiomethyl-1H-1,2,4-triazol-5-yl)methyl][1,1'-biphenyl]-2-carboxylic acid;
4'-[(1-secbutyl-3-thioethyl-1H-1,2,4-triazol-5-yl)methyl][1,1'-biphenyl]-2-carboxylic acid;
4'-[(1-secbutyl-3-thiopropyl-1H-1,2,4-triazol-5-yl)methyl][1,1'-biphenyl]-2-carboxylic acid;
4'-[(1-secbutyl-3-hydroxy-1H-1,2,4-triazol-5-yl)methyl][1,1'-biphenyl]-2-carboxylic acid;
4'-[(1-secbutyl-3-methoxy-1H-1,2,4-triazol-5-yl)methyl][1,1'-biphenyl]-2-carboxylic acid;
4'-[(1-secbutyl-3-ethoxy-1H-1,2,4-triazol-5-yl)methyl][1,1'-biphenyl]-2-carboxylic acid;
4'-[(1-secbutyl-3-propoxy-1H-1,2,4-triazol-5-yl)methyl][1,1'-biphenyl]-2-carboxylic acid;
4'-[(1-secbutyl-3-cyclohexyl-1H-1,2,4-triazol-5-yl)methyl][1,1'-biphenyl]-2-carboxylic acid;
4'-[(1-secbutyl-3-cyclohexylmethyl-1H-1,2,4-triazol-5-yl)methyl][1,1'-biphenyl]-2-carboxylic acid;
4'-[[1-secbutyl-3-(2-cyclohexylethyl)-1H-1,2,4-triazol-5-yl]methyl][1,1'-biphenyl]-2-carboxylic acid;
4'-[(1-secbutyl-3-cyclohexanoyl-1H-1,2,4-triazol-5-yl)methyl][1,1'-biphenyl]-2-carboxylic acid;
4'-[[1-secbutyl-3-(1-oxo-2-cyclohexylethyl)-1H-1,2,4-triazol-5-yl]methyl][1,1'-biphenyl]-2-carboxylic acid;
4'-[(1-secbutyl-3-phenyl-1H-1,2,4-triazol-5-yl)methyl][1,1'-biphenyl]-2-carboxylic acid;
4'-[(1-secbutyl-3-phenylmethyl-1H-1,2,4-triazol-5-yl)methyl][1,1'-biphenyl]-2-carboxylic acid;
4'-[[1-secbutyl-3-(2-phenylethyl)-1H-1,2,4-triazol-5-yl]methyl][1,1'-biphenyl]-2-carboxylic acid;

4'-[(1-secbutyl-3-benzoyl-1H-1,2,4-triazol-5-yl)methyl][1,1'-biphenyl]-2-carboxylic acid;
4'-[[1-secbutyl-3-(1-oxo-2-phenylethyl)-1H-1,2,4-triazol-5-yl]methyl][1,1'-biphenyl]-2-carboxylic acid;
4'-[[1-secbutyl 1-3-(1,1-dimethoxypropyl)-1H-1,2,4-triazol-5-yl]methyl][1,1'-biphenyl]-2-carboxylic acid;
4'-[[1-secbutyl-3-(1,1-dimethoxybutyl)-1H-1,2,4-triazol-5-yl]methyl][1,1'-biphenyl]-2-carboxylic acid;
4'-[[1-secbutyl-3-(1,1-dimethoxypentyl)-1H-1,2,4-triazol-5-yl]methyl][1,1'-biphenyl]-2-carboxylic acid;
4'-[[1-secbutyl-3-(1-oxopropyl)-1H-1,2,4-triazol-5-yl]methyl][1,1'-biphenyl]-2-carboxylic acid;
4'-[[1-secbutyl-3-(1-oxobutyl)-1H-1,2,4-triazol-5-yl]methyl][1,1'-biphenyl]-2-carboxylic acid;
4'-[[1-secbutyl-3-(1-oxopentyl)-1H-1,2,4-triazol-5-yl]methyl][1,1'-biphenyl]-2-carboxylic acid;
4'-[[1-secbutyl-3-(1,1-difluoroethyl)-1H-1,2,4-triazol-5-yl]methyl][1,1'-biphenyl]-2-carboxylic acid;
4'-[[1-secbutyl-3-(1,1-difluoropropyl)-1H-1,2,4-triazol-5-yl]methyl][1,1'-biphenyl]-2-carboxylic acid;
4'-[[1-secbutyl-3-(1,1-difluorobutyl)-1H-1,2,4-triazol-5-yl]methyl][1,1'-biphenyl]-2-carboxylic acid;
4'-[[1-secbutyl-3-(1,1-difluoropentyl)-1H-1,2,4-triazol-5-yl]methyl][1,1'-biphenyl]-2-carboxylic acid;
4'-[(1-isobutyl-3-ethyl-1H-1,2,4-triazol-5-yl)methyl][1,1'-biphenyl]-2-carboxylic acid;
4'-[(1-isobutyl-3-propyl-1H-1,2,4-triazol-5-yl)methyl][1,1'-biphenyl]-2-carboxylic acid;
4'-[(1-isobutyl-3-isopropyl-1H-1,2,4-triazol-5-yl)methyl][1,1'-biphenyl]-2-carboxylic acid;
4'-[(1-isobutyl-3-butyl-1H-1,2,4-triazol-5-yl)methyl][1,1'-biphenyl]-2-carboxylic acid;
4'-[(1-isobutyl-3-secbutyl-1H-1,2,4-triazol-5-yl)methyl][1,1'-biphenyl]-2-carboxylic acid;
4'-[(1,3-diisobutyl-1H-1,2,4-triazol-5-yl)methyl][1,1'-biphenyl]-2-carboxylic acid;
4'-[(1-isobutyl-3-tertbutyl-1H-1,2,4-triazol-5-yl)methyl][1,1'-biphenyl]-2-carboxylic acid;
4'-[(1-isobutyl-3-pentyl-1H-1,2,4-triazol-5-yl)methyl][1,1'-biphenyl]-2-carboxylic acid;
4'-[(1-isobutyl-3-isopentyl-1H-1,2,4-triazol-5-yl)methyl][1,1'-biphenyl]-2-carboxylic acid;
4'-[(1-isobutyl-3-mercapto-1H-1,2,4-triazol-5-yl)methyl][1,1'-biphenyl]-2-carboxylic acid;
4'-[(1-isobutyl-3-thiomethyl-1H-1,2,4-triazol-5-yl)methyl][1,1'-biphenyl]-2-carboxylic acid;
4'-[(1-isobutyl-3-thioethyl-1H-1,2,4-triazol-5-yl)methyl][1,1'-biphenyl]-2-carboxylic acid;
4'-[(1-isobutyl-3-thiopropyl-1H-1,2,4-triazol-5-yl)methyl][1,1'-biphenyl]-2-carboxylic acid;
4'-[(1-isobutyl-3-hydroxy-1H-1,2,4-triazol-5-yl)methyl][1,1'-biphenyl]-2-carboxylic acid;
4'-[(1-isobutyl-3-methoxy-1H-1,2,4-triazol-5-yl)methyl][1,1'-biphenyl]-2-carboxylic acid;
4'-[(1-isobutyl-3-ethoxy-1H-1,2,4-triazol-5-yl)methyl][1,1'-biphenyl]-2-carboxylic acid;
4'-[(1-isobutyl-3-propoxy-1H-1,2,4-triazol-5-yl)methyl][1,1'-biphenyl]-2-carboxylic acid;
4'-[(1-isobutyl-3-cyclohexyl-1H-1,2,4-triazol-5-yl)methyl][1,1'-biphenyl]-2-carboxylic acid;
4'-[(1-isobutyl-3-cyclohexylmethyl-1H-1,2,4-triazol-5-yl)methyl][1,1'-biphenyl]-2-carboxylic acid;
4'-[[1-isobutyl-3-(2-cyclohexylethyl)-1H-1,2,4-triazol-5-yl]methyl][1,1'-biphenyl]-2-carboxylic acid;
4'-[(1-isobutyl-3-cyclohexanoyl-1H-1,2,4-triazol-5-yl)methyl][1,1'-biphenyl]-2-carboxylic acid;
4'-[[1-isobutyl-3-(1-oxo-2-cyclohexylethyl)-1H-1,2,4-triazol-5-yl]methyl][1,1'-biphenyl]-2-carboxylic acid;
4'-[(1-isobutyl-3-phenyl-1H-1,2,4-triazol-5-yl)methyl][1,1'-biphenyl]-2-carboxylic acid;
4'-[(1-isobutyl-3-phenylmethyl-1H-1,2,4-triazol-5-yl)methyl][1,1'-biphenyl]-2-carboxylic acid;
4'-[[1-isobutyl-3-(2-phenylethyl)-1H-1,2,4-triazol-5-yl]methyl][1,1'-biphenyl]-2-carboxylic acid;
4'-[(1-isobutyl-3-benzoyl-1H-1,2,4-triazol-5-yl)methyl][1,1'-biphenyl]-2-carboxylic acid;
4'-[[1-isobutyl-3-(1-oxo-2-phenylethyl)-1H-1,2,4-triazol-5-yl]methyl][1,1'-biphenyl]-2-carboxylic acid;
4'-[[1-isobutyl-3-(1,1-dimethoxypropyl)-1H-1,2,4-triazol-5-yl]methyl][1,1'-biphenyl]-2-carboxylic acid;
4'-[[1-isobutyl-3-(1,1-dimethoxybutyl)-1H-1,2,4-triazol-5-yl]methyl][1,1'-biphenyl]-2-carboxylic acid;
4'-[[1-isobutyl-3-(1,1-dimethoxypentyl)-1H-1,2,4-triazol-5-yl]methyl][1,1'-biphenyl]-2-carboxylic acid;
4'-[[1-isobutyl-3-(1-oxopropyl)-1H-1,2,4-triazol-5-yl]methyl][1,1'-biphenyl]-2-carboxylic acid;
4'-[[1-isobutyl-3-(1-oxobutyl)-1H-1,2,4-triazol-5-yl]methyl][1,1'-biphenyl]-2-carboxylic acid;
4'-[[1-isobutyl-3-(1-oxopentyl)-1H-1,2,4-triazol-5-yl]methyl][1,1'-biphenyl]-2-carboxylic acid;
4'-[[1-isobutyl-3-(1,1-difluoroethyl)-1H-1,2,4-triazol-5-yl]methyl][1,1'-biphenyl]-2-carboxylic acid;
4'-[[1-isobutyl-3-(1,1-difluoropropyl)-1H-1,2,4-triazol-5-yl]methyl][1,1'-biphenyl]-2-carboxylic acid;
4-[[1-isobutyl-3-(1,1-difluorobutyl)-1H-1,2,4-triazol-5-yl]methyl][1,1'-biphenyl]-2-carboxylic acid;
4'-[[1-isobutyl-3-(1,1-difluoropentyl)-1H-1,2,4-triazol-5-yl]methyl][1,1'-biphenyl]-2-carboxylic acid;
4'-[(1-tertbutyl-3-ethyl-1H-1,2,4-triazol-5-yl)methyl][1,1'-biphenyl]-2-carboxylic acid;
4'-[(1-tertbutyl-3-propyl-1H-1,2,4-triazol-5-yl)methyl][1,1'-biphenyl]-2-carboxylic acid;
4'-[(1-tertbutyl-3-isopropyl-1H-1,2,4-triazol-5-yl)methyl][1,1'-biphenyl]-2-carboxylic acid;
4'-[(1-tertbutyl-3-butyl-1H-1,2,4-triazol-5-yl)methyl][1,1'-biphenyl]-2-carboxylic acid;
4'-[(1-tertbutyl-3-secbutyl-1H-1,2,4-triazol-5-yl)methyl][1,1'-biphenyl]-2-carboxylic acid;
4'-[(1-tertbutyl-3-isobutyl-1H-1,2,4-triazol-5-yl)methyl][1,1'-biphenyl]-2-carboxylic acid;
4'-[(1,3-ditertbutyl-1H-1,2,4-triazol-5-yl)methyl][1,1'-biphenyl]-2-carboxylic acid;
4'-[(1-tertbutyl-3-pentyl-1H-1,2,4-triazol-5-yl)methyl][1,1'-biphenyl]-2-carboxylic acid;
4'-[(1-tertbutyl-3-isopentyl-1H-1,2,4-triazol-5-yl)methyl][1,1'-biphenyl]-2-carboxylic acid;
4'-[(1-tertbutyl-3-mercapto-1H-1,2,4-triazol-5-yl)methyl][1,1'-biphenyl]-2-carboxylic acid;
4'-[(1-tertbutyl-3-thiomethyl-1H-1,2,4-triazol-5-yl)methyl][1,1'-biphenyl]-2-carboxylic acid;
4'-[(1-tertbutyl-3-thioethyl-1H-1,2,4-triazol-5-yl)methyl][1,1'-biphenyl]-2-carboxylic acid;
4'-[(1-tertbutyl-3-thiopropyl-1H-1,2,4-triazol-5-yl)methyl][1,1'-biphenyl]-2-carboxylic acid;
4'-[(1-tertbutyl-3-hydroxy-1H-1,2,4-triazol-5-yl)methyl][1,1'-biphenyl]-2-carboxylic acid;
4'-[(1-tertbutyl-3-methoxy-1H-1,2,4-triazol-5-yl)methyl][1,1'-biphenyl]-2-carboxylic acid;
4'-[(1-tertbutyl-3-ethoxy-1H-1,2,4-triazol-5-yl)methyl][1,1'-biphenyl]-2-carboxylic acid;
4'-[(1-tertbutyl-3-propoxy-1H-1,2,4-triazol-5-yl)methyl][1,1'-biphenyl]-2-carboxylic acid;
4'-[(1-tertbutyl-3-cyclohexyl-1H-1,2,4-triazol-5-yl)methyl][1,1'-biphenyl]-2-carboxylic acid;
4'-[(1-tertbutyl-3-cyclohexylmethyl-1H-1,2,4-triazol-5-yl)methyl][1,1'-biphenyl]-2-carboxylic acid;

4'-[[1-tertbutyl-3-(2-cyclohexylethyl)-1H-1,2,4-triazol-5-yl]methyl][1,1'-biphenyl]-2-carboxylic acid;
4'-[(1-tertbutyl-3-cyclohexanoyl-1H-1,2,4-triazol-5-yl)methyl][1,1'-biphenyl]-2-carboxylic acid;
4'-[[1-tertbutyl-3-(1-oxo-2-cyclohexylethyl)-1H-1,2,4-triazol-5-yl]methyl][1,1'-biphenyl]-2-carboxylic acid;
4'-[(1-tertbutyl-3-phenyl-1H-1,2,4-triazol-5-yl)methyl][1,1'-biphenyl]-2-carboxylic acid;
4'-[(1-tertbutyl-3-phenylmethyl-1H-1,2,4-triazol-5-yl)methyl][1,1'-biphenyl]-2-carboxylic acid;
4'-[[1-tertbutyl-3-(2-phenylethyl)-1H-1,2,4-triazol-5-yl]methyl][1,1'-biphenyl]-2-carboxylic acid;
4'-[(1-tertbutyl-3-benzoyl-1H-1,2,4-triazol-5-yl)methyl][1,1'-biphenyl]-2-carboxylic acid;
4'-[[1-tertbutyl-3-(1-oxo-2-phenylethyl)-1H-1,2,4-triazol-5-yl]methyl][1,1'-biphenyl]-2-carboxylic acid;
4'-[[1-tertbutyl-3-(1,1-dimethoxypropyl)-1H-1,2,4-triazol-5-yl]methyl][1,1'-biphenyl]-2-carboxylic acid;
4'-[[1-tertbutyl-3-(1,1-dimethoxybutyl)-1H-1,2,4-triazol-5-yl]methyl][1,1'-biphenyl]-2-carboxylic acid;
4'-[[1-tertbutyl-3-(1,1-dimethoxypentyl)-1H-1,2,4-triazol-5-yl]methyl][1,1'-biphenyl]-2-carboxylic acid;
4'-[[1-tertbutyl-3-(1-oxopropyl)-1H-1,2,4-triazol-5-yl]methyl][1,1'-biphenyl]-2-carboxylic acid;
4'-[[1-tertbutyl-3-(1-oxobutyl)-1H-1,2,4-triazol-5-yl]methyl][1,1'-biphenyl]-2-carboxylic acid;
4'-[[1-tertbutyl-3-(1-oxopentyl)-1H-1,2,4-triazol-5-yl]methyl][1,1'-biphenyl]-2-carboxylic acid;
4'-[[1-tertbutyl-3-(1,1-difluoroethyl)-1H-1,2,4-triazol-5-yl]methyl][1,1'-biphenyl]-2-carboxylic acid;
4'-[[1-tertbutyl-3-(1,1-difluoropropyl)-1H-1,2,4-triazol-5-yl]methyl][1,1'-biphenyl]-2-carboxylic acid;
4'-[[1-tertbutyl-3-(1,1-difluorobutyl)-1H-1,2,4-triazol-5-yl]methyl][1,1'-biphenyl]-2-carboxylic acid;
4'-[[1-tertbutyl-3-(1,1-difluoropentyl)-1H-1,2,4-triazol-5-yl]methyl][1,1'-biphenyl]-2-carboxylic acid;
4'-[(1-pentyl-3-ethyl-1H-1,2,4-triazol-5-yl)methyl][1,1'-biphenyl]-2-carboxylic acid;
4'-[(1-pentyl-3-propyl-1H-1,2,4-triazol-5-yl)methyl][1,1'-biphenyl]-2-carboxylic acid;
4'-[(1-pentyl-3-isopropyl-1H-1,2,4-triazol-5-yl)methyl][1,1'-biphenyl]-2-carboxylic acid;
4'-[(1-pentyl-3-butyl-1H-1,2,4-triazol-5-yl)methyl][1,1'-biphenyl]-2-carboxylic acid;
4'-[(1-pentyl-3-secbutyl-1H-1,2,4-triazol-5-yl)methyl][1,1'-biphenyl]-2-carboxylic acid;
4'-[(1-pentyl-3-isobutyl-1H-1,2,4-triazol-5-yl)methyl][1,1'-biphenyl]-2-carboxylic acid;
4'-[(1-pentyl-3-tertbutyl-1H-1,2,4-triazol-5-yl)methyl][1,1'-biphenyl]-2-carboxylic acid;
4'-[(1,3-dipentyl-1H-1,2,4-triazol-5-yl)methyl][1,1'-biphenyl]-2-carboxylic acid;
4'-[(1-pentyl-3-isopentyl-1H-1,2,4-triazol-5-yl)methyl][1,1'-biphenyl]-2-carboxylic acid;
4'-[(1-pentyl-3-mercapto-1H-1,2,4-triazol-5-yl)methyl][1,1'-biphenyl]-2-carboxylic acid;
4'-[(1-pentyl-3-thiomethyl-1H-1,2,4-triazol-5-yl)methyl][1,1'-biphenyl]-2-carboxylic acid;
4'-[(1-pentyl-3-thioethyl-1H-1,2,4-triazol-5-yl)methyl][1,1'-biphenyl]-2-carboxylic acid;
4'-[(1-pentyl-3-thiopropyl-1H-1,2,4-triazol-5-yl)methyl][1,1'-biphenyl]-2-carboxylic acid;
4'-[(1-pentyl-3-hydroxy-1H-1,2,4-triazol-5-yl)methyl][1,1'-biphenyl]-2-carboxylic acid;
4'-[(1-pentyl-3-methoxy-1H-1,2,4-triazol-5-yl)methyl][1,1'-biphenyl]-2-carboxylic acid;
4'-[(1-pentyl-3-ethoxy-1H-1,2,4-triazol-5-yl)methyl][1,1'-biphenyl]-2-carboxylic acid;
4'-[(1-pentyl-3-propoxy-1H-1,2,4-triazol-5-yl)methyl][1,1'-biphenyl]-2-carboxylic acid;
4'-[(1-pentyl-3-cyclohexyl-1H-1,2,4-triazol-5-yl)methyl][1,1'-biphenyl]-2-carboxylic acid;
4'-[(1-pentyl-3-cyclohexylmethyl-1H-1,2,4-triazol-5-yl)methyl][1,1'-biphenyl]-2-carboxylic acid;
4'-[[1-pentyl-3-(2-cyclohexylethyl)-1H-1,2,4-triazol-5-yl]methyl][1,1'-biphenyl]-2-carboxylic acid;
4'-[(1-pentyl-3-cyclohexanoyl-1H-1,2,4-triazol-5-yl)methyl][1,1'-biphenyl]-2-carboxylic acid;
4'-[[1-pentyl-3-(1-oxo-2-cyclohexylethyl)-1H-1,2,4-triazol-5-yl]methyl][1,1'-biphenyl]-2-carboxylic acid;
4'-[(1-pentyl-3-phenyl-1H-1,2,4-triazol-5-yl)methyl][1,1'-biphenyl]-2-carboxylic acid;
4'-[(1-pentyl-3-phenylmethyl-1H-1,2,4-triazol-5-yl)methyl][1,1'-biphenyl]-2-carboxylic acid;
4'-[[1-pentyl-3-(2-phenylethyl)-1H-1,2,4-triazol-5-yl]methyl][1,1'-biphenyl]-2-carboxylic acid;
4'-[(1-pentyl-3-benzoyl-1H-1,2,4-triazol-5-yl)methyl][1,1'-biphenyl]-2-carboxylic acid;
4'-[[1-pentyl-3-(1-oxo-2-phenylethyl)-1H-1,2,4-triazol-5-yl]methyl][1,1'-biphenyl]-2-carboxylic acid;
4'-[[1-pentyl-3-(1,1-dimethoxypropyl)-1H-1,2,4-triazol-5-yl]methyl][1,1'-biphenyl]-2-carboxylic acid;
4'-[[1-pentyl-3-(1,1-dimethoxybutyl)-1H-1,2,4-triazol-5-yl]methyl][1,1'-biphenyl]-2-carboxylic acid;
4'-[(1-pentyl-3-(1,1-dimethoxypentyl)-1H-1,2,4-triazol-5-yl]methyl][1,1'-biphenyl]-2-carboxylic acid;
4'-[[1-pentyl-3-(1-oxopropyl)-1H-1,2,4-triazol-5-yl]methyl][1,1'-biphenyl]-2-carboxylic acid;
4'-[[1-pentyl-3-(1-oxobutyl)-1H-1,2,4-triazol-5-yl]methyl][1,1'-biphenyl]-2-carboxylic acid;
4'-[[1-pentyl-3-(1-oxopentyl)-1H-1,2,4-triazol-5-yl]methyl][1,1'-biphenyl]-2-carboxylic acid;
4'-[[1-pentyl-3-(1,1-difluoroethyl)-1H-1,2,4-triazol-5-yl]methyl][1,1'-biphenyl]-2-carboxylic acid;
4'-[[1-pentyl-3-(1,1-difluoropropyl)-1H-1,2,4-triazol-5-yl]methyl][1,1'-biphenyl]-2-carboxylic acid;
4'-[[1-pentyl-3-(1,1-difluorobutyl)-1H-1,2,4-triazol-5-yl]methyl][1,1'-biphenyl]-2-carboxylic acid;
4'-[[1-pentyl-3-(1,1-difluoropentyl)-1H-1,2,4-triazol-5-yl]methyl][1,1'-biphenyl]-2-carboxylic acid;
4'-[(1-isopentyl-3-ethyl-1H-1,2,4-triazol-5-yl)methyl][1,1'-biphenyl]-2-carboxylic acid;
4'-[(1-isopentyl-3-propyl-1H-1,2,4-triazol-5-yl)methyl][1,1'-biphenyl]-2-carboxylic acid;
4'-[(1-isopentyl-3-isopropyl-1H-1,2,4-triazol-5-yl)methyl][1,1'-biphenyl]-2-carboxylic acid;
4'-[(1-isopentyl-3-butyl-1H-1,2,4-triazol-5-yl)methyl][1,1'-biphenyl]-2-carboxylic acid;
4'-[(1-isopentyl-3-secbutyl-1H-1,2,4-triazol-5-yl)methyl][1,1'-biphenyl]-2-carboxylic acid;
4'-[(1-isopentyl-3-isobutyl-1H-1,2,4-triazol-5-yl)methyl][1,1'-biphenyl]-2-carboxylic acid;
4'-[(1-isopentyl-3-tertbutyl-1H-1,2,4-triazol-5-yl)methyl][1,1'-biphenyl]-2-carboxylic acid;
4'-[(1-isopentyl-3-pentyl-1H-1,2,4-triazol-5-yl)methyl][1,1'-biphenyl]-2-carboxylic acid;
4'-[(1,3-diisopentyl-1H-1,2,4-triazol-5-yl)methyl][1,1'-biphenyl]-2-carboxylic acid;
4'-[(1-isopentyl-3-mercapto-1H-1,2,4-triazol-5-yl)methyl][1,1'-biphenyl]-2-carboxylic acid;
4'-[(1-isopentyl-3-thiomethyl-1H-1,2,4-triazol-5-yl)methyl][1,1'-biphenyl]-2-carboxylic acid;
4'-[(1-isopentyl-3-thioethyl-1H-1,2,4-triazol-5-yl)methyl][1,1'-biphenyl]-2-carboxylic acid;
4'-[(1-isopentyl-3-thiopropyl-1H-1,2,4-triazol-5-yl)methyl][1,1'-biphenyl]-2-carboxylic acid;

4'-[(1-isopentyl-3-hydroxy-1H-1,2,4-triazol-5-yl)methyl][1,1'-biphenyl]-2-carboxylic acid;
4'-[(1-isopentyl-3-methoxy-1H-1,2,4-triazol-5-yl)methyl][1,1'-biphenyl]-2-carboxylic acid;
4'-[(1-isopentyl-3-ethoxy-1H-1,2,4-triazol-5-yl)methyl][1,1'-biphenyl]-2-carboxylic acid;
4'-[(1-isopentyl-3-propoxy-1H-1,2,4-triazol-5-yl)methyl][1,1'-biphenyl]-2-carboxylic acid;
4'-[(1-isopentyl-3-cyclohexyl-1H-1,2,4-triazol-5-yl)methyl][1,1'-biphenyl]-2-carboxylic acid;
4'-[(1-isopentyl-3-cyclohexylmethyl-1H-1,2,4-triazol-5-yl)methyl][1,1'-biphenyl]-2-carboxylic acid;
4'-[[1-pentyl-3-(2-cyclohexylethyl)-1H-1,2,4-triazol-5-yl]methyl][1,1'-biphenyl]-2-carboxylic acid;
4'-[(1-isopentyl-3-cyclohexanoyl-1H-1,2,4-triazol-5-yl)methyl][1,1'-biphenyl]-2-carboxylic acid;
4'-[[1-isopentyl-3-(1-oxo-2-cyclohexylethyl)-1H-1,2,4-triazol-5-yl]methyl][1,1'-biphenyl]-2-carboxylic acid;
4'-[(1-isopentyl-3-phenyl-1H-1,2,4-triazol-5-yl)methyl][1,1'-biphenyl]-2-carboxylic acid;
4'-[(1-isopentyl-3-phenylmethyl-1H-1,2,4-triazol-5-yl)methyl][1,1'-biphenyl]-2-carboxylic acid;
4'-[[1-isopentyl-3-(2-phenylethyl)-1H-1,2,4-triazol-5-yl]methyl][1,1'-biphenyl]-2-carboxylic acid;
4'-[(1-isopentyl-3-benzoyl-1H-1,2,4-triazol-5-yl)methyl][1,1'-biphenyl]-2-carboxylic acid;
4'-[[1-isopentyl-3-(1-oxo-2-phenylethyl)-1H-1,2,4-triazol-5-yl]methyl][1,1'-biphenyl]-2-carboxylic acid;
4'-[[1-isopentyl-3-(1,1-dimethoxypropyl)-1H-1,2,4-triazol-5-yl]methyl][1,1'-biphenyl]-2-carboxylic acid;
4'-[[1-isopentyl-3-(1,1-dimethoxybutyl)-1H-1,2,4-triazol-5-yl]methyl][1,1'-biphenyl]-2-carboxylic acid;
4'-[[1-isopentyl-3-(1,1-dimethoxypentyl)-1H-1,2,4-triazol-5-yl]methyl][1,1'-biphenyl]-2-carboxylic acid;
4'-[[1-isopentyl-3-(1-oxopropyl)-1H-1,2,4-triazol-5-yl]methyl][1,1'-biphenyl]-2-carboxylic acid;
4'-[[1-isopentyl-3-(1-oxobutyl)-1H-1,2,4-triazol-5-yl]methyl][1,1'-biphenyl]-2-carboxylic acid;
4'-[[1-isopentyl-3-(1-oxopentyl)-1H-1,2,4-triazol-5-yl]methyl][1,1'-biphenyl]-2-carboxylic acid;
4'-[[1-isopentyl-3-(1,1-difluoroethyl)-1H-1,2,4-triazol-5-yl]methyl][1,1'-biphenyl]-2-carboxylic acid;
4'-[[1-isopentyl-3-(1,1-difluoropropyl)-1H-1,2,4-triazol-5-yl]methyl][1,1'-biphenyl]-2-carboxylic acid;
4'-[[1-isopentyl-3-(1,1-difluorobutyl)-1H-1,2,4-triazol-5-yl]methyl][1,1'-biphenyl]-2-carboxylic acid;
4'-[[1-isopentyl-3-(1,1-difluoropentyl)-1H-1,2,4-triazol-5-yl]methyl][1,1'-biphenyl]-2-carboxylic acid;
4'-[[1-cyclohexyl-3-ethyl-1H-1,2,4-triazol-5-yl]methyl][1,1'-biphenyl]-2-carboxylic acid;
4'-[[1-cyclohexyl-3-propyl-1H-1,2,4-triazol-5-yl]methyl][1,1'-biphenyl]-2-carboxylic acid;
4'-[[1-cyclohexyl-3-isopropyl-1H-1,2,4-triazol-5-yl]methyl][1,1'-biphenyl]-2-carboxylic acid;
4'-[[1-cyclohexyl-3-butyl-1H-1,2,4-triazol-5-yl]methyl][1,1'-biphenyl]-2-carboxylic acid; 4'-[[1-cyclohexyl-3-secbutyl-1H-1,2,4-triazol-5-yl]methyl][1,1'-biphenyl]-2-carboxylic acid;
4'-[[1-cyclohexyl-3-isobutyl-1H-1,2,4-triazol-5-yl]methyl][1,1'-biphenyl]-2-carboxylic acid;
4'-[[1-cyclohexyl-3-tertbutyl-1H-1,2,4-triazol-5-yl]methyl][1,1'-biphenyl]-2-carboxylic acid;
4'-[[1-cyclohexyl-3-pentyl-1H-1,2,4-triazol-5-yl]methyl][1,1'-biphenyl]-2-carboxylic acid;
4'-[[1-cyclohexyl-3-isopentyl-1H-1,2,4-triazol-5-yl]methyl][1,1'-biphenyl]-2-carboxylic acid;
4'-[[1-cyclohexyl-3-mercapto-1H-1,2,4-triazol-5-yl]methyl][1,1'-biphenyl]-2-carboxylic acid;
4'-[[1-cyclohexyl-3-thiomethyl-1H-1,2,4-triazol-5-yl]methyl][1,1'-biphenyl]-2-carboxylic acid;
4'-[[1-cyclohexyl-3-thioethyl-1H-1,2,4-triazol-5-yl]methyl][1,1'-biphenyl]-2-carboxylic acid;
4'-[[1-cyclohexyl-3-thiopropyl-1H-1,2,4-triazol-5-yl]methyl][1,1'-biphenyl]-2-carboxylic acid;
4'-[[1-cyclohexyl-3-hydroxy-1H-1,2,4-triazol-5-yl]methyl][1,1'-biphenyl]-2-carboxylic acid;
4'-[[1-cyclohexyl-3-methoxy-1H-1,2,4-triazol-5-yl]methyl][1,1'-biphenyl]-2-carboxylic acid;
4'-[[1-cyclohexyl-3-ethoxy-1H-1,2,4-triazol-5-yl]methyl][1,1'-biphenyl]-2-carboxylic acid;
4'-[[1-cyclohexyl-3-propoxy-1H-1,2,4-triazol-5-yl]methyl][1,1'-biphenyl]-2-carboxylic acid;
4'-[[1-cyclohexyl-3-cyclohexyl-1H-1,2,4-triazol-5-yl]methyl][1,1'-biphenyl]-2-carboxylic acid;
4'-[[1-cyclohexyl-3-cyclohexylmethyl-1H-1,2,4-triazol-5-yl]methyl][1,1'-biphenyl]-2-carboxylic acid;
4'-[[1-cyclohexyl-3-(2-cyclohexylethyl)-1H-1,2,4-triazol-5-yl]methyl][1,1'-biphenyl]-2-carboxylic acid;
4'-[[1-cyclohexyl-3-cyclohexanoyl-1H-1,2,4-triazo-5-yl]methyl][1,1'-biphenyl]-2-carboxylic acid;
4'-[[1-cyclohexyl-3-(1-oxo-2-cyclohexylethyl)-1H-1,2,4-triazol-5-yl]methyl][1,1'-biphenyl]-2-carboxylic acid;
4'-[[1-cyclohexyl-3-phenyl-1H-1,2,4-triazol-5-yl]methyl][1,1'-biphenyl]-2-carboxylic acid;
4'-[[1-cyclohexyl-3-phenylmethyl-1H-1,2,4-triazo-5-yl]methyl][1,1'-biphenyl]-2-carboxylic acid;
4'-[[1-cyclohexyl-3-(2-phenylethyl)-1H-1,2,4-triazol-5-yl]methyl][1,1'-biphenyl]-2-carboxylic acid;
4'-[[1-cyclohexyl-3-benzoyl-1H-1,2,4-triazol-5-yl]methyl][1,1'-biphenyl]-2-carboxylic acid;
4'-[[1-cyclohexyl-3-(1-oxo-2-phenylethyl)-1H-1,2,4-triazol-5-yl]methyl][1,1'-biphenyl]-2-carboxylic acid;
4'-[[1-cyclohexyl-3-(1,1-dimethoxypropyl)-1H-1,2,4-triazol-5-yl]methyl][1,1'-biphenyl]-2-carboxylic acid;
4'-[[1-cyclohexyl-3-(1,1-dimethoxybutyl)-1H-1,2,4-triazol-5-yl]methyl][1,1'-biphenyl]-2-carboxylic acid;
4'-[[1-cyclohexyl-3-(1,1-dimethoxypentyl)-1H-1,2,4-triazol-5-yl]methyl][1,1'-biphenyl]-2-carboxylic acid;
4'-[[1-cyclohexyl-3-(1-oxopropyl)-1H-1,2,4-triazol-5-yl]methyl][1,1'-biphenyl]-2-carboxylic acid;
4'-[[1-cyclohexyl-3-(1-oxobutyl)-1H-1,2,4-triazol-5-yl]methyl][1,1'-biphenyl]-2-carboxylic acid;
4'-[[1-cyclohexyl-3-(1-oxopentyl)-1H-1,2,4-triazol-5-yl]methyl][1,1'-biphenyl]-2-carboxylic acid;
4'-[[1-cyclohexyl-3-(1,1-difluoroethyl)-1H-1,2,4-triazol-5-yl]methyl][1,1'-biphenyl]-2-carboxylic acid;
4'-[[1-cyclohexyl-3-(1,1-difluoropropyl)-1H-1,2,4-triazol-5-yl]methyl][1,1'-biphenyl]-2-carboxylic acid;
4'-[[1-cyclohexyl-3-(1,1-difluorobutyl)-1H-1,2,4-triazol-5-yl]methyl][1,1'-biphenyl]-2-carboxylic acid;
4'-[[1-cyclohexyl-3-(1,1-difluoropentyl)-1H-1,2,4-triazol-5-yl]methyl][1,1'-biphenyl]-2-carboxylic acid;
4'-[[1-(2-butenyl)-3-ethyl-1H-1,2,4-triazol-5-yl]methyl][1,1'-biphenyl]-2-carboxylic acid;
4'-[[1-(2-butenyl)-3-propyl-1H-1,2,4-triazol-5-yl]methyl][1,1'-biphenyl]-2-carboxylic acid;
4'-[[1-(2-butenyl)-3-isopropyl-1H-1,2,4-triazol-5-yl]methyl][1,1'-biphenyl]-2-carboxylic acid;
4'-[[1-(2-butenyl)-3-butyl-1H-1,2,4-triazol-5-yl]methyl][1,1'-biphenyl]-2-carboxylic acid;
4'-[[1-(2-butenyl)-3-secbutyl-1H-1,2,4-triazol-5-yl]methyl][1,1'-biphenyl]-2-carboxylic acid;
4'-[[1-(2-butenyl)-3-isobutyl-1H-1,2,4-triazol-5-yl]methyl][1,1'-biphenyl]-2-carboxylic acid;
4'-[[1-(2-butenyl)-3-tertbutyl-1H-1,2,4-triazol-5-yl]methyl][1,1'-biphenyl]-2-carboxylic acid;

4'-[[1-(2-butenyl)-3-pentyl-1H-1,2,4-triazol-5-yl]methyl][1,1'-biphenyl]-2-carboxylic acid;
4'-[[1-(2-butenyl)-3-isopentyl-1H-1,2,4-triazol-5-yl]methyl][1,1'-biphenyl]-2-carboxylic acid;
4'-[[1-(2-butenyl)-3-mercapto-1H-1,2,4-triazol-5-yl]methyl][1,1'-biphenyl]-2-carboxylic acid;
4'-[[1-(2-butenyl)-3-thiomethyl-1H-1,2,4-triazol-5-yl]methyl][1,1'-biphenyl]-2-carboxylic acid;
4'-[[1-(2-butenyl)-3-thioethyl-1H-1,2,4-triazol-5-yl]methyl][1,1'-biphenyl]-2-carboxylic acid;
4'-[[1-(2-butenyl)-3-thiopropyl-1H-1,2,4-triazol-5-yl]methyl][1,1'-biphenyl]-2-carboxylic acid;
4'-[[1-(2-butenyl)-3-hydroxy-1H-1,2,4-triazol-5-yl]methyl][1,1'-biphenyl]-2-carboxylic acid;
4'-[[1-(2-butenyl)-3-methoxy-1H-1,2,4-triazol-5-yl]methyl][1,1'-biphenyl]-2-carboxylic acid;
4'-[[1-(2-butenyl)-3-ethoxy-1H-1,2,4-triazol-5-yl]methyl][1,1'-biphenyl]-2-carboxylic acid;
4'-[[1-(2-butenyl)-3-propoxy-1H-1,2,4-triazol-5-yl]methyl][1,1'-biphenyl]-2-carboxylic acid;
4'-[[1-(2-butenyl)-3-cyclohexyl-1H-1,2,4-triazol-5-yl]methyl][1,1'-biphenyl]-2-carboxylic acid;
4'-[[1-(2-butenyl)-3-cyclohexylmethyl-1H-1,2,4-triazol-5-yl]methyl][1,1'-biphenyl]-2-carboxylic acid;
4'-[[1-(2-butenyl)-3-(2-cyclohexylethyl)-1H-1,2,4-triazol-5-yl]methyl][1,1'-biphenyl]-2-carboxylic acid;
4'-[[1-(2-butenyl)-3-cyclohexanoyl-1H-1,2,4-triazol-5-yl]methyl][1,1'-biphenyl]-2-carboxylic acid;
4'-[[1-(2-butenyl)-3-(1-oxo-2-cyclohexylethyl)-1H-1,2,4-triazol-5-yl]methyl][1,1'-biphenyl]-2-carboxylic acid;
4'-[[1-(2-butenyl)-3-phenyl-1H-1,2,4-triazol-5-yl]methyl][1,1'-biphenyl]-2-carboxylic acid;
4'-[[1-(2-butenyl)-3-phenylmethyl-1H-1,2,4-triazol-5-yl]methyl][1,1'-biphenyl]-2-carboxylic acid;
4'-[[1-(2-butenyl)-3-(2-phenylethyl)-1H-1,2,4-triazol-5-yl]methyl][1,1'-biphenyl]-2-carboxylic acid;
4'-[[1-(2-butenyl)-3-(1,1-dimethoxypropyl)-1H-1,2,4-triazol-5-yl]methyl][1,1'-biphenyl]-2-carboxylic acid;
4'-[[1-(2-butenyl)-3-(1,1-dimethoxybutyl)-1H-1,2,4-triazol-5-yl]methyl][1,1'-biphenyl]-2-carboxylic acid;
4'-[[1-(2-butenyl)-3-(1,1-dimethoxypentyl)-1H-1,2,4-triazol-5-yl]methyl][1,1'-biphenyl]-2-carboxylic acid;
4'-[[1-(2-butenyl)-3-(1-oxopropyl)-1H-1,2,4-triazol-5-yl]methyl][1,1'-biphenyl]-2-carboxylic acid;
4'-[[1-(2-butenyl)-3-(1-oxobutyl)-1H-1,2,4-triazol-5-yl]methyl][1,1'-biphenyl]-2-carboxylic acid;
4'-[[1-(2-butenyl)-3-(1-oxopentyl)-1H-1,2,4-triazol-5-yl]methyl][1,1'-biphenyl]-2-carboxylic acid;
4'-[[1-(2-butenyl)-3-(1,1-difluoroethyl)-1H-1,2,4-triazol-5-yl]methyl][1,1'-biphenyl]-2-carboxylic acid;
4'-[[1-(2-butenyl)-3-(1,1-difluoropropyl)-1H-1,2,4-triazol-5-yl]methyl][1,1'-biphenyl]-2-carboxylic acid;
4'-[[1-(2-butenyl)-3-(1,1-difluorobutyl)-1H-1,2,4-triazol-5-yl]methyl][1,1'-biphenyl]-2-carboxylic acid;
4'-[[1-(2-butenyl)-3-(1,1-difluoropentyl)-1H-1,2,4-triazol-5-yl]methyl][1,1'-biphenyl]-2-carboxylic acid;
4'-[[1-(3-butenyl)-3-ethyl-1H-1,2,4-triazol-5-yl]methyl][1,1'-biphenyl]-2-carboxylic acid;
4'-[[1-(3-butenyl)-3-propyl-1H-1,2,4-triazol-5-yl]methyl][1,1'-biphenyl]-2-carboxylic acid;
4'-[[1-(3-butenyl)-3-isopropyl-1H-1,2,4-triazol-5-yl]methyl][1,1'-biphenyl]-2-carboxylic acid;
4'-[[1-(3-butenyl)-3-butyl-1H-1,2,4-triazol-5-yl]methyl][1,1'-biphenyl]-2-carboxylic acid;
4'-[[1-(3-butenyl)-3-secbutyl-1H-1,2,4-triazol-5-yl]methyl][1,1'-biphenyl]-2-carboxylic acid;
4'-[[1-(3-butenyl)-3-isobutyl-1H-1,2,4-triazol-5-yl]methyl][1,1'-biphenyl]-2-carboxylic acid;
4'-[[1-(3-butenyl)-3-tertbutyl-1H-1,2,4-triazol-5-yl]methyl][1,1'-biphenyl]-2-carboxylic acid;
4'-[[1-(3-butenyl)-3-pentyl-1H-1,2,4-triazo-5-yl]methyl][1,1'-biphenyl]-2-carboxylic acid;
4'-[[1-(3-butenyl)-3-isopentyl-1H-1,2,4-triazol-5-yl]methyl][1,1'-biphenyl]-2-carboxylic acid;
4'-[[1-(3-butenyl)-3-mercapto-1H-1,2,4-triazol-5-yl]methyl][1,1'-biphenyl]-2-carboxylic acid;
4'-[[1-(3-butenyl)-3-thiomethyl-1H-1,2,4-triazo-5-yl]methyl][1,1'-biphenyl]-2-carboxylic acid;
4'-[[1-(3-butenyl)-3-thioethyl-1H-1,2,4-triazol-5-yl]methyl][1,1'-biphenyl]-2-carboxylic acid;
4'-[[1-(3-butenyl)-3-thiopropyl-1H-1,2,4-triazol-5-yl]methyl][1,1'-biphenyl]-2-carboxylic acid;
4'-[[1-(3-butenyl)-3-hydroxy-1H-1,2,4-triazol-5-yl]methyl][1,1'-biphenyl]-2-carboxylic acid;
4'-[[1-(3-butenyl)-3-methoxy-1H-1,2,4-triazol-5-yl]methyl][1,1'-biphenyl]-2-carboxylic acid;
4'-[[1-(3-butenyl)-3-ethoxy-1H-1,2,4-triazol-5-yl]methyl][1,1'-biphenyl]-2-carboxylic acid;
4'-[[1-(3-butenyl)-3-propoxy-1H-1,2,4-triazol-5-yl]methyl][1,1'-biphenyl]-2-carboxylic acid;
4'-[[1-(3-butenyl)-3-cyclohexyl-1H-1,2,4-triazol-5-yl]methyl][1,1'-biphenyl]-2-carboxylic acid;
4'-[[1-(3-butenyl)-3-cyclohexylmethyl-1H-1,2,4-triazol-5-yl]methyl][1,1'-biphenyl]-2-carboxylic acid;
4'-[[1-(3-butenyl)-3-(2-cyclohexylethyl)-1H-1,2,4-triazol-5-yl]methyl][1,1'-biphenyl]-2-carboxylic acid;
4'-[[1-(3-butenyl)-3-cyclohexanoyl-1H-1,2,4-triazol-5-yl]methyl][1,1'-biphenyl]-2-carboxylic acid;
4'-[[1-(3-butenyl)-3-(1-oxo-2-cyclohexylethyl)-1H-1,2,4-triazol-5-yl]methyl][1,1'-biphenyl]-2-carboxylic acid;
4'-[[1-(3-butenyl)-3-phenyl-1H-1,2,4-triazol-5-yl]methyl][1,1'-biphenyl]-2-carboxylic acid;
4'-[[1-(3-butenyl)-3-phenylmethyl-1H-1,2,4-triazol-5-yl]methyl][1,1'-biphenyl]-2-carboxylic acid;
4'-[[1-(3-butenyl)-3-(2-phenylethyl)-1H-1,2,4-triazol-5-yl]methyl][1,1'-biphenyl]-2-carboxylic acid;
4'-[[1-(3-butenyl)-3-benzoyl-1H-1,2,4-triazol-5-yl]methyl][1,1'-biphenyl]-2-carboxylic acid;
4'-[[1-(3-butenyl)-3-(1-oxo-2-phenylethyl)-1H-1,2,4-triazol-5-yl]methyl][1,1'-biphenyl]-2-carboxylic acid;
4'-[[1-(3-butenyl)-3-(1,1-dimethoxypropyl)-1H-1,2,4-triazol-5-yl]methyl][1,1'-biphenyl]-2-carboxylic acid;
4'-[[1-(3-butenyl)-3-(1,1-dimethoxybutyl)-1H-1,2,4-triazol-5-yl]methyl][1,1'-biphenyl]-2-carboxylic acid;
4'-[[1-(3-butenyl)-3-(1,1-dimethoxypentyl)-1H-1,2,4-triazol-5-yl]methyl][1,1'-biphenyl]-2-carboxylic acid;
4'-[[1-(3-(1-oxopropyl)-1H-1,2,4-triazol-5-yl]methyl][1,1,-biphenyl]-2-carboxylic acid;
4'-[[1-(3-butenyl)-3-(1-oxobutyl)-1H-1,2,4-triazol-5-yl]methyl][1,1'-biphenyl]-2-carboxylic acid;
4'-[[1-(3-butenyl)-3-(1-oxopentyl)-1H-1,2,4-triazol-5-yl]methyl][1,1'-biphenyl]-2-carboxylic acid;
4'-[[1-(3-butenyl)-3-(1,1-difluoroethyl)-1H-1,2,4-triazol-5-yl]methyl][1,1'-biphenyl]-2-carboxylic acid;
4'-[[1-(3-butenyl)-3-(1,1-difluoropropyl)-1H-1,2,4-triazol-5-yl]methyl][1,1'-biphenyl]-2-carboxylic acid;
4'-[[1-(3-butenyl)-3-(1,1-difluorobutyl)-1H-1,2,4-triazol-5-yl]methyl][1,1'-biphenyl]-2-carboxylic acid;
4'-[[1-(3-butenyl)-3-(1,1-difluoropentyl)-1H-1,2,4-triazol-5-yl]methyl][1,1'-biphenyl]-2-carboxylic acid;
4'-[[1-hexyl-3-ethyl-1H-1,2,4-triazol-5-yl]methyl][1,1'-biphenyl]-2-carboxylic acid;
4'-[[1-hexyl-3-propyl-1H-1,2,4-triazol-5-yl]methyl][1,1'-biphenyl]-2-carboxylic acid;
4'-[[1-hexyl-3-butyl-1H-1,2,4-triazol-5-yl]methyl][1,1'-biphenyl]-2-carboxylic acid;

4'-[[1-hexyl-3-secbutyl-1H-1,2,4-triazol-5-yl]methyl][1,1'-biphenyl]-2-carboxylic acid;
4'-[[1-hexyl-3-isobutyl-1H-1,2,4-triazol-5-yl]methyl][1,1'-biphenyl]-2-carboxylic acid;
4'-[[1-hexyl-3-tertbutyl-1H-1,2,4-triazol-5-yl]methyl][1,1'-biphenyl]-2-carboxylic acid;
4'-[[1-hexyl-3-pentyl-1H-1,2,4-triazol-5-yl]methyl][1,1'-biphenyl]-2-carboxylic acid;
4'-[[1-hexyl-3-isopentyl-1H-1,2,4-triazol-5-yl]methyl][1,1'-biphenyl]-2-carboxylic acid;
4'-[[1-hexyl-3-mercapto-1H-1,2,4-triazol-5-yl]methyl][1,1'-biphenyl]-2-carboxylic acid;
4'-[[1-hexyl-3-thiomethyl-1H-1,2,4-triazol-5-yl]methyl][1,1'-biphenyl]-2-carboxylic acid;
4'-[[1-hexyl-3-thioethyl-1H-1,2,4-triazol-5-yl]methyl][1,1'-biphenyl]-2-carboxylic acid;
4'-[[1-hexyl-3-thiopropyl-1H-1,2,4-triazol-5-yl]methyl][1,1'-biphenyl]-2-carboxylic acid;
4'-[[1-hexyl-3-hydroxy-1H-1,2,4-triazol-5-yl]methyl][1,1'-biphenyl]-2-carboxylic acid;
4'-[[1-hexyl-3-methoxy-1H-1,2,4-triazol-5-yl]methyl][1,1'-biphenyl]-2-carboxylic acid;
4'-[[1-hexyl-3-ethoxy-1H-1,2,4-triazol-5-yl]methyl][1,1'-biphenyl]-2-carboxylic acid;
4'-[[1-hexyl-3-propoxy-1H-1,2,4-triazol-5-yl]methyl][1,1'-biphenyl]-2-carboxylic acid;
4'-[[1-hexyl-3-cyclohexyl-1H-1,2,4-triazol-5-yl]methyl][1,1'-biphenyl]-2-carboxylic acid;
4'-[[1-hexyl-3-cyclohexylmethyl-1H-1,2,4-triazol-5-yl]methyl][1,1'-biphenyl]-2-carboxylic acid;
4'-[[1-hexyl-3-(2-cyclohexylethyl)-1H-1,2,4-triazol-5-yl]methyl][1,1'-biphenyl]-2-carboxylic acid;
4'-[[1-hexyl-3-cyclohexanoyl-1H-1,2,4-triazol-5-yl]methyl][1',1'-biphenyl]-2-carboxylic acid;
4'-[[1-hexyl-3-(1-oxo-2-cyclohexylethyl)-1H-1,2,4-triazol-5-yl]methyl][1,1'-biphenyl]-2-carboxylic acid;
4'-[[1-hexyl-3-phenyl-1H-1,2,4-triazol-5-yl]methyl][1,1'-biphenyl]-2-carboxylic acid;
4'-[[1-hexyl-3-phenylmethyl-1H-1,2,4-triazol-5-yl]methyl][1,1'-biphenyl]-2-carboxylic acid;
4'-[[1-hexyl-3-(2-phenylethyl)-1H-1,2,4-triazol-5-yl]methyl][1,1'-biphenyl]-2-carboxylic acid;
4'-[[1-hexyl-3-benzoyl-1H-1,2,4-triazol-5-yl]methyl][1,1'-biphenyl]-2-carboxylic acid;
4'-[[1-hexyl-3-(1-oxo-2-phenylethyl)-1H-1,2,4-triazol-5-yl]methyl][1,1'-biphenyl]-2-carboxylic acid;
4'-[[1-hexyl-3-(1,1-dimethoxypropyl)-1H-1,2,4-triazol-5-yl]methyl][1,1'-biphenyl]-2-carboxylic acid;
4'-[[1-hexyl-3-(1,1-dimethoxybutyl)-1H-1,2,4-triazol-5-yl]methyl][1,1'-biphenyl]-2-carboxylic acid;
4'-[[1-hexyl-3-(1,1-dimethoxypentyl)-1H-1,2,4-triazol-5-yl]methyl][1,1'-biphenyl]-2-carboxylic acid;
4'-[[1-hexyl-3-(1-oxopropyl)-1H-1,2,4-triazol-5-yl]methyl][1,1,-biphenyl]-2-carboxylic acid;
4,-[[1-hexyl-3-(1-oxobutyl)-1H-1,2,4-triazol-5-yl]methyl][1,1'-biphenyl]-2-carboxylic acid;
4'-[[1-hexyl-3-(1-oxopentyl)-1H-1,2,4-triazol-5-yl]methyl][1,1'-biphenyl]-2-carboxylic acid;
4'-[[1-hexyl-3-(1,1-difluoroethyl)-1H-1,2,4-triazol-5-yl]methyl][1,1'-biphenyl]-2-carboxylic acid;
4'-[[1-hexyl-3-(1,1-difluoropropyl)-1H-1,2,4-triazol-5-yl]methyl][1,1'-biphenyl]-2-carboxylic acid;
4'-[[1-hexyl-3-(1,1-difluorobutyl)-1H-1,2,4-triazol-5-yl]methyl][1,1'-biphenyl]-2-carboxylic acid;
4'-[[1-hexyl-3-(1,1-difluoropentyl)-1H-1,2,4-triazol-5-yl]methyl][1,1'-biphenyl]-2-carboxylic acid;
4'-[[1-(2-butynyl)-3-ethyl-1H-1,2,4-triazol-5-yl]methyl][1,1'-biphenyl]-2-carboxylic acid;
4'-[[1-(2-butynyl)-3-propyl-1H-1,2,4-triazol-5-yl]methyl][1,1'-biphenyl]-2-carboxylic acid;
4'-[[1-(2-butynyl)-3-butyl-1H-1,2,4-triazol-5-yl]methyl][1,1'-biphenyl]-2-carboxylic acid;
4'-[[1-(2-butynyl)-3-secbutyl-1H-1,2,4-triazol-5-yl]methyl][1,1'-biphenyl]-2-carboxylic acid;
4'-[[1-(2-butynyl)-3-isobutyl-1H-1,2,4-triazol-5-yl]methyl][1,1'-biphenyl]-2-carboxylic acid;
4'-[[1-(2-butynyl)-3-tertbutyl-1H-1,2,4-triazol-5-yl]methyl][1,1'-biphenyl]-2-carboxylic acid;
4'-[[1-(2-butynyl)-3-pentyl-1H-1,2,4-triazol-5-yl]methyl][1,1'-biphenyl]-2-carboxylic acid;
4'-[[1-(2-butynyl)-3-isopentyl-1H-1,2,4-triazol-5-yl]methyl][1,1'-biphenyl]-2-carboxylic acid;
4'-[[1-(2-butynyl)-3-mercapto-1H-1,2,4-triazol-5-yl]methyl][1,1'-biphenyl]-2-carboxylic acid;
4'-[[1-(2-butynyl)-3-thiomethyl-1H-1,2,4-triazol-5-yl]methyl][1,1'-biphenyl]-2-carboxylic acid;
4'-[[1-(2-butynyl)-3-thioethyl-1H-1,2,4-triazol-5-yl]methyl][1,1'-biphenyl]-2-carboxylic acid;
4'-[[1-(2-butynyl)-3-thiopropyl-1H-1,2,4-triazol-5-yl]methyl][1,1'-biphenyl]-2-carboxylic acid;
4'-[[1-(2-butynyl)-3-hydroxy-1H-1,2,4-triazol-5-yl]methyl][1,1'-biphenyl]-2-carboxylic acid;
4'-[[1-(2-butynyl)-3-methoxy-1H-1,2,4-triazol-5-yl]methyl][1,1'-biphenyl]-2-carboxylic acid;
4'-[[1-(2-butynyl)-3-ethoxy-1H-1,2,4-triazol-5-yl]methyl][1,1'-biphenyl]-2-carboxylic acid;
4'-[[1-(2-butynyl)-3-propoxy-1H-1,2,4-triazol-5-yl]methyl][1,1'-biphenyl]-2-carboxylic acid;
4'-[[1-(2-butynyl)-3-cyclohexyl-1H-1,2,4-triazol-5-yl]methyl][1,1'-biphenyl]-2-carboxylic acid;
4'-[[1-(2-butynyl)-3-cyclohexylmethyl-1H-1,2,4-triazol-5-yl]methyl][1,1'-biphenyl]-2-carboxylic acid;
4'-[[1-(2-butynyl)-3-(2-cyclohexylethyl)-1H-1,2,4-triazol-5-yl]methyl][1,1'-biphenyl]-2-carboxylic acid;
4'-[[1-(2-butynyl)-3-cyclohexanoyl-1H-1,2,4-triazol-5-yl]methyl][1,1'-biphenyl]-2-carboxylic acid;
4'-[[1-(2-butynyl)-3-(1-oxo-2-cyclohexylethyl)-1H-1,2,4-triazol-5-yl]methyl][1,1'-biphenyl]-2-carboxylic acid;
4'-[[1-(2-butynyl)-3-phenyl-1H-1,2,4-triazol-5-yl]methyl][1,1'-biphenyl]-2-carboxylic acid;
4'-[[1-(2-butynyl)-3-phenylmethyl-1H-1,2,4-triazol-5-yl]methyl][1,1'-biphenyl]-2-carboxylic acid;
4'-[[1-(2-butynyl)-3-(2-phenylethyl)-1H-1,2,4-triazol-5-yl]methyl][1,1'-biphenyl]-2-carboxylic acid;
4'-[[1-(2-butynyl)-3-benzoyl-1H-1,2,4-triazol-5-yl]methyl][1,1'-biphenyl]-2-carboxylic acid;
4'-[[1-(2-butynyl)-3-(1-oxo-2-phenylethyl)-1H-1,2,4-triazol-5-yl]methyl][1,1'-biphenyl]-2-carboxylic acid;
4'-[[1-(2-butynyl)-3-(1,1-dimethoxypropyl)-1H-1,2,4-triazol-5-yl]methyl][1,1'-biphenyl]-2-carboxylic acid;
4'-[[1-(2-butynyl)-3-(1,1-dimethoxybutyl)-1H-1,2,4-triazol-5-yl]methyl][1,1'-biphenyl]-2-carboxylic acid;
4'-[[1-(2-butynyl)-3-(1,1-dimethoxypentyl)-1H-1,2,4-triazol-5-yl]methyl][1,1'-biphenyl]-2-carboxylic acid;
4'-[[1-(2-butynyl)-3-(1-oxopropyl)-1H-1,2,4-triazol-5-yl]methyl][1,1,-biphenyl]-2-carboxylic acid;
4'-[[1-(2-butynyl)-3-(1-oxobutyl)-1H-1,2,4-triazol-5-yl]methyl][1,1'-biphenyl]-2-carboxylic acid;
4'-[[1-(2-butynyl)-3-(1-oxopentyl)-1H-1,2,4-triazol-5-yl]methyl][1,1'-biphenyl]-2-carboxylic acid;
4'-[[1-(2-butynyl)-3-(1,1-difluoroethyl)-1H-1,2,4-triazol-5-yl]methyl][1,1'-biphenyl]-2-carboxylic acid;
4'-[[1-(2-butynyl)-3-(1,1-difluoropropyl)-1H-1,2,4-triazol-5-yl]methyl][1,1'-biphenyl]-2-carboxylic acid;

4'-[[1-(2-butynyl)-3-(1,1-difluorobutyl)-1H-1,2,4-triazol-5-yl]methyl][1,1'-biphenyl]-2-carboxylic acid;
4'-[[1-(2-butynyl)-3-(1,1-difluoropentyl)-1H-1,2,4-triazol-5-yl]methyl][1,1'-biphenyl]-2-carboxylic acid;
4'-[[1-(3-butynyl)-3-ethyl-1H-1,2,4-triazol-5-yl]methyl][1,1'-biphenyl]-2-carboxylic acid;
4'-[[1-(3-butynyl)-3-propyl-1H-1,2,4-triazol-5-yl]methyl][1,1'-biphenyl]-2-carboxylic acid;
4'-[[1-(3-butynyl)-3-isopropyl-1H-1,2,4-triazol-5-yl]methyl][1,1'-biphenyl]-2-carboxylic acid;
4'-[[1-(3-butynyl)-3-butyl-1H-1,2,4-triazol-5-yl]methyl][1,1'-biphenyl]-2-carboxylic acid;
4'-[[1-(3-butynyl)-3-secbutyl-1H-1,2,4-triazol-5-yl]methyl][1,1'-biphenyl]-2-carboxylic acid;
4'-[[1-(3-butynyl)-3-isobutyl-1H-1,2,4-triazol-5-yl]methyl][1,1'-biphenyl]-2-carboxylic acid;
4'-[[1-(3-butynyl)-3-tertbutyl-1H-1,2,4-triazol-5-yl]methyl][1,1'-biphenyl]-2-carboxylic acid;
4'-[[1-(3-butynyl)-3-isopentyl-1H-1,2,4-triazol-5-yl]methyl][1,1'-biphenyl]-2-carboxylic acid;
4'-[[1-(3-butynyl)-3-pentyl-1H-1,2,4-triazol-5-yl]methyl][1,1'-biphenyl]-2-carboxylic acid;
4'-[[1-(3-butynyl)-3-mercapto-1H-1,2,4-triazol-5-yl]methyl][1,1'-biphenyl]-2-carboxylic acid;
4'-[[1-(3-butynyl)-3-thiomethyl-1H-1,2,4-triazol-5-yl]methyl][1,1'-biphenyl]-2-carboxylic acid;
4'-[[1-(3-butynyl)-3-thioethyl-1H-1,2,4-triazol-5-yl]methyl][1,1'-biphenyl]-2-carboxylic acid;
4'-[[1-(3-butynyl)-3-thiopropyl-1H-1,2,4-triazol-5-yl]methyl][1,1'-biphenyl]-2-carboxylic acid;
4'-[[1-(3-butynyl)-3-hydroxy-1H-1,2,4-triazol-5-yl]methyl][1,1'-biphenyl]-2-carboxylic acid;
4'-[[1-(3-butynyl)-3-methoxy-1H-1,2,4-triazol-5-yl]methyl][1,1'-biphenyl]-2-carboxylic acid;
4'-[[1-(3-butynyl)-3-ethoxy-1H-1,2,4-triazol-5-yl]methyl][1,1'-biphenyl]-2-carboxylic acid;
4'-[[1-(3-butynyl)-3-propoxy-1H-1,2,4-triazol-5-yl]methyl][1,1'-biphenyl]-2-carboxylic acid;
4'-[[1-(3-butynyl)-3-cyclohexyl-1H-1,2,4-triazol-5-yl]methyl][1,1'-biphenyl]-2-carboxylic acid;
4'-[[1-(3-butynyl)-3-cyclohexylmethyl-1H-1,2,4-triazol-5-yl]methyl][1,1'-biphenyl]-2-carboxylic acid;
4'-[[1-(3-butynyl)-3-(2-cyclohexylethyl)-1H-1,2,4-triazol-5-yl]methyl][1,1'-biphenyl]-2-carboxylic acid;
4'-[[1-(3-butynyl)-3-cyclohexanoyl-1H-1,2,4-triazol-5-yl]methyl][1,1'-biphenyl]-2-carboxylic acid;
4'-[[1-(3-butynyl)-3-(1-oxo-2-cyclohexylethyl)-1H-1,2,4-triazol-5-yl]methyl][1,1'-biphenyl]-2-carboxylic acid;
4'-[[1-(3-butynyl)-3-phenyl-1H-1,2,4-triazol-5-yl]methyl][1,1'-biphenyl]-2-carboxylic acid;
4'-[[1-(3-butynyl)-3-phenylmethyl-1H-1,2,4-triazol-5-yl]methyl][1,1'-biphenyl]-2-carboxylic acid;
4'-[[1-(3-butynyl)-3-(2-phenylethyl)-1H-1,2,4-triazol-5-yl]methyl][1,1'-biphenyl]-2-carboxylic acid;
4'-[[1-(3-butynyl)-3-benzoyl-1H-1,2,4-triazol-5-yl]methyl][1,1'-biphenyl]-2-carboxylic acid;
4'-[[1-(3-butynyl)-3-(1-oxo-2-phenylethyl)-1H-1,2,4-triazol-5-yl]methyl][1,1'-biphenyl]-2-carboxylic acid;
4'-[[1-(3-butynyl)-3-(1,1-dimethoxypropyl)-1H-1,2,4-triazol-5-yl]methyl][1,1'-biphenyl]-2-carboxylic acid;
4'-[[1-(3-butynyl)-3-(1,1-dimethoxybutyl)-1H-1,2,4-triazol-5-yl]methyl][1,1'-biphenyl]-2-carboxylic acid;
4'-[[1-(3-butynyl)-3-(1,1-dimethoxypentyl)-1H-1,2,4-triazol-5-yl]methyl][1,1'-biphenyl]-2-carboxylic acid;
4'-[[1-(3-butynyl)-3-(1-oxopropyl)-1H-1,2,4-triazol-5-yl]methyl][1,1'-biphenyl]-2-carboxylic acid;
4'-[[1-(3-butynyl)-3-(1-oxobutyl)-1H-1,2,4-triazol-5-yl]methyl][1,1'-biphenyl]-2-carboxylic acid;
4'-[[1-(3-butynyl)-3-(1-oxopentyl)-1H-1,2,4-triazol-5-yl]methyl][1,1'-biphenyl]-2-carboxylic acid;
4'-[[1-(3-butynyl)-3-(1,1-difluoroethyl)-1H-1,2,4-triazol-5-yl]methyl][1,1'-biphenyl]-2-carboxylic acid;
4'-[[1-(3-butynyl)-3-(1,1-difluoropropyl)-1H-1,2,4-triazol-5-yl]methyl][1,1'-biphenyl]-2-carboxylic acid;
4'-[[1-(3-butynyl)-3-(1,1-difluorobutyl)-1H-1,2,4-triazol-5-yl]methyl][1,1'-biphenyl]-2-carboxylic acid;
4'-[[1-(3-butynyl)-3-(1,1-difluoropentyl)-1H-1,2,4-triazol-5-yl]methyl][1,1'-biphenyl]-2-carboxylic acid;
4'-[(1-cyclohexyl-3-ethoxy-1H-1,2,4-triazol-5-yl)methyl][1,1'-biphenyl]-2-carboxylic acid;
4'-[(1-cyclohexyl-3-propoxy-1H-1,2,4-triazol-5-yl)methyl][1,1'-biphenyl]-2-carboxylic acid;
4'-[(1-cyclohexyl-3-isopropyl-1H-1,2,4-triazol-5-yl)methyl][1,1'-biphenyl]-2-carboxylic acid;
4'-[(1-cyclohexyl-3-butoxy-1H-1,2,4-triazol-5-yl)methyl][1,1'-biphenyl]-2-carboxylic acid;
4'-[(1-cyclohexyl-3-thiomethyl-1H-1,2,4-triazol-5-yl)methyl][1,1'-biphenyl]-2-carboxylic acid;
4'-[(1-cyclohexyl-3-thioethyl-1H-1,2,4-triazol-5-yl)methyl][1,1'-biphenyl]-2-carboxylic acid;
4'-[(1-cyclohexyl-3-thiopropyl-1H-1,2,4-triazol-5-yl)methyl][1,1'-biphenyl]-2-carboxylic acid;
4'-[(1-cyclohexyl-3-thioisopropyl-1H-1,2,4-triazol-5-yl)methyl][1,1'-biphenyl]-2-carboxylic acid;
4'-[[1-cyclohexyl-3-(1-butenyl)-1H-1,2,4-triazol-5-yl]methyl][1,1'-biphenyl]-2-carboxylic acid;
4'-[[1,3-di(2-butenyl)-1H-1,2,4-triazol-5-yl]methyl][1,1'-biphenyl]-2-carboxylic acid;
4'-[[1,3-di(3-butenyl)-1H-1,2,4-triazol-5-yl]methyl][1,1'-biphenyl]-2-carboxylic acid;
4'-[[1,3-dihexyl-1H-1,2,4-triazol-5-yl]methyl][1,1'-biphenyl]-2-carboxylic acid;
4'-[[1,3-di(2-butynyl)-1H-1,2,4-triazol-5-yl]methyl][1,1'-biphenyl]-2-carboxylic acid;
4'-[[1,3-di(3-butynyl)-1H-1,2,4-triazol-5-yl]methyl][1,1'-biphenyl]-2-carboxylic acid;
5-[4'-[(1-butyl-3-ethyl-1H-1,2,4-triazol-5-yl)methyl][1,1'-biphenyl]-2-yl]-1H-tetrazole;
5-[4'-[(1-butyl-3-propyl-1H-1,2,4-triazol-5-yl)methyl][1,1'-biphenyl]-2-yl]-1H-tetrazole;
5-[4'-[(1-butyl-3-isopropyl-1H-1,2,4-triazol-5-yl)methyl][1,1'-biphenyl]-2-yl]-1H-tetrazole;
5-[4'-[(1,3-dibutyl-1H-1,2,4-triazol-5-yl)methyl][1,1'-biphenyl]-2-yl]-1H-tetrazole;
5-[4'-[(1-butyl-3-secbutyl-1H-1,2,4-triazol-5-yl)methyl][1,1'-biphenyl]-2-yl]-1H-tetrazole;
5-[4'-[(1-butyl-3-isobutyl-1H-1,2,4-triazol-5-yl)methyl][1,1'-biphenyl]-2-yl]-1H-tetrazole;
5-[4'-[(1-butyl-3-tertbutyl-1H-1,2,4-triazol-5-yl)methyl][1,1'-biphenyl]-2-yl]-1H-tetrazole;
5-[4'-[(1-butyl-3-pentyl-1H-1,2,4-triazol-5-yl)methyl][1,1'-biphenyl]-2-yl]-1H-tetrazole;
5-[4'-[(1-butyl-1H-1,2,4-triazol-5-yl)methyl][1,1'-biphenyl]-2-yl]-1H-tetrazole;
5-[4'-[(3-butyl-1H-1,2,4-triazol-5-yl)methyl][1,1'-biphenyl]-2-yl]-1H-tetrazole;
5-[4'-[(1-butyl-3-isopentyl-1H-1,2,4-triazol-5-yl)methyl][1,1'-biphenyl]-2-yl]-1H-tetrazole;
5-[4'-[(1-butyl-3-mercapto-1H-1,2,4-triazol-5-yl)methyl][1,1'-biphenyl]-2-yl]-1H-tetrazole;
5-[4'-[(1-butyl-3-thiomethyl-1H-1,2,4-triazol-5-yl)methyl][1,1'-biphenyl]-2-yl]-1H-tetrazole;
5-[4'-[(1-butyl-3-thioethyl-1H-1,2,4-triazol-5-yl)methyl][1,1'-biphenyl]-2-yl]-1H-tetrazole;

5-[4'-[(1-butyl-3-thiopropyl-1H-1,2,4-triazol-5-yl)methyl][1,1'-biphenyl]-2-yl]-1H-tetrazole;
5-[4'-[(1-butyl-3-hydroxy-1H-1,2,4-triazol-5-yl)methyl][1,1'-biphenyl]-2-yl]-1H-tetrazole;
5-[4'-[(1-butyl-3-methoxy-1H-1,2,4-triazol-5-yl)methyl][1,1'-biphenyl]-2-yl]-1H-tetrazole;
5-[4'-[(1-butyl-3-ethoxy-1H-1,2,4-triazol-5-yl)methyl][1,1'-biphenyl]-2-yl]-1H-tetrazole;
5-[4'-[(1-butyl-3-propoxy-1H-1,2,4-triazol-5-yl)methyl][1,1'-biphenyl]-2-yl]-1H-tetrazole;
5-[4 -[(1-butyl-3-butoxy-1H-1,2,4-triazol-5-yl)methyl][1,1'-biphenyl]-2-yl]-1H-tetrazole;
5-[4'-[(1-butyl-3-cyclohexyl-1H-1,2,4-triazol-5-yl)methyl][1,1'-biphenyl]-2-yl]-1H-tetrazole;
5-[4'-[(1-butyl-3-cyclohexylmethyl-1H-1,2,4-triazol-5-yl)methyl][1,1'-biphenyl]-2-yl]-1H-tetrazole;
5-[4'-[[1-butyl-3-(2-cyclohexylethyl))-1H-1,2,4-triazol-5-yl]methyl][1,1'-biphenyl]-2-yl]-1H-tetrazole;
5-[4'-[[1-butyl-3-(1,1-difluoro-2-cyclohexylethyl))-1H-1,2,4-triazol-5-yl]methyl][1,1'-biphenyl]-2-yl]-1H-tetrazole;
5-[4'-[[1-butyl-3-(1,1-difluoro-3-cyclohexylpropyl))-1H-1,2,4-triazol-5-yl]methyl][1,1'-biphenyl]-2-yl]-1H-tetrazole;
5-[4'-[(1-butyl-3-cyclohexanoyl-1,2,4,-triazol-5-yl)methyl][1,1'-biphenyl]-2-yl]-1H-tetrazole;
5-[4'-[[1-butyl-3-(1-oxo-2-cyclohexylethyl)-1H-1,2,4-triazol-5-yl]methyl][1,1'-biphenyl]-2-yl]-1H-tetrazole;
5-[4'-[(1-butyl-3-phenyl-1,2,4,-triazol-5-yl)methyl][1,1'-biphenyl]-2-yl]-1H-tetrazole;
5-[4'-[(1-butyl-3-phenylmethyl-1,2,4,-triazol-5-yl)methyl][1,1'-biphenyl]-2-yl]-1H-tetrazole;
5-[4'-[[1-butyl-3-(2-phenylethyl)-1H-1,2,4-triazol-5-yl]methyl][1,1'-biphenyl]-2-yl]-1H-tetrazole;
5-[4'-[[1-butyl-3-(1,1-difluoro-2-phenylethyl)-1H-1,2,4-triazol-5-yl]methyl][1,1'-biphenyl]-2-yl]-1H-tetrazole;
5-[4'-[[1-butyl-3-(1,1-difluoro-3-phenylpropyl)-1H-1,2,4-triazol-5-yl]methyl][1,1'-biphenyl]-2-yl]-1H-tetrazole;
5-[4'-[(1-butyl-3-benzoyl-1,2,4,-triazol-5-yl)methyl][1,1'-biphenyl]-2-yl]-1H-tetrazole;
5-[4'-[[1-butyl-3-(1-oxo-2-phenylethyl)-1H-1,2,4-triazol-5-yl]methyl][1,1'-biphenyl]-2-yl]-1H-tetrazole;
5-[4'-[[1-butyl-3-(1,1 dimethoxypropyl)-1H-1,2,4-triazol-5-yl]methyl][1,1'-biphenyl]-2-yl]-1H-tetrazole;
5-[4'-[[1-butyl-3-(1,1 dimethoxybutyl)-1H-1,2,4-triazol-5-yl]methyl][1,1'-biphenyl]-2-yl]-1H-tetrazole;
5-[4'-[[1-butyl-3-(1,1 dimethoxypentyl)-1H-1,2,4-triazol-5-yl]methyl][1,1'-biphenyl]-2-yl]-1H-tetrazole;
5-[4'-[[1-butyl-3-(1-oxopropyl)-1H-1,2,4-triazol-5-yl]methyl][1,1'-biphenyl]-2-yl]-1H-tetrazole;
5-[4'-[[1-butyl-3-(1-oxobutyl)-1H-1,2,4-triazol-5-yl]methyl][1,1'-biphenyl]-2-yl]-1H-tetrazole;
5-[4'-[[1-butyl-3-(1-oxopentyl)-1H-1,2,4-triazol-5-yl]methyl][1,1'-biphenyl]-2-yl]-1H-tetrazole;
5-[4'-[[1-butyl-3-(1,1-difluoroethyl)-1H-1,2,4-triazol-5-yl]methyl][1,1'-biphenyl]-2-yl]-1H-tetrazole;
5-[4'-[[1-butyl-3-(1,1-difluoropropyl)-1H-1,2,4-triazol-5-yl]methyl][1,1'-biphenyl]-2-yl]-1H-tetrazole;
5-[4'-[[1-butyl-3-(1,1-difluorobutyl)-1H-1,2,4-triazol-5-yl]methyl][1,1'-biphenyl]-2-yl]-1H-tetrazole;
5-[4'-[[3-butyl-5-(1,1-difluorobutyl)-1H-1,2,4-triazol-5-yl]methyl][1,1'-biphenyl]-2-yl]-1H-tetrazole;
5-[4'-[[1-butyl-3-(1,1-difluoropentyl)-1H-1,2,4-triazol-5-yl]methyl][1,1'-biphenyl]-2-yl]-1H-tetrazole;
5-[4'-[(1-propyl-3-ethyl-1H-1,2,4-triazol-5-yl)methyl][1,1'-biphenyl]-2-yl]-1H-tetrazole;
5-[4'-[(1,3-dipropyl-1H-1,2,4-triazol-5-yl)methyl][1,1'-biphenyl]-2-yl]-1H-tetrazole;
5-[4'-[(1,3-isopropyl-1H-1,2,4-triazol-5-yl)methyl][1,1'-biphenyl]-2-yl]-1H-tetrazole;
5-[4'-[4'-[(1-propyl-3-isopropyl-1H-1,2,4-triazol-5-yl)methyl][1,1'-biphenyl]-2-yl]-1H-tetrazole;
5-[4'-[(1-propyl-3-butyl-1H-1,2,4-triazol-5-yl)methyl][1,1'-biphenyl]-2-yl]-1H-tetrazole;
5-[4'-[(1-propyl-3-secbutyl-1H-1,2,4-triazol-5-yl)methyl][1,1'-biphenyl]-2-yl]-1H-tetrazole;
5-[4'-[(1-propyl-3-isobutyl-1H-1,2,4-triazol-5-yl)methyl][1,1'-biphenyl]-2-yl]-1H-tetrazole;
5-[4'-[(1-propyl-3-tertbutyl-1H-1,2,4-triazol-5-yl)methyl][1,1'-biphenyl]-2-yl]-1H-tetrazole;
5-[4'-[(1-propyl-3-pentyl-1H-1,2,4-triazol-5-yl)methyl][1,1'-biphenyl]-2-yl]-1H-tetrazole;
5-[4'-[(1-propyl-3-isopentyl-1H-1,2,4-triazol-5-yl)methyl][1,1'-biphenyl]-2-yl]-1H-tetrazole;
5-[4'-[(1-propyl-3-mercapto-1H-1,2,4-triazol-5-yl)methyl][1,1'-biphenyl]-2-yl]-1H-tetrazole;
5-[4'-[(1-propyl-3-thiomethyl-1H-1,2,4-triazol-5-yl)methyl][1,1'-biphenyl]-2-yl]-1H-tetrazole;
5-[4'-[(1-propyl-3-thioethyl-1H-1,2,4-triazol-5-yl)methyl][1,1'-biphenyl]-2-yl]-1H-tetrazole;
5-[4'-[(1-propyl-3-thiopropyl-1H-1,2,4-triazol-5-yl)methyl][1,1'-biphenyl]-2-yl]-1H-tetrazole;
5-[4'-[(1-propyl-3-hydroxy-1H-1,2,4-triazol-5-yl)methyl][1,1'-biphenyl]-2-yl]-1H-tetrazole;
5-[4'-[(1-propyl-3-methoxy-1H-1,2,4-triazol-5-yl)methyl][1,1'-biphenyl]-2-yl]-1H-tetrazole;
5-[4'-[(1-propyl-3-ethoxy-1H-1,2,4-triazol-5-yl)methyl][1,1'-biphenyl]-2-yl]-1H-tetrazole;
5-[4'-[(1-propyl-3-propoxy-1H-1,2,4-triazol-5-yl)methyl][1,1'-biphenyl]-2-yl]-1H-tetrazole;
5-[4 -[(1-propyl-3-cyclohexyl-1H-1,2,4-triazol-5-yl)methyl][1,1'-biphenyl]-2-yl]-1H-tetrazole;
5-[4'-[(1-propyl-3-cyclohexylmethyl-1H-1,2,4-triazol-5-yl)methyl][1,1'-biphenyl]-2-yl]-1H-tetrazole;
5-[5-[4'-[[1-propyl-3-(2-cyclohexylethyl)-1H-1,2,4-triazol-5-yl]methyl][1,1'-biphenyl]-2-yl]-1H-tetrazole;
5-[4'-[(1-propyl-3-cyclohexanoyl-1H-1,2,4-triazol-5-yl)methyl][1,1'-biphenyl]-2-yl]-1H-tetrazole;
5-[5-[4'-[[1-propyl-3-(1-oxo-2-cyclohexylethyl)-1H-1,2,4-triazol-5-yl]methyl][1,1'-biphenyl]-2-yl]-1H-tetrazole;
5-[4'-[(1-propyl-3-phenyl-1H-1,2,4-triazol-5-yl)methyl][1,1'-biphenyl]-2-yl]-1H-tetrazole;
5-[4'-[(1-propyl-3-phenylmethyl-1H-1,2,4-triazol-5-yl)methyl][1,1'-biphenyl]-2-yl]-1H-tetrazole;
5-[4'-[[1-propyl-3-(2-phenylethyl)-1H-1,2,4-triazol-5-yl]methyl][1,1'-biphenyl]-2-yl]-1H-tetrazole;
5-[4'-[(1-propyl-3-benzoyl-1H-1,2,4-triazol-5-yl)methyl][1,1'-biphenyl]-2-yl]-1H-tetrazole;
5-[4'-[[1-propyl-3-(1-oxo-2-phenylethyl)-1H-1,2,4-triazol-5-yl]methyl][1,1'-biphenyl]-2-yl]-1H-tetrazole;
5-[4'-[[1-propyl-3-(1,1-dimethoxypropyl)-1H-1,2,4-triazol-5-yl]methyl][1,1'-biphenyl]-2-yl]-1H-tetrazole;
5-[4'-[[1-propyl-3-(1,1-dimethoxybutyl)-1H-1,2,4-triazol-5-yl]methyl][1,1'-biphenyl]-2-yl]-1H-tetrazole;
5-[4'-[[1-propyl-3-(1,1-dimethoxypentyl)-1H-1,2,4-triazol-5-yl]methyl][1,1'-biphenyl]-2-yl]-1H-tetrazole;
5-[4'-[[1-propyl-3-(1-oxopropyl)-1H-1,2,4-triazol-5-yl]methyl][1,1'-biphenyl]-2-yl]-1H-tetrazole;
5-[4'-[[1-propyl-3-(1-oxobutyl)-1H-1,2,4-triazol-5-yl]methyl][1,1'-biphenyl]-2-yl]-1H-tetrazole;
5-[4'-[[1-propyl-3-(1-oxopentyl)-1H-1,2,4-triazol-5-yl]methyl][1,1'-biphenyl]-2-yl]-1H-tetrazole;

5-[4'-[[1-propyl-3-(1,1-difluoroethyl)-1H-1,2,4-triazol-5-yl]methyl][1,1'-biphenyl]-2-yl]-1H-tetrazole;
5-[4'-[[1-cyclohexyl-3-heptafluoropropyl-1H-1,2,4-triazol-5-yl]methyl][1,1'-biphenyl]-2-yl]-1H-tetrazole;
5-[4'-[[1-propyl-3-(1,1-difluoropropyl)-1H-1,2,4-triazol-5-yl]methyl][1,1'-biphenyl]-2-yl]-1H-tetrazole;
5-[4'-[[1-propyl-3-(1,1-difluorobutyl)-1H-1,2,4-triazol-5-yl]methyl][1,1'-biphenyl]-2-yl]-1H-tetrazole;
5-[4'-[[1-propyl-3-(1,1-difluoropentyl)-1H-1,2,4-triazol-5-yl]methyl][1,1'-biphenyl]-2-yl]-1H-tetrazole;
5-[4'-[(1,3-diethyl-1H-1,2,4-triazol-5-yl)methyl][1,1'-biphenyl]-2-yl]-1H-tetrazole;
5-[4'-[(1-ethyl-3-propyl-1H-1,2,4-triazol-5-yl)methyl][1,1,-biphenyl]-2-yl]-1H-tetrazole;
5-[4'-[(1-ethyl-3-isopropyl-1H-1,2,4-triazol-5-yl)methyl][1,1'-biphenyl]-2-yl]-1H-tetrazole;
5-[4'-[(1-ethyl-3-butyl-1H-1,2,4-triazol-5-yl)methyl][1,1'-biphenyl]-2-yl]-1H-tetrazole;
5-[4'-[(1-ethyl-3-secbutyl-1H-1,2,4-triazol-5-yl)methyl][1,1'-biphenyl]-2-yl]-1H-tetrazole;
5-[4'-[(1-ethyl-3-isobutyl-1H-1,2,4-triazol-5-yl)methyl][1,1'-biphenyl]-2-yl]-1H-tetrazole;
5-[4'-[(1-ethyl-3-tertbutyl-1H-1,2,4-triazol-5-yl)methyl][1,1'-biphenyl]-2-yl]-1H-tetrazole;
5-[4'-[(1-ethyl-3-pentyl-1H-1,2,4-triazol-5-yl)methyl][1,1'-biphenyl]-2-yl]-1H-tetrazole;
5-[4'-[(1-ethyl-3-isopentyl-1H-1,2,4-triazol-5-yl)methyl][1,1'-biphenyl]-2-yl]-1H-tetrazole;
5-[4 -[(1-ethyl-3-mercapto-1H-1,2,4-triazol-5-yl)methyl][1,1'-biphenyl]-2-yl]-1H-tetrazole;
5-[4,-[(1-ethyl-3-thiomethyl-1H-1,2,4-triazol-5-yl)methyl][1,1'-biphenyl]-2-yl]-1H-tetrazole;
5-[4'-[(1-ethyl-3-thioethyl-1H-1,2,4-triazol-5-yl)methyl][1,1'-biphenyl]-2-yl]-1H-tetrazole;
5-[4'-[(1-ethyl-3-thiopropyl-1H-1,2,4-triazol-5-yl)methyl][1,1'-biphenyl]-2-yl]-1H-tetrazole; 5-[4'-[(1-ethyl-3-hydroxy-1H-1,2,4-triazol-5-yl)methyl][1,1'-biphenyl]-2-yl]-1H-tetrazole;
5-[4'-[(1-ethyl-3-methoxy-1H-1,2,4-triazol-5-yl)methyl][1,1'-biphenyl]-2-yl]-1H-tetrazole;
5-[4'-[(1-ethyl-3-ethoxy-1H-1,2,4-triazol-5-yl)methyl][1,1'-biphenyl]-2-yl]-1H-tetrazole;
5-[4'-[(1-ethyl-3-propoxy-1H-1,2,4-triazol-5-yl)methyl][1,1'-biphenyl]-2-yl]-1H-tetrazole;
5-[4'-[(1-ethyl-3-cyclohexyl-1H-1,2,4-triazol-5-yl)methyl][1,1'-biphenyl]-2-yl]-1H-tetrazole;
5-[4'-[(1-ethyl-3-cyclohexylmethyl-1H-1,2,4-triazol-5-yl)methyl][1,1'-biphenyl]-2-yl]-1H-tetrazole;
5-[4'-[[1-ethyl-3-(2-cyclohexylethyl)-1H-1,2,4-triazol-5-yl]methyl][1,1'-biphenyl]-2-yl]-1H-tetrazole;
5-[4'-[(1-ethyl-3-cyclohexanoyl-1H-1,2,4-triazol-5-yl)methyl][1,1'-biphenyl]-2-yl]-1H-tetrazole;
5-[4'-[[1-ethyl-3-(1-oxo-2-cyclohexylethyl)-1H-1,2,4-triazol-5-yl]methyl][1,1'-biphenyl]-2-yl]-1H-tetrazole;
5-[4'-[(1-ethyl-3-phenyl-1H-1,2,4-triazol-5-yl)methyl][1,1'-biphenyl]-2-yl]-1H-tetrazole;
5-[4'-[(1-ethyl-3-phenylmethyl-1H-1,2,4-triazol-5-yl)methyl][1,1'-biphenyl]-2-yl]-1H-tetrazole;
5-[4'-[[1-ethyl-3-(2-phenylethyl)-1H-1,2,4-triazol-5-yl]methyl][1,1'-biphenyl]-2-yl]-1H-tetrazole;
5-[4'-[(1-ethyl-3-benzoyl-1H-1,2,4-triazol-5-yl)methyl][1,1'-biphenyl]-2-yl]-1H-tetrazole;
5-[4'-[[1-ethyl-3-(1-oxo-2-phenylethyl)-1H-1,2,4-triazol-5-yl]methyl][1,1'-biphenyl]-2-yl]-1H-tetrazole;
5-[4'-[[1-ethyl-3-(1,1-dimethoxypropyl)-1H-1,2,4-triazol-5-yl]methyl][1,1'-biphenyl]-2-yl]-1H-tetrazole;
5-[4'-[[1-ethyl-3-(1,1-dimethoxybutyl)-1H-1,2,4-triazol-5-yl]methyl][1,1'-biphenyl]-2-yl]-1H-tetrazole;
5-[4'-[[1-ethyl-3-(1,1-dimethoxypentyl)-1H-1,2,4-triazol-5-yl]methyl][1,1'-biphenyl]-2-yl]-1H-tetrazole;
5-[4'-[[1-ethyl-3-(1-oxopropyl)-1H-1,2,4-triazol-5-yl]methyl][1,1'-biphenyl]-2-yl]-1H-tetrazole;
5-[4'-[[1-ethyl-3-(1-oxobutyl)-1H-1,2,4-triazol-5-yl]methyl][1,1'-biphenyl]-2-yl]-1H-tetrazole;
5-[4'-[[1-ethyl-3-(1-oxopentyl)-1H-1,2,4-triazol-5-yl]methyl][1,1'-biphenyl]-2-yl]-1H-tetrazole;
5-[4'-[[1-ethpyl-3-(1,1-difluoroethyl)-1H-1,2,4-triazol-5-yl]methyl][1,1'-biphenyl]-2-yl]-1H-tetrazole;
5-[4'-[[1-ethyl-3-(1,1-difluoropropyl)-1H-1,2,4-triazol-5-yl]methyl][1,1'-biphenyl]-2-yl]-1H-tetrazole;
5-[4 -[[1-ethyl-3-(1,1-difluorobutyl)-1H-1,2,4-triazol-5-yl]methyl][1,1'-biphenyl]-2-yl]-1H-tetrazole;
5-[4,-[[1-ethyl-3-(1,1-difluoropentyl)-1H-1,2,4-triazol-5-yl]methyl][1,1'-biphenyl]-2-yl]-1H-tetrazole;
5-[4'-[(1-secbutyl-3-ethyl-1H-1,2,4-triazol-5-yl)methyl][1,1'-biphenyl]-2-yl]-1H-tetrazole;
5-[4'-[(1-secbutyl-3-propyl-1H-1,2,4-triazol-5-yl)methyl][1,1'-biphenyl]-2-yl]-1H-tetrazole;
5-[4'-[(1-secbutyl-3-isopropyl-1H-1,2,4-triazol-5-yl)methyl][1,1'-biphenyl]-2-yl]-1H-tetrazole;
5-[4'-[(1-secbutyl-3-butyl-1H-1,2,4-triazol-5-yl)methyl][1,1'-biphenyl]-2-yl]-1H-tetrazole;
5-[4'-[(1,3-disecbutyl-1H-1,2,4-triazol-5-yl)methyl][1,1'-biphenyl]-2-yl]-1H-tetrazole;
5-[4'-[(1-secbutyl-3-isobutyl-1H-1,2,4-triazol-5-yl)methyl][1,1'-biphenyl]-2-yl]-1H-tetrazole;
5-[4'-[(1-secbutyl-3-tertbutyl-1H-1,2,4-triazol-5-yl)methyl][1,1'-biphenyl]-2-yl]-1H-tetrazole;
5-[4'-[(1-secbutyl-3-pentyl-1H-1,2,4-triazol-5-yl)methyl][1,1'-biphenyl]-2-yl]-1H-tetrazole;
5-[4'-[(1-secbutyl-3-isopentyl-1H-1,2,4-triazol-5-yl)methyl][1,1'-biphenyl]-2-yl]-1H-tetrazole;
5-[4'-[(1-secbutyl-3-mercapto-1H-1,2,4-triazol-5-yl)methyl][1,1'-biphenyl]-2-yl]-1H-tetrazole;
5-[4'-[(1-secbutyl-3-thiomethyl-1H-1,2,4-triazol-5-yl)methyl][1,1'-biphenyl]-2-yl]-1H-tetrazole;
5-[4'-[(1-secbutyl-3-thioethyl-1H-1,2,4-triazol-5-yl)methyl][1,1'-biphenyl]-2-yl]-1H-tetrazole;
5-[4'-[(1-secbutyl-3-thiopropyl-1H-1,2,4-triazol-5-yl)methyl][1,1'-biphenyl]-2-yl]-1H-tetrazole;
5-[4'-[(1-secbutyl-3-hydroxy-1H-1,2,4-triazol-5-yl)methyl][1,1'-biphenyl]-2-yl]-1H-tetrazole;
5-[4'-[(1-secbutyl-3-methoxy-1H-1,2,4-triazol-5-yl)methyl][1,1'-biphenyl]-2-yl]-1H-tetrazole;
5-[4'-[(1-secbutyl-3-ethoxy-1H-1,2,4-triazol-5-yl)methyl][1,1'-biphenyl]-2-yl]-1H-tetrazole;
5-[4'-[(1-secbutyl-3-propoxy-1H-1,2,4-triazol-5-yl)methyl][1,1'-biphenyl]-2-yl]-1H-tetrazole;
5-[4'-[(1-secbutyl-3-cyclohexyl-1H-1,2,4-triazol-5-yl)methyl][1,1'-biphenyl]-2-yl]-1H-tetrazole;
5-[4'-[(1-secbutyl-3-cyclohexylmethyl-1H-1,2,4-triazol-5-yl)methyl][1,1'-biphenyl]-2-yl]-1H-tetrazole;
5-[4'-[[1-secbutyl-3-(2-cyclohexylethyl)-1H-1,2,4-triazol-5-yl]methyl][1,1'-biphenyl]-2-yl]-1H-tetrazole;
5-[4'-[(1-secbutyl-3-cyclohexanoyl-1H-1,2,4-triazol-5-yl)methyl][1,1'-biphenyl]-2-yl]-1H-tetrazole;
5-[4'-[[1-secbutyl-3-(1-oxo-2-cyclohexylethyl)-1H-1,2,4-triazol-5-yl]methyl][1,1'-biphenyl]-2-yl]-1H-tetrazole;
5-[4'-[(1-secbutyl-3-phenyl-1H-1,2,4-triazol-5-yl)methyl][1,1'-biphenyl]-2-yl]-1H-tetrazole;
5-[4'-[(1-secbutyl-3-phenylmethyl-1H-1,2,4-triazol-5-yl)methyl][1,1'-biphenyl]-2-yl]-1H-tetrazole;
5-[4'-[[1-secbutyl-3-(2-phenylethyl)-1H-1,2,4-triazol-5-yl]methyl][1,1'-biphenyl]-2-yl]-1H-tetrazole;
5-[4'-[(1-secbutyl-3-benzoyl-1H-1,2,4-triazol-5-yl)methyl][1,1'-biphenyl]-2-yl]-1H-tetrazole;

5-[4'-[[1-secbutyl-3-(1-oxo-2-phenylethyl)-1H-1,2,4-triazol-5-yl]methyl][1,1'-biphenyl]-2-yl]-1H-tetrazole;
5-[4'-[[1-secbutyl-3-(1,1-dimethoxypropyl)-1H-1,2,4-triazol-5-yl]methyl][1,1'-biphenyl]-2-yl]-1H-tetrazole;
5-[4'-[[1-secbutyl-3-(1,1-dimethoxybutyl)-1H-1,2,4-triazol-5-yl]methyl][1,1'-biphenyl]-2-yl]-1H-tetrazole;
5-[4'-[[1-secbutyl-3-(1,1-dimethoxypentyl)-1H-1,2,4-triazol-5-yl]methyl][1,1'-biphenyl]-2-yl]-1H-tetrazole;
5-[4'-[[1-secbutyl-3-(1-oxopropyl)-1H-1,2,4-triazol-5-yl]methyl][1,1'-biphenyl]-2-yl]-1H-tetrazole;
5-[4'-[[1-secbutyl-3-(1-oxobutyl)-1H-1,2,4-triazol-5-yl]methyl][1,1'-biphenyl]-2-yl]-1H-tetrazole;
5-[4'-[[1-secbutyl-3-(1-oxopentyl)-1H-1,2,4-triazol-5-yl]methyl][1,1'-biphenyl]-2-yl]-1H-tetrazole;
5-[4'-[[1-secbutyl-3-(1,1-difluoroethyl)-1H-1,2,4-triazol-5-yl]methyl][1,1'-biphenyl]-2-yl]-1H-tetrazole;
5-[4'-[[1-secbutyl-3-(1,1-difluoropropyl)-1H-1,2,4-triazol-5-yl]methyl][1,1'-biphenyl]-2-yl]-1H-tetrazole;
5-[4'-[[1-secbutyl-3-(1,1-difluorobutyl)-1H-1,2,4-triazol-5-yl]methyl][1,1'-biphenyl]-2-yl]-1H-tetrazole;
5-[4'-[[1-secbutyl-3-(1,1-difluoropentyl)-1H-1,2,4-triazol-5-yl]methyl][1,1'-biphenyl]-2-yl]-1H-tetrazole;
5-[4'-[(1-isobutyl-3-ethyl-1H-1,2,4-triazol-5-yl)methyl][1,1'-biphenyl]-2-yl]-1H-tetrazole;
5-[4'-[(1-isobutyl-3-propyl-1H-1,2,4-triazol-5-yl)methyl][1,1'-biphenyl]-2-yl]-1H-tetrazole;
5-[4'-[(1-isobutyl-3-isopropyl-1H-1,2,4-triazol-5-yl)methyl][1,1'-biphenyl]-2-yl]-1H-tetrazole;
5-[4'-[(1-isobutyl-3-butyl-1H-1,2,4-triazol-5-yl)methyl][1,1'-biphenyl]-2-yl]-1H-tetrazole;
5-[4'-[(1-isobutyl-3-secbutyl-1H-1,2,4-triazol-5-yl)methyl][1,1'-biphenyl]-2-yl]-1H-tetrazole;
5-[4'-[(1,3-diisobutyl-1H-1,2,4-triazol-5-yl)methyl][1,1'-biphenyl]-2-yl]-1H-tetrazole;
5-[4'-[(1-isobutyl-3-tertbutyl-1H-1,2,4-triazol-5-yl)methyl][1,1'-biphenyl]-2-yl]-1H-tetrazole;
5-[4'-[(1-isobutyl-3-pentyl-1H-1,2,4-triazol-5-yl)methyl][1,1'-biphenyl]-2-yl]-1H-tetrazole;
5-[4'-[(1-isobutyl-3-isopentyl-1H-1,2,4-triazol-5-yl)methyl][1,1'-biphenyl]-2-yl]-1H-tetrazole;
5-[4'-[(1-isobutyl-3-mercapto-1H-1,2,4-triazol-5-yl)methyl][1,1'-biphenyl]-2-yl]-1H-tetrazole;
5-[4'-[(1-isobutyl-3-thiomethyl-1H-1,2,4-triazol-5-yl)methyl][1,1'-biphenyl]-2-yl]-1H-tetrazole;
5-[4'-[(1-isobutyl-3-thioethyl-1H-1,2,4-triazol-5-yl)methyl][1,1'-biphenyl]-2-yl]-1H-tetrazole;
5-[4'-[(1-isobutyl-3-thiopropyl-1H-1,2,4-triazol-5-yl)methyl][1,1'-biphenyl]-2-yl]-1H-tetrazole;
5-[4'-[(1-isobutyl-3-hydroxy-1H-1,2,4-triazol-5-yl)methyl][1,1'-biphenyl]-2-yl]-1H-tetrazole;
5-[4'-[(1-isobutyl-3-methoxy-1H-1,2,4-triazol-5-yl)methyl][1,1'-biphenyl]-2-yl]-1H-tetrazole;
5-[4'-[(1-isobutyl-3-ethoxy-1H-1,2,4-triazol-5-yl)methyl][1,1'-biphenyl]-2-yl]-1H-tetrazole;
5-[4'-[(1-isobutyl-3-propoxy-1H-1,2,4-triazol-5-yl)methyl][1,1'-biphenyl]-2-yl]-1H-tetrazole;
5-[4'-[(1-3-cyclohexyl-1H-1,2,4-triazol-5-yl)methyl][1,1'-biphenyl]-2-yl]-1H-tetrazole;
5-[4'-[(1-isobutyl-3-cyclohexylmethyl-1H-1,2,4-triazol-5-yl)methyl][1,1'-biphenyl]-2-yl]-1H-tetrazole;
5-[4'-[[1-isobutyl-3-(2-cyclohexylethyl)-1H-1,2,4-triazol-5-yl]methyl][1,1'-biphenyl]-2-yl]-1H-tetrazole;
5-[4'-[(1-isobutyl-3-cyclohexanoyl-1H-1,2,4-triazol-5-yl)methyl][1,1'-biphenyl]-2-yl]-1H-tetrazole;
5-[4'-[[1-isobutyl-3-(1-oxo-2-cyclohexylethyl)-1H-1,2,4-triazol-5-yl]methyl][1,1'-biphenyl]-2-yl]-1H-tetrazole;
5-[4'-[(1-isobutyl-3-phenyl-1H-1,2,4-triazol-5-yl)methyl][1,1'-biphenyl]-2-yl]-1H-tetrazole;
5-[4'-[(1-isobutyl-3-phenylmethyl-1H-1,2,4-triazol-5-yl)methyl][1,1'-biphenyl]-2-yl]-1H-tetrazole;
5-[4'-[[1-isobutyl-3-(2-phenylethyl)-1H-1,2,4-triazol-5-yl]methyl][1,1'-biphenyl]-2-yl]-1H-tetrazole;
5-[4'-[(1-isobutyl-3-benzoyl-1H-1,2,4-triazol-5-yl)methyl][1,1'-biphenyl]-2-yl]-1H-tetrazole;
5-[4'-[[1-isobutyl-3-(1-oxo-2-phenylethyl)-1H-1,2,4-triazol-5-yl]methyl][1,1'-biphenyl]-2-yl]-1H-tetrazole;
5-[4'-[[1-isobutyl-3-(1,1-dimethoxypropyl)-1H-1,2,4-triazol-5-yl]methyl][1,1'-biphenyl]-2-yl]-1H-tetrazole;
5-[4'-[[1-isobutyl-3-(1,1-dimethoxybutyl)-1H-1,2,4-triazol-5-yl]methyl][1,1'-biphenyl]-2-yl]-1H-tetrazole;
5-[4'-[[1-isobutyl-3-(1,1-dimethoxypentyl)-1H-1,2,4-triazol-5-yl]methyl][1,1'-biphenyl]-2-yl]-1H-tetrazole;
5-[4 -[[1-isobutyl-3-(1-oxopropyl)-1H-1,2,4-triazol-5-yl]methyl][1,1'-biphenyl]-2-yl]-1H-tetrazole;
5-[4'-[[1-isobutyl-3-(1-oxobutyl)-1H-1,2,4-triazol-5-yl]methyl][1,1'-biphenyl]-2-yl]-1H-tetrazole;
5-[4'-[[1-isobutyl-3-(1-oxopentyl)-1H-1,2,4-triazol-5-yl]methyl][1,1'-biphenyl]-2-yl]-1H-tetrazole;
5-[4'-[[1-isobutyl-3-(1,1-difluoroethyl)-1H-1,2,4-triazol-5-yl]methyl][1,1'-biphenyl]-2-yl]-1H-tetrazole;
5-[4'-[[1-isobutyl-3-(1,1-difluoropropyl)-1H-1,2,4-triazol-5-yl]methyl][1,1'-biphenyl]-2-yl]-1H-tetrazole;
5-[4'-[[1-isobutyl-3-(1,1-difluorobutyl)-1H-1,2,4-triazol-5-yl]methyl][1,1'-biphenyl]-2-yl]-1H-tetrazole;
5-[4 -[[1-isobutyl-3-(1,1-difluoropentyl)-1H-1,2,4-triazol-5-yl]methyl][1,1'-biphenyl]-2-yl]-1H-tetrazole;
5-[4'-[(1-tertbutyl-3-ethyl-1H-1,2,4-triazol-5-yl)methyl][1,1'-biphenyl]-2-yl]-1H-tetrazole;
5-[4'-[(1-tertbutyl-3-propyl-1H-1,2,4-triazol-5-yl)methyl][1,1'-biphenyl]-2-yl]-1H-tetrazole;
5-[4'-[(1-tertbutyl-3-isopropyl-1H-1,2,4-triazol-5-yl)methyl][1,1'-biphenyl]-2-yl]-1H-tetrazole;
5-[4'-[(1-tertbutyl-3-butyl-1H-1,2,4-triazol-5-yl)methyl][1,1'-biphenyl]-2-yl]-1H-tetrazole;
5-[4 -[(1-tertbutyl-3-secbutyl-1H-1,2,4-triazol-5-yl)methyl][1,1'-biphenyl]-2-yl]-1H-tetrazole;
5-[4'-[(1-tertbutyl-3-isobutyl-1H-1,2,4-triazol-5-yl)methyl][1,1'-biphenyl]-2-yl]-1H-tetrazole;
5-[4'-[(1,3-ditertbutyl-1H-1,2,4-triazol-5-yl)methyl][1,1'-biphenyl]-2-yl]-1H-tetrazole;
5-[4'-[(1-tertbutyl-3-pentyl-1H-1,2,4-triazol-5-yl)methyl][1,1'-biphenyl]-2-yl]-1H-tetrazole;
5-[4'-[(1-tertbutyl-3-isopentyl-1H-1,2,4-triazol-5-yl)methyl][1,1'-biphenyl]-2-yl]-1H-tetrazole;
5-[4'-[(1-tertbutyl-3-mercapto-1H-1,2,4-triazol-5-yl)methyl][1,1'-biphenyl]-2-yl]-1H-tetrazole;
5-[4'-[(1-tertbutyl-3-thiomethyl-1H-1,2,4-triazol-5-yl)methyl][1,1'-biphenyl]-2-yl]-1H-tetrazole;
5-[4'-[(1-tertbutyl-3-thioethyl-1H-1,2,4-triazol-5-yl)methyl][1,1'-biphenyl]-2-yl]-1H-tetrazole;
5-[4'-[(1-tertbutyl-3-thiopropyl-1H-1,2,4-triazol-5-yl)methyl][1,1'-biphenyl]-2-yl]-1H-tetrazole;
5-[4'-[(1-tertbutyl-3-hydroxy-1H-1,2,4-triazol-5-yl)methyl][1,1'-biphenyl]-2-yl]-1H-tetrazole;
5-[4'-[(1-tertbutyl-3-methoxy-1H-1,2,4-triazol-5-yl)methyl][1,1'-biphenyl]-2-yl]-1H-tetrazole;
5-[4'-[(1-tertbutyl-3-ethoxy-1H-1,2,4-triazol-5-yl)methyl][1,1'-biphenyl]-2-yl]-1H-tetrazole;
5-[4'-[(1-tertbutyl-3-propoxy-1H-1,2,4-triazol-5-yl)methyl][1,1'-biphenyl]-2-yl]-1H-tetrazole;
5-[4'-[(1-tertbutyl-3-cyclohexyl-1H-1,2,4-triazol-5-yl)methyl][1,1'-biphenyl]-2-yl]-1H-tetrazole;
5-[4'-[(1-tertbutyl-3-cyclohexylmethyl-1H-1,2,4-triazol-5-yl)methyl][1,1'-biphenyl]-2-yl]-1H-tetrazole;
5-[4'-[[1-tertbutyl-3-(2-cyclohexylethyl)-1H-1,2,4-triazol-5-yl]methyl][1,1'-biphenyl]-2-yl]-1H-tetrazole;

5-[4'-[(1-tertbutyl-3-cyclohexanoyl-1H-1,2,4-triazol-5-yl)methyl][1,1'-biphenyl]-2-yl]-1H-tetrazole;
5-[4'-[[1-tertbutyl-3-(1-oxo-2-cyclohexylethyl)-1H-1,2,4-triazol-5-yl]methyl][1,1'-biphenyl]-2-yl]-1H-tetrazole;
5-[4'-[(1-tertbutyl-3-phenyl-1H-1,2,4-triazol-5-yl)methyl][1,1'-biphenyl]-2-yl]-1H-tetrazole;
5-[4'-[(1-tertbutyl-3-phenylmethyl-1H-1,2,4-triazol-5-yl)methyl][1,1,-biphenyl]-2-yl]-1H-tetrazole;
5-[4'-[[1-tertbutyl-3-(2-phenylethyl)-1H-1,2,4-triazol-5-yl]methyl][1,1'-biphenyl]-2-yl]-1H-tetrazole;
5-[4'-[(1-tertbutyl-3-benzoyl-1H-1,2,4-triazol-5-yl)methyl][1,1'-biphenyl]-2-yl]-1H-tetrazole;
5-[4'-[[1-tertbutyl-3-(1-oxo-2-phenylethyl)-1H-1,2,4-triazol-5-yl]methyl][1,1'-biphenyl]-2-yl]-1H-tetrazole;
5-[4'-[[1-tertbutyl-3-(1,1-dimethoxypropyl)-1H-1,2,4-triazol-5-yl]methyl][1,1'-biphenyl]-2-yl]-1H-tetrazole;
5-[4'-[[1-tertbutyl-3-(1,1-dimethoxybutyl)-1H-1,2,4-triazol-5-yl]methyl][1,1'-biphenyl]-2-yl]-1H-tetrazole;
5-[4'-[[1-tertbutyl-3-(1,1-dimethoxypentyl)-1H-1,2,4-triazol-5-yl]methyl][1,1'-biphenyl]-2-yl]-1H-tetrazole;
5-[4'-[[1-tertbutyl-3-(1-oxopropyl)-1H-1,2,4-triazol-5-yl]methyl][1,1'-biphenyl]-2-yl]-1H-tetrazole;
5-[4'-[[1-tertbutyl-3-(1-oxobutyl)-1H-1,2,4-triazol-5-yl]methyl][1,1'-biphenyl]-2-yl]-1H-tetrazole;
5-[4'-[[1-tertbutyl-3-(1-oxopentyl)-1H-1,2,4-triazol-5-yl]methyl][1,1'-biphenyl]-2-yl]-1H-tetrazole;
5-[4'-[[1-tertbutyl-3-(1,1-difluoroethyl)-1H-1,2,4-triazol-5-yl]methyl][1,1'-biphenyl]-2-yl]-1H-tetrazole;
5-[4'-[[1-tertbutyl-3-(1,1-difluoropropyl)-1H-1,2,4-triazol-5-yl]methyl][1,1'-biphenyl]-2-yl]-1H-tetrazole;
5-[4'-[[1-tertbutyl-3-(1,1-difluorobutyl)-1H-1,2,4-triazol-5-yl]methyl][1,1'-biphenyl]-2-yl]-1H-tetrazole;
5-[4'-[[1-tertbutyl-3-(1,1-difluoropentyl)-1H-1,2,4-triazol-5-yl]methyl][1,1'-biphenyl]-2-yl]-1H-tetrazole;
5-[4'-[(1-pentyl-3-ethyl-1H-1,2,4-triazol-5-yl)methyl][1,1'-biphenyl]-2-yl]-1H-tetrazole;
5-[4'-[(1-pentyl-3-propyl-1H-1,2,4-triazol-5-yl)methyl][1,1'-biphenyl]-2-yl]-1H-tetrazole;
5-[4'-[(1-pentyl-3-isopropyl-1H-1,2,4-triazol-5-yl)methyl][1,1'-biphenyl]-2-yl]-1H-tetrazole;
5-[4'-[(1-pentyl-3-butyl-1H-1,2,4-triazol-5-yl)methyl][1,1'-biphenyl]-2-yl]-1H-tetrazole;
5-[4,-[(1-pentyl-3-secbutyl-1H-1,2,4-triazol-5-yl)methyl][1,1'-biphenyl]-2-yl]-1H-tetrazole;
5-[4'-[(1-pentyl-3-isobutyl-1H-1,2,4-triazol-5-yl)methyl][1,1'-biphenyl]-2-yl]-1H-tetrazole;
5-[4'-[(1-pentyl-3-tertbutyl-1H-1,2,4-triazol-5-yl)methyl][1,1'-biphenyl]-2-yl]-1H-tetrazole;
5-[4'-[(1,3-dipentyl-1H-1,2,4-triazol-5-yl)methyl][1,1'-biphenyl]-2-yl]-1H-tetrazole;
5-[4'-[(1-pentyl-3-isopentyl-1H-1,2,4-triazol-5-yl)methyl][1,1'-biphenyl]-2-yl]-1H-tetrazole;
5-[4'-[(1-pentyl-3-mercapto-1H-1,2,4-triazol-5-yl)methyl][1,1'-biphenyl]-2-yl]-1H-tetrazole;
5-[4'-[(1-pentyl-3-thiomethyl-1H-1,2,4-triazol-5-yl)methyl][1,1'-biphenyl]-2-yl]-1H-tetrazole;
5-[4'-[(1-pentyl-3-thioethyl-1H-1,2,4-triazol-5-yl)methyl][1,1'-biphenyl]-2-yl]-1H-tetrazole;
5-[4'-[(1-pentyl-3-thiopropyl-1H-1,2,4-triazol-5-yl)methyl][1,1'-biphenyl]-2-yl]-1H-tetrazole;
5-[4'-[(1-pentyl-3-hydroxy-1H-1,2,4-triazol-5-yl)methyl][1,1'-biphenyl]-2-yl]-1H-tetrazole;
5-[4'-[(1-pentyl-3-methoxy-1H-1,2,4-triazol-5-yl)methyl][1,1'-biphenyl]-2-yl]-1H-tetrazole;
5-[4'-[(1-pentyl-3-ethoxy-1H-1,2,4-triazol-5-yl)methyl][1,1'-biphenyl]-2-yl]-1H-tetrazole;
5-[4'-[(1-pentyl-3-propoxy-1H-1,2,4-triazol-5-yl)methyl][1,1'-biphenyl]-2-yl]-1H-tetrazole;
5-[4'-[(1-pentyl-3-cyclohexyl-1H-1,2,4-triazol-5-yl)methyl][1,1'-biphenyl]-2-yl]-1H-tetrazole;
5-[4'-[(1-pentyl-3-cyclohexylmethyl-1H-1,2,4-triazol-5-yl)methyl][1,1'-biphenyl]-2-yl]-1H-tetrazole;
5-[4'-[[1-pentyl-3-(2-cyclohexylethyl)-1H-1,2,4-triazol-5-yl]methyl][1,1'-biphenyl]-2-yl]-1H-tetrazole;
5-[4'-[(1-pentyl-3-cyclohexanoyl-1H-1,2,4-triazol-5-yl)methyl][1,1'-biphenyl]-2-yl]-1H-tetrazole;
5-[4'-[[1-pentyl-3-(1-oxo-2-cyclohexylethyl)-1H-1,2,4-triazol-5-yl]methyl][1,1'-biphenyl]-2-yl]-1H-tetrazole;
5-[4'-[(1-pentyl-3-phenyl-1H-1,2,4-triazol-5-yl)methyl][1,1'-biphenyl]-2-yl]-1H-tetrazole;
5-[4'-[(1-pentyl-3-phenylmethyl-1H-1,2,4-triazol-5-yl)methyl][1,1'-biphenyl]-2-yl]-1H-tetrazole;
5-[4'-[[1-pentyl-3-(2-phenylethyl)-1H-1,2,4-triazol-5-yl]methyl][1,1'-biphenyl]-2-yl]-1H-tetrazole;
5-[4'-[[1-pentyl-3-benzoyl-1H-1,2,4-triazol-5-yl)methyl][1,1'-biphenyl]-2-yl]-1H-tetrazole;
5-[4'-[[1-pentyl-3-(1-oxo-2-phenylethyl)-1H-1,2,4-triazol-5-yl]methyl][1,1'-biphenyl]-2-yl]-1H-tetrazole;
5-[4'-[[1-pentyl-3-(1,1-dimethoxypropyl)-1H-1,2,4-triazol-5-yl]methyl][1,1'-biphenyl]-2-yl]-1H-tetrazole;
5-[4'-[[1-pentyl-3-(1,1-dimethoxybutyl)-1H-1,2,4-triazol-5-yl]methyl][1,1'-biphenyl]-2-yl]-1H-tetrazole;
5-[4'-[[1-pentyl-3-(1,1-dimethoxypentyl)-1H-1,2,4-triazol-5-yl]methyl][1,1'-biphenyl]-2-yl]-1H-tetrazole;
5-[4'-[[1-pentyl-3-(1-oxopropyl)-1H-1,2,4-triazol-5-yl]methyl][1,1'-biphenyl]-2-yl]-1H-tetrazole;
5-[4'-[[1-pentyl-3-(1-oxobutyl)-1H-1,2,4-triazol-5-yl]methyl][1,1'-biphenyl]-2-yl]-1H-tetrazole;
5-[4'-[[1-pentyl-3-(1-oxopentyl)-1H-1,2,4-triazol-5-yl]methyl][1,1'-biphenyl]-2-yl]-1H-tetrazole;
5-[4'-[[1-pentyl-3-(1,1-difluoroethyl)-1H-1,2,4-triazol-5-yl]methyl][1,1'-biphenyl]-2-yl]-1H-tetrazole;
5-[4'-[[1-pentyl-3-(1,1-difluoropropyl)-1H-1,2,4-triazol-5-yl]methyl][1,1'-biphenyl]-2-yl]-1H-tetrazole;
5-[4'-[[1-pentyl-3-(1,1-difluorobutyl)-1H-1,2,4-triazol-5-yl]methyl][1,1'-biphenyl]-2-yl]-1H-tetrazole;
5-[4'-[[1-pentyl-3-(1,1-difluoropentyl)-1H-1,2,4-triazol-5-yl]methyl][1,1'-biphenyl]-2-yl]-1H-tetrazole;
5-[4'-[(1-isopentyl-3-ethyl-1H-1,2,4-triazol-5-yl)methyl][1,1'-biphenyl]-2-yl]-1H-tetrazole;
5-[4'-[(1-isopentyl-3-propyl-1H-1,2,4-triazol-5-yl)methyl][1,1'-biphenyl]-2-yl]-1H-tetrazole;
5-[4'-[(1-isopentyl-3-isopropyl-1H-1,2,4-triazol-5-yl)methyl][1,1'-biphenyl]-2-yl]-1H-tetrazole;
5-[4'-[(1-isopentyl-3-butyl-1H-1,2,4-triazol-5-yl)methyl][1,1'-biphenyl]-2-yl]-1H-tetrazole;
5-[4'-[(1-isopentyl-3-secbutyl-1H-1,2,4-triazol-5-yl)methyl][1,1'-biphenyl]-2-yl]-1H-tetrazole;
5-[4'-[(1-isopentyl-3-isobutyl-1H-1,2,4-triazol-5-yl)methyl][1,1'-biphenyl]-2-yl]-1H-tetrazole;
5-[4'-[(1-isopentyl-3-tertbutyl-1H-1,2,4-triazol-5-yl)methyl][1,1'-biphenyl]-2-yl]-1H-tetrazole;
5-[4'-[(1-isopentyl-3-pentyl-1H-1,2,4-triazol-5-yl)methyl][1,1'-biphenyl]-2-yl]-1H-tetrazole;
5-[4'-[(1,3-diisopentyl-1H-1,2,4-triazol-5-yl)methyl][1,1'-biphenyl]-2-yl]-1H-tetrazole;
5-[4'-[(1-isopentyl-3-mercapto-1H-1,2,4-triazol-5-yl)methyl][1,1'-biphenyl]-2-yl]-1H-tetrazole;
5-[4'-[(1-isopentyl-3-thiomethyl-1H-1,2,4-triazol-5-yl)methyl][1,1'-biphenyl]-2-yl]-1H-tetrazole;
5-[4'-[(1-isopentyl-3-thioethyl-1H-1,2,4-triazol-5-yl)methyl][1,1'-biphenyl]-2-yl]-1H-tetrazole;
5-[4'-[(1-isopentyl-3-thiopropyl-1H-1,2,4-triazol-5-yl)methyl][1,1'-biphenyl]-2-yl]-1H-tetrazole;

5-[4'-[(1-isopentyl-3-hydroxy-1H-1,2,4-triazol-5-yl)methyl][1,1'-biphenyl]-2-yl]-1H-tetrazole;
5-[4'-[(1-isopentyl-3-methoxy-1H-1,2,4-triazol-5-yl)methyl][1,1'-biphenyl]-2-yl]-1H-tetrazole;
5-[4'-[(1-isopentyl-3-ethoxy-1H-1,2,4-triazol-5-yl)methyl][1,1'-biphenyl]-2-yl]-1H-tetrazole;
5-[4'-[(1-isopentyl-3-propoxy-1H-1,2,4-triazol-5-yl)methyl][1,1'-biphenyl]-2-yl]-1H-tetrazole;
5-[4'-[(1-isopentyl-3-cyclohexyl-1H-1,2,4-triazol-5-yl)methyl][1,1'-biphenyl]-2-yl]-1H-tetrazole;
5-[4'-[(1-isopentyl-3-cyclohexylmethyl-1H-1,2,4-triazol-5-yl)methyl][1,1'-biphenyl]-2-yl]-1H-tetrazole;
5-[4'-[[1-pentyl-3-(2-cyclohexylethyl)-1H-1,2,4-triazol-5-yl]methyl][1,1'-biphenyl]-2-yl]-1H-tetrazole;
5-[4'-[(1-isopentyl-3-cyclohexanoyl-1H-1,2,4-triazol-5-yl)methyl][1,1'-biphenyl]-2-yl]-1H-tetrazole;
5-[4'-[[1-pentyl-3-(1-oxo-2-cyclohexylethyl)-1H-1,2,4-triazol-5-yl]methyl][1,1'-biphenyl]-2-yl]-1H-tetrazole;
5-[4'-[(1-isopentyl-3-phenyl-1H-1,2,4-triazol-5-yl)methyl][1,1'-biphenyl]-2-yl]-1H-tetrazole;
5-[4'-[(1-isopentyl-3-phenylmethyl-1H-1,2,4-triazol-5-yl)methyl][1,1'-biphenyl]-2-yl]-1H-tetrazole;
5-[4'-[[1-pentyl-3-(2-phenylethyl)-1H-1,2,4-triazol-5-yl]methyl][1,1'-biphenyl]-2-yl]-1H-tetrazole;
5-[4'-[(1-isopentyl-3-benzoyl-1H-1,2,4-triazol-5-yl)methyl][1,1'-biphenyl]-2-yl]-1H-tetrazole;
5-[4'-[[1-isopentyl-3-(1-oxo-2-phenylethyl)-1H-1,2,4-triazol-5-yl]methyl][1,1'-biphenyl]-2-yl]-1H-tetrazole;
5-[4'-[[1-isopentyl-3-(1,1-dimethoxypropyl)-1H-1,2,4-triazol-5-yl]methyl][1,1'-biphenyl]-2-yl]-1H-tetrazole;
5-[4'-[[1-isopentyl-3-(1,1-dimethoxybutyl)-1H-1,2,4-triazol-5-yl]methyl][1,1'-biphenyl]-2-yl]-1H-tetrazole;
5-[4'-[[1-isopentyl-3-(1,1-dimethoxypentyl)-1H-1,2,4-triazol-5-yl]methyl][1,1'-biphenyl]-2-yl]-1H-tetrazole;
5-[4'-[[1-isopentyl-3-(1-oxopropyl)-1H-1,2,4-triazol-5-yl]methyl][1,1'-biphenyl]-2-yl]-1H-tetrazole;
5-[4'-[[1-isopentyl-3-(1-oxobutyl)-1H-1,2,4-triazol-5-yl]methyl][1,1'-biphenyl]-2-yl]-1H-tetrazole;
5-[4'-[[1-isopentyl-3-(1-oxopentyl)-1H-1,2,4-triazol-5-yl]methyl][1,1'-biphenyl]-2-yl]-1H-tetrazole;
5-[4'-[[1-isopentyl-3-(1,1-difluoroethyl)-1H-1,2,4-triazol-5-yl]methyl][1,1'-biphenyl]-2-yl]-1H-tetrazole;
5-[4'-[[1-isopentyl-3-(1,1-difluoropropyl)-1H-1,2,4-triazol-5-yl]methyl][1,1'-biphenyl]-2-yl]-1H-tetrazole;
5-[4'-[[1-isopentyl-3-(1,1-difluorobutyl)-1H-1,2,4-triazol-5-yl]methyl][1,1'-biphenyl]-2-yl]-1H-tetrazole;
5-[4'-[[1-isopentyl-3-(1,1-difluoropentyl)-1H-1,2,4-triazol-5-yl]methyl][1,1'-biphenyl]-2-yl]-1H-tetrazole;
5-[4'-[[1-cyclohexyl-3-ethyl-1H-1,2,4-triazol-5-yl]methyl][1,1'-biphenyl]-2-yl]-1H-tetrazole;
5-[4'-[[1-cyclohexyl-3-propyl-1H-1,2,4-triazol-5-yl]methyl][1,1'-biphenyl]-2-yl]-1H-tetrazole;
5-[4'-[[1-cyclohexyl-3-isopropyl-1H-1,2,4-triazol-5-yl]methyl][1,1'-biphenyl]-2-yl]-1H-tetrazole;
5-[4'-[[1-cyclohexyl-3-butyl-1H-1,2,4-triazol-5-yl]methyl][1,1'-biphenyl]-2-yl]-1H-tetrazole;
5-[4'-[[1-cyclohexyl-3-secbutyl-1H-1,2,4-triazol-5-yl]methyl][1,1'-biphenyl]-2-yl]-1H-tetrazole;
5-[4'-[[1-cyclohexyl-3-isobutyl-1H-1,2,4-triazol-5-yl]methyl][1,1'-biphenyl]-2-yl]-1H-tetrazole;
5-[4'-[[1-cyclohexyl-3-tertbutyl-1H-1,2,4-triazol-5-yl]methyl][1,1'-biphenyl]-2-yl]-1H-tetrazole;
5-[4-[[1-cyclohexyl-3-pentyl-1H-1,2,4-triazol-5-yl]methyl][1,1'-biphenyl]-2-yl]-1H-tetrazole;
5-[4'-[[1-cyclohexyl-3-isopentyl-1H-1,2,4-triazol-5-yl]methyl][1,1'-biphenyl]-2-yl]-1H-tetrazole;
5-[4'-[[1-cyclohexyl-3-mercapto-1H-1,2,4-triazol-5-yl]methyl][1,1'-biphenyl]-2-yl]-1H-tetrazole;
5-[4'-[[1-cyclohexyl-3-thiomethyl-1H-1,2,4-triazol-5-yl]methyl][1,1'-biphenyl]-2-yl]-1H-tetrazole;
5-[4'-[[1-cyclohexyl-3-thioethyl-1H-1,2,4-triazol-5-yl]methyl][1,1'-biphenyl]-2-yl]-1H-tetrazole;
5-[4'-[[1-cyclohexyl-3-thiopropyl-1H-1,2,4-triazol-5-yl]methyl][1,1'-biphenyl]-2-yl]-1H-tetrazole;
5-[4'-[[1-cyclohexyl-3-hydroxy-1H-1,2,4-triazol-5-yl]methyl][1,1'-biphenyl]-2-yl]-1H-tetrazole;
5-[4'-[[1-cyclohexyl-3-methoxy-1H-1,2,4-triazol-5-yl]methyl][1,1'-biphenyl]-2-yl]-1H-tetrazole;
5-[4'-[[1-cyclohexyl-3-ethoxy-1H-1,2,4-triazol-5-yl]methyl][1,1'-biphenyl]-2-yl]-1H-tetrazole;
5-[4'-[[1-cyclohexyl-3-propoxy-1H-1,2,4-triazol-5-yl]methyl][1,1'-biphenyl]-2-yl]-1H-tetrazole;
5-[4'-[[1-cyclohexyl-3-cyclohexyl-1H-1,2,4-triazol-5-yl]methyl][1,1'-biphenyl]-2-yl]-1H-tetrazole;
5-[4'-[[1-cyclohexyl-3-cyclohexylmethyl-1H-1,2,4-triazol-5-yl]methyl][1,1'-biphenyl]-2-yl]-1H-tetrazole;
5-[4'-[[1-cyclohexyl-3-(2-cyclohexylethyl)-1H-1,2,4-triazol-5-yl]methyl][1,1'-biphenyl]-2-yl]-1H-tetrazole;
5-[4'-[[1-cyclohexyl-3-cyclohexanoyl-1H-1,2,4-triazol-5-yl]methyl][1,1'-biphenyl]-2-yl]-1H-tetrazole;
5-[4'-[[1-cyclohexyl-3-(1-oxo-2-cyclohexylethyl)-1H-1,2,4-triazol-5-yl]methyl][1,1'-biphenyl]-2-yl]-1H-tetrazole;
5-[4'-[[1-cyclohexyl-3-phenyl-1H-1,2,4-triazol-5-yl]methyl][1,1'-biphenyl]-2-yl]-1H-tetrazole;
5-[4'-[[1-cyclohexyl-3-phenylmethyl-1H-1,2,4-triazol-5-yl]methyl][1,1'-biphenyl]-2-yl]-1H-tetrazole;
5-[4'-[[1-cyclohexyl-3-(2-phenylethyl)-1H-1,2,4-triazol-5-yl]methyl][1,1'-biphenyl]-2-yl]-1H-tetrazole;
5-[4'-[[1-cyclohexyl-3-benzoyl-1H-1,2,4-triazol-5-yl]methyl][1,1'-biphenyl]-2-yl]-1H-tetrazole;
5-[4'-[[1-cyclohexyl-3-(1-oxo-2-phenylethyl)-1H-1,2,4-triazol-5-yl]methyl][1,1'-biphenyl]-2-yl]-1H-tetrazole;
5-[4'-[[1-cyclohexyl-3-(1,1-dimethoxypropyl)-1H-1,2,4-triazol-5-yl]methyl][1,1'-biphenyl]-2-yl]-1H-tetrazole;
5-[4'-[[1-cyclohexyl-3-(1,1-dimethoxybutyl)-1H-1,2,4-triazol-5-yl]methyl][1,1'-biphenyl]-2-yl]-1H-tetrazole;
5-[4'-[[1-cyclohexyl-3-(1,1-dimethoxypentyl)-1H-1,2,4-triazol-5-yl]methyl][1,1'-biphenyl]-2-yl]-1H-tetrazole;
5-[4'-[[1-cyclohexyl-3-(1-oxopropyl)-1H-1,2,4-triazol-5-yl]methyl][1,1'-biphenyl]-2-yl]-1H-tetrazole;
5-[4'-[[1-cyclohexyl-3-(1-oxobutyl)-1H-1,2,4-triazol-5-yl]methyl][1,1'-biphenyl]-2-yl]-1H-tetrazole;
5-[4'-[[1-cyclohexyl-3-(1-oxopentyl)-1H-1,2,4-triazol-5-yl]methyl][1,1'-biphenyl]-2-yl]-1H-tetrazole;
5-[4'-[[1-cyclohexyl-3-(1,1-difluoroethyl)-1H-1,2,4-triazol-5-yl]methyl][1,1'-biphenyl]-2-yl]-1H-tetrazole;
5-[4'-[[1-cyclohexyl-3-(1,1-difluoropropyl)-1H-1,2,4-triazol-5-yl]methyl][1,1'-biphenyl]-2-yl]-1H-tetrazole;
5-[4'-[[1-cyclohexyl-3-(1,1-difluorobutyl)-1H-1,2,4-triazol-5-yl]methyl][1,1'-biphenyl]-2-yl]-1H-tetrazole;
5-[4'-[[1-cyclohexyl-3-(1,1-difluoropentyl)-1H-1,2,4-triazol-5-yl]methyl][1,1'-biphenyl]-2-yl]-1H-tetrazole;
5-[4'-[[1-(2-butenyl)-3-ethyl-1H-1,2,4-triazol-5-yl]methyl][1,1'-biphenyl]-2-yl]-1H-tetrazole;
5-[4'-[[1-(2-butenyl)-3-propyl-1H-1,2,4-triazol-5-yl]methyl][1,1'-biphenyl]-2-yl]-1H-tetrazole;
5-[4'-[[1-(2-butenyl)-3-isopropyl-1H-1,2,4-triazol-5-yl]methyl][1,1'-biphenyl]-2-yl]-1H-tetrazole;
5-[4'-[[1-(2-butenyl)-3-butyl-1H-1,2,4-triazol-5-yl]methyl][1,1'-biphenyl]-2-yl]-1H-tetrazole;
5-[4'-[[1-(2-butenyl)-3-secbutyl-1H-1,2,4-triazol-5-yl]methyl][1,1'-biphenyl]-2-yl]-1H-tetrazole;
5-[4'-[[1-(2-butenyl)-3-isobutyl-1H-1,2,4-triazol-5-yl]methyl][1,1'-biphenyl]-2-yl]-1H-tetrazole;

5-[4'-[[1-(2-butenyl)-3-tertbutyl-1H-1,2,4-triazol-5-yl]methyl][1,1'-biphenyl]-2-yl]-1H-tetrazole;
5-[4'-[[1-(2-butenyl)-3-pentyl-1H-1,2,4-triazol-5-yl]methyl][1,1'-biphenyl]-2-yl]-1H-tetrazole;
5-[4'-[[1-(2-butenyl)-3-isopentyl-1H-1,2,4-triazol-5-yl]methyl][1,1'-biphenyl]-2-yl]-1H-tetrazole;
5-[4'-[[1-(2-butenyl)-3-mercapto-1H-1,2,4-triazol-5-yl]methyl][1,1'-biphenyl]-2-yl]-1H-tetrazole;
5-[4'-[[1-(2-butenyl)-3-thiomethyl-1H-1,2,4-triazol-5-yl]methyl][1,1'-biphenyl]-2-yl]-1H-tetrazole;
5-[4'-[[1-(2-butenyl)-3-thioethyl-1H-1,2,4-triazol-5-yl]methyl][1,1'-biphenyl]-2-yl]-1H-tetrazole;
5-[4'-[[1-(2-butenyl)-3-thiopropyl-1H-1,2,4-triazol-5-yl]methyl][1,1'-biphenyl]-2-yl]-1H-tetrazole;
5-[4'-[[1-(2-butenyl)-3-hydroxy-1H-1,2,4-triazol-5-yl]methyl][1,1'-biphenyl]-2-yl]-1H-tetrazole;
5-[4'-[[1-(2-butenyl)-3-methoxy-1H-1,2,4-triazol-5-yl]methyl][1,1'-biphenyl]-2-yl]-1H-tetrazole;
5-[4'-[[1-(2-butenyl)-3-ethoxy-1H-1,2,4-triazol-5-yl]methyl][1,1'-biphenyl]-2-yl]-1H-tetrazole;
5-[4'-[[1-(2-butenyl)-3-propoxy-1H-1,2,4-triazol-5-yl]methyl][1,1'-biphenyl]-2-yl]-1H-tetrazole;
5-[4'-[[1-(2-butenyl)-3-cyclohexyl-1H-1,2,4-triazol-5-yl]methyl][1,1'-biphenyl]-2-yl]-1H-tetrazole;
5-[4'-[[1-(2-butenyl)-3-cyclohexylmethyl-1H-1,2,4-triazol-5-yl]methyl][1,1'-biphenyl]-2-yl]-1H-tetrazole;
5-[4'-[[1-(2-butenyl)-3-(2-cyclohexylethyl)-1H-1,2,4-triazol-5-yl]methyl][1,1'-biphenyl]-2-yl]-1H-tetrazole;
5-[4'-[[1-(2-butenyl)-3-cyclohexanoyl-1H-1,2,4-triazol-5-yl]methyl][1,1'-biphenyl]-2-yl]-1H-tetrazole;
5-[4'-[[1-(2-butenyl)-3-(1-oxo-2-cyclohexylethyl)-1H-1,2,4-triazol-5-yl]methyl][1,1'-biphenyl]-2-yl]-1H-tetrazole;
5-[4'-[[1-(2-butenyl)-3-phenyl-1H-1,2,4-triazol-5-yl]methyl][1,1'-biphenyl]-2-yl]-1H-tetrazole;
5-[4'-[[1-(2-butenyl)-3-phenylmethyl-1H-1,2,4-triazol-5-yl]methyl][1,1'-biphenyl]-2-yl]-1H-tetrazole;
5-[4 -[[1-(2-butenyl)-3-(2-phenylethyl)-1H-1,2,4-triazol-5-yl]methyl][1,1'-biphenyl]-2-yl]-1H-tetrazole;
5-[4,-[[1-(2-butenyl)-3-(1,1-dimethoxypropyl)-1H-1,2,4-triazol-5-yl]methyl][1,1'-biphenyl]-2-yl]-1H-tetrazole;
5-[4'-[[1-(2-butenyl)-3-(1,1-dimethoxybutyl)-1H-1,2,4-triazol-5-yl]methyl][1,1'-biphenyl]-2-yl]-1H-tetrazole;
5-[4'-[[1-(2-butenyl)-3-(1,1-dimethoxypentyl)-1H-1,2,4-triazol-5-yl]methyl][1,1'-biphenyl]-2-yl]-1H-tetrazole;
5-[4'-[[1-(2-butenyl)-3-(1-oxopropyl)-1H-1,2,4-triazol-5-yl]methyl][1,1'-biphenyl]-2-yl]-1H-tetrazole;
5-[4'-[[1-(2-butenyl)-3-(1-oxobutyl)-1H-1,2,4-triazol-5-yl]methyl][1,1'-biphenyl]-2-yl]-1H-tetrazole;
5-[4'-[[1-(2-butenyl)-3-(1-oxopentyl)-1H-1,2,4-triazol-5-yl]methyl][1,1'-biphenyl]-2-yl]-1H-tetrazole;
5-[4'-[[1-(2-butenyl)-3-(1,1-difluoroethyl)-1H-1,2,4-triazol-5-yl]methyl][1,1'-biphenyl]-2-yl]-1H-tetrazole;
5-[4'-[[1-(2-butenyl)-3-(1,1-difluoropropyl)-1H-1,2,4-triazol-5-yl]methyl][1,1'-biphenyl]-2-yl]-1H-tetrazole;
5-[4'-[[1-(2-butenyl)-3-(1,1-difluorobutyl)-1H-1,2,4-triazol-5-yl]methyl][1,1'-biphenyl]-2-yl]-1H-tetrazole;
5-[4'-[[1-(2-butenyl)-3-(1,1-difluoropentyl)-1H-1,2,4-triazol-5-yl]methyl][1,1'-biphenyl]-2-yl]-1H-tetrazole;
5-[4'-[[1-(3-butenyl)-3-ethyl-1H-1,2,4-triazol-5-yl]methyl][1,1'-biphenyl]-2-yl]-1H-tetrazole;
5-[4'-[[1-(3-butenyl)-3-propyl-1H-1,2,4-triazol-5-yl]methyl][1,1'-biphenyl]-2-yl]-1H-tetrazole;
5-[4'-[[1-(3-butenyl)-3-isopropyl-1H-1,2,4-triazol-5-yl]methyl][1,1'-biphenyl]-2-yl]-1H-tetrazole;
5-[4'-[[1-(3-butenyl)-3-butyl-1H-1,2,4-triazol-5-yl]methyl][1,1'-biphenyl]-2-yl]-1H-tetrazole;
5-[4'-[[1-(3-butenyl)-3-secbutyl-1H-1,2,4-triazol-5-yl]methyl][1,1'-biphenyl]-2-yl]-1H-tetrazole;
5-[4'-[[1-(3-butenyl)-3-isobutyl-1H-1,2,4-triazol-5-yl]methyl][1,1'-biphenyl]-2-yl]-1H-tetrazole;
5-[4'-[[1-(3-butenyl)-3-tertbutyl-1H-1,2,4-triazol-5-yl]methyl][1,1'-biphenyl]-2-yl]-1H-tetrazole;
5-[4'-[[1-(3-butenyl)-3-pentyl-1H-1,2,4-triazol-5-yl]methyl][1,1'-biphenyl]-2-yl]-1H-tetrazole;
5-[4'-[[1-(3-butenyl)-3-isopentyl-1H-1,2,4-triazol-5-yl]methyl][1,1'-biphenyl]-2-yl]-1H-tetrazole;
5-[4'-[[1-(3-butenyl)-3-mercapto-1H-1,2,4-triazol-5-yl]methyl][1,1'-biphenyl]-2-yl]-1H-tetrazole;
5-[4'-[[1-(3-butenyl)-3-thiomethyl-1H-1,2,4-triazol-5-yl]methyl][1,1'-biphenyl]-2-yl]-1H-tetrazole;
5-[4'-[[1-(3-butenyl)-3-thioethyl-1H-1,2,4-triazol-5-yl]methyl][1,1'-biphenyl]-2-yl]-1H-tetrazole;
5-[4'-[[1-(3-butenyl)-3-thiopropyl-1H-1,2,4-triazol-5-yl]methyl][1,1'-biphenyl]-2-yl]-1H-tetrazole;
5-[4'-[[1-(3-butenyl)-3-hydroxy-1H-1,2,4-triazol-5-yl]methyl][1,1'-biphenyl]-2-yl]-1H-tetrazole;
5-[4'-[[1-(3-butenyl)-3-methoxy-1H-1,2,4-triazol-5-yl]methyl][1,1'-biphenyl]-2-yl]-1H-tetrazole;
5-[4'-[[1-(3-butenyl)-3-ethoxy-1H-1,2,4-triazol-5-yl]methyl][1,1'-biphenyl]-2-yl]-1H-tetrazole;
5-[4'-[[1-(3-butenyl)-3-propoxy-1H-1,2,4-triazol-5-yl]methyl][1,1'-biphenyl]-2-yl]-1H-tetrazole;
5-[4'-[[1-(3-butenyl)-3-cyclohexyl-1H-1,2,4-triazol-5-yl]methyl][1,1'-biphenyl]-2-yl]-1H-tetrazole;
5-[4'-[[1-(3-butenyl)-3-cyclohexylmethyl-1H-1,2,4-triazol-5-yl]methyl][1,1'-biphenyl]-2-yl]-1H-tetrazole;
5-[4'-[[1-(3-butenyl)-3-(2-cyclohexylethyl)-1H-1,2,4-triazol-5-yl]methyl][1,1'-biphenyl]-2-yl]-1H-tetrazole;
5-[4'-[[1-(3-butenyl)-3-cyclohexanoyl-1H-1,2,4-triazol-5-yl]methyl][1,1'-biphenyl]-2-yl]-1H-tetrazole;
5-[4'-[[1-(3-butenyl)-3-(1-oxo-2-cyclohexylethyl)-1H-1,2,4-triazol-5-yl]methyl][1,1'-biphenyl]-2-yl]-1H-tetrazole;
5-[4'-[[1-(3-butenyl)-3-phenyl-1H-1,2,4-triazol-5-yl]methyl][1,1'-biphenyl]-2-yl]-1H-tetrazole;
5-[4'-[[1-(3-butenyl)-3-phenylmethyl-1H-1,2,4-triazol-5-yl]methyl][1,1'-biphenyl]-2-yl]-1H-tetrazole;
5-[4'-[[1-(3-butenyl)-3-(2-phenylethyl)-1H-1,2,4-triazol-5-yl]methyl][1,1'-biphenyl]-2-yl]-1H-tetrazole;
5-[4'-[[1-(3-butenyl)-3-benzoyl-1H-1,2,4-triazol-5-yl]methyl][1,1'-biphenyl]-2-yl]-1H-tetrazole;
5-[4'-[[1-(3-butenyl)-3-(1-oxo-2-phenylethyl)-1H-1,2,4-triazol-5-yl]methyl][1,1'-biphenyl]-2-yl]-1H-tetrazole;
5-[4'-[[1-(3-butenyl)-3-(1,1-dimethoxypropyl)-1H-1,2,4-triazol-5-yl]methyl][1,1'-biphenyl]-2-yl]-1H-tetrazole;
5-[4'-[[1-(3-butenyl)-3-(1,1-dimethoxybutyl)-1H-1,2,4-triazol-5-yl]methyl][1,1'-biphenyl]-2-yl]-1H-tetrazole;
5-[4'-[[1-(3-butenyl)-3-(1,1-dimethoxypentyl)-1H-1,2,4-triazol-5-yl]methyl][1,1'-biphenyl]-2-yl]-1H-tetrazole;
5-[4'-[[1-(3-butenyl)-3-(1-oxopropyl)-1H-1,2,4-triazol-5-yl]methyl][1,1'-biphenyl]-2-yl]-1H-tetrazole;
5-[4'-[[1-(3-butenyl)-3-(1-oxobutyl)-1H-1,2,4-triazol-5-yl]methyl][1,1'-biphenyl]-2-yl]-1H-tetrazole;
5-[4'-[[1-(3-butenyl)-3-(1-oxopentyl)-1H-1,2,4-triazol-5-yl]methyl][1,1'-biphenyl]-2-yl]-1H-tetrazole;
5-[4'-[[1-(3-butenyl)-3-(1,1-difluoroethyl)-1H-1,2,4-triazol-5-yl]methyl][1,1'-biphenyl]-2-yl]-1H-tetrazole;
5-[4'-[[1-(3-butenyl)-3-(1,1-difluoropropyl)-1H-1,2,4-triazol-5-yl]methyl][1,1'-biphenyl]-2-yl]-1H-tetrazole;
5-[4'-[[1-(3-butenyl)-3-(1,1-difluorobutyl)-1H-1,2,4-triazol-5-yl]methyl][1,1'-biphenyl]-2-yl]-1H-tetrazole;
5-[4'-[[1-(3-butenyl)-3-(1,1-difluoropentyl)-1H-1,2,4-triazol-5-yl]methyl][1,1'-biphenyl]-2-yl]-1H-tetrazole;

5-[4'-[[1-hexyl-3-ethyl-1H-1,2,4-triazol-5-yl]methyl][1,1'-biphenyl]-2-yl]-1H-tetrazole;
5-[4'-[[1-hexyl-3-propyl-1H-1,2,4-triazol-5-yl]methyl][1,1'-biphenyl]-2-yl]-1H-tetrazole;
5-[4'-[[1-hexyl-3-butyl-1H-1,2,4-triazol-5-yl]methyl][1,1'-biphenyl]-2-yl]-1H-tetrazole;
5-[4'-[[1-hexyl-3-secbutyl-1H-1,2,4-triazol-5-yl]methyl][1,1'-biphenyl]-2-yl]-1H-tetrazole;
5-[4'-[[1-hexyl-3-isobutyl-1H-1,2,4-triazol-5-yl]methyl][1,1'-biphenyl]-2-yl]-1H-tetrazole;
5-[4'-[[1-hexyl-3-tertbutyl-1H-1,2,4-triazol-5-yl]methyl][1,1'-biphenyl]-2-yl]-1H-tetrazole;
5-[4'-[[1-hexyl-3-pentyl-1H-1,2,4-triazol-5-yl]methyl][1,1'-biphenyl]-2-yl]-1H-tetrazole;
5-[4'-[[1-hexyl-3-isopentyl-1H-1,2,4-triazol-5-yl]methyl][1,1'-biphenyl]-2-yl]-1H-tetrazole;
5-[4'-[[1-hexyl-3-mercapto-1H-1,2,4-triazol-5-yl]methyl][1,1'-biphenyl]-2-yl]-1H-tetrazole;
5-[4'-[[1-hexyl-3-thiomethyl-1H-1,2,4-triazol-5-yl]methyl][1,1'-biphenyl]-2-yl]-1H-tetrazole;
5-[4'-[[1-hexyl-3-thioethyl-1H-1,2,4-triazol-5-yl]methyl][1,1'-biphenyl]-2-yl]-1H-tetrazole;
5-[4'-[[1-hexyl-3-thiopropyl-1H-1,2,4-triazol-5-yl]methyl][1,1'-biphenyl]-2-yl]-1H-tetrazole;
5-[4'-[[1-hexyl-3-hydroxy-1H-1,2,4-triazol-5-yl]methyl][1,1,-biphenyl]-2-yl]-1H-tetrazole;
5-[4'-[[1-hexyl-3-methoxy-1H-1,2,4-triazol-5-yl]methyl][1,1'-biphenyl]-2-yl]-1H-tetrazole;
5-[4'-[[1-hexyl-3-ethoxy-1H-1,2,4-triazol-5-yl]methyl][1,1'-biphenyl]-2-yl]-1H-tetrazole;
5-[4'-[[1-hexyl-3-propoxy-1H-1,2,4-triazol-5-yl]methyl][1,1'-biphenyl]-2-yl]-1H-tetrazole;
5-[4'-[[1-hexyl-3-cyclohexyl-1H-1,2,4-triazol-5-yl]methyl][1,1'-biphenyl]-2-yl]-1H-tetrazole;
5-[4'-[[1-hexyl-3-cyclohexylmethyl-1H-1,2,4-triazol-5-yl]methyl][1,1'-biphenyl]-2-yl]-1H-tetrazole;
5-[4'-[[1-hexyl-3-(2-cyclohexylethyl)-1H-1,2,4-triazol-5-yl]methyl][1,1'-biphenyl]-2-yl]-1H-tetrazole;
5-[4'-[[1-hexyl-3-cyclohexanoyl-1H-1,2,4-triazol-5-yl]methyl][1,1'-biphenyl]-2-yl]-1H-tetrazole;
5-[4'-[[1-hexyl-3-(1-oxo-2-cyclohexylethyl)-1H-1,2,4-triazol-5-yl]methyl][1,1'-biphenyl]-2-yl]-1H-tetrazole;
5-[4'-[[1-hexyl-3-phenyl-1H-1,2,4-triazol-5-yl]methyl][1,1'-biphenyl]-2-yl]-1H-tetrazole;
5-[4'-[[1-hexyl-3-phenylmethyl-1H-1,2,4-triazol-5-yl]methyl][1,1'-biphenyl]-2-yl]-1H-tetrazole;
5-[4'-[[1-hexyl-3-(2-phenylethyl)-1H-1,2,4-triazol-5-yl]methyl][1,1'-biphenyl]-2-yl]-1H-tetrazole;
5-[4'-[[1-hexyl-3-benzoyl-1H-1,2,4-triazol-5-yl]methyl][1,1'-biphenyl]-2-yl]-1H-tetrazole;
5-[4'-[[1-hexyl-3-(1-oxo-2-phenylethyl)-1H-1,2,4-triazol-5-yl]methyl][1,1'-biphenyl]-2-yl]-1H-tetrazole;
5-[4'-[[1-hexyl-3-(1,1-dimethoxypropyl)-1H-1,2,4-triazol-5-yl]methyl][1,1'-biphenyl]-2-yl]-1H-tetrazole;
5-[4'-[[1-hexyl-3-(1,1-dimethoxybutyl)-1H-1,2,4-triazol-5-yl]methyl][1,1'-biphenyl]-2-yl]-1H-tetrazole;
5-[4'-[[1-hexyl-3-(1,1-dimethoxypentyl)-1H-1,2,4-triazol-5-yl]methyl][1,1'-biphenyl]-2-yl]-1H-tetrazole;
5-[4'-[[1-hexyl-3-(1-oxopropyl)-1H-1,2,4-triazol-5-yl]methyl][1,1'-biphenyl]-2-yl]-1H-tetrazole;
5-[4'-[[1-hexyl-3-(1-oxobutyl)-1H-1,2,4-triazol-5-yl]methyl][1,1'-biphenyl]-2-yl]-1H-tetrazole;
5-[4'-[[1-hexyl-3-(1-oxopentyl)-1H-1,2,4-triazol-5-yl]methyl][1,1'-biphenyl]-2-yl]-1H-tetrazole;
5-[4'-[[1-hexyl-3-(1,1-difluoroethyl)-1H-1,2,4-triazol-5-yl]methyl][1,1'-biphenyl]-2-yl]-1H-tetrazole;
5-[4'-[[1-hexyl-3-(1,1-difluoropropyl)-1H-1,2,4-triazol-5-yl]methyl][1,1'-biphenyl]-2-yl]-1H-tetrazole;
5-[4'-[[1-hexyl-3-(1,1-difluorobutyl)-1H-1,2,4-triazol-5-yl]methyl][1,1'-biphenyl]-2-yl]-1H-tetrazole;
5-[4'-[[1-hexyl-3-(1,1-difluoropentyl)-1H-1,2,4-triazol-5-yl]methyl][1,1'-biphenyl]-2-yl]-1H-tetrazole;
5-[4'-[[1-(2-butynyl)-3-ethyl-1H-1,2,4-triazol-5-yl]methyl][1,1'-biphenyl]-2-yl]-1H-tetrazole;
5-[4'-[[1-(2-butynyl)-3-propyl-1H-1,2,4-triazol-5-yl]methyl][1,1'-biphenyl]-2-yl]-1H-tetrazole;
5-[4'-[[1-(2-butynyl)-3-butyl-1H-1,2,4-triazol-5-yl]methyl][1,1'-biphenyl]-2-yl]-1H-tetrazole;
5-[4'-[[1-(2-butynyl)-3-secbutyl-1H-1,2,4-triazol-5-yl]methyl][1,1'-biphenyl]-2-yl]-1H-tetrazole;
5-[4'-[[1-(2-butynyl)-3-isobutyl-1H-1,2,4-triazol-5-yl]methyl][1,1'-biphenyl]-2-yl]-1H-tetrazole;
5-[4'-[[1-(2-butynyl)-3-tertbutyl-1H-1,2,4-triazol-5-yl]methyl][1,1'-biphenyl]-2-yl]-1H-tetrazole;
5-[4'-[[1-(2-butynyl)-3-pentyl-1H-1,2,4-triazol-5-yl]methyl][1,1'-biphenyl]-2-yl]-1H-tetrazole;
5-[4'-[[1-(2-butynyl)-3-isopentyl-1H-1,2,4-triazol-5-yl]methyl][1,1'-biphenyl]-2-yl]-1H-tetrazole;
5-[4'-[[1-(2-butynyl)-3-mercapto-1H-1,2,4-triazol-5-yl]methyl][1,1'-biphenyl]-2-yl]-1H-tetrazole;
5-[4'-[[1-(2-butynyl)-3-thiomethyl-1H-1,2,4-triazol-5-yl]methyl][1,1'-biphenyl]-2-yl]-1H-tetrazole;
5-[4'-[[1-(2-butynyl)-3-thioethyl-1H-1,2,4-triazol-5-yl]methyl][1,1'-biphenyl]-2-yl]-1H-tetrazole;
5-[4'-[[1-(2-butynyl)-3-thiopropyl-1H-1,2,4-triazol-5-yl]methyl][1,1'-biphenyl]-2-yl]-1H-tetrazole;
5-[4'-[[1-(2-butynyl)-3-hydroxy-1H-1,2,4-triazol-5-yl]methyl][1,1'-biphenyl]-2-yl]-1H-tetrazole;
5-[4'-[[1-(2-butynyl)-3-methoxy-1H-1,2,4-triazol-5-yl]methyl][1,1'-biphenyl]-2-yl]-1H-tetrazole;
5-[4'-[[1-(2-butynyl)-3-ethoxy-1H-1,2,4-triazol-5-yl]methyl][1,1'-biphenyl]-2-yl]-1H-tetrazole;
5-[4'-[[1-(2-butynyl)-3-propoxy-1H-1,2,4-triazol-5-yl]methyl][1,1'-biphenyl]-2-yl]-1H-tetrazole;
5-[4'-[[1-(2-butynyl)-3-cyclohexyl-1H-1,2,4-triazol-5-yl]methyl][1,1'-biphenyl]-2-yl]-1H-tetrazole;
5-[4'-[[1-(2-butynyl)-3-cyclohexylmethyl-1H-1,2,4-triazol-5-yl]methyl][1,1'-biphenyl]-2-yl]-1H-tetrazole;
5-[4'-[[1-(2-butynyl)-3-(2-cyclohexylethyl)-1H-1,2,4-triazol-5-yl]methyl][1,1'-biphenyl]-2-yl]-1H-tetrazole;
5-[4'-[[1-(2-butynyl)-3-cyclohexanoyl-1H-1,2,4-triazol-5-yl]methyl][1,1'-biphenyl]-2-yl]-1H-tetrazole;
5-[4'-[[1-(2-butynyl)-3-(1-oxo-2-cyclohexylethyl)-1H-1,2,4-triazol-5-yl]methyl][1,1'-biphenyl]-2-yl]-1H-tetrazole;
5-[4'-[[1-(2-butynyl)-3-phenyl-1H-1,2,4-triazol-5-yl]methyl][1,1'-biphenyl]-2-yl]-1H-tetrazole;
5-[4'-[[1-(2-butynyl)-3-phenylmethyl-1H-1,2,4-triazol-5-yl]methyl][1,1'-biphenyl]-2-yl]-1H-tetrazole;
5-[4'-[[1-(2-butynyl)-3-(2-phenylethyl)-1H-1,2,4-triazol-5-yl]methyl][1,1'-biphenyl]-2-yl]-1H-tetrazole;
5-[4'-[[1-(2-butynyl)-3-benzoyl-1H-1,2,4-triazol-5-yl]methyl][1,1'-biphenyl]-2-yl]-1H-tetrazole;
5-[4'-[[1-(2-butynyl)-3-(1-oxo-2-phenylethyl)-1H-1,2,4-triazol-5-yl]methyl][1,1'-biphenyl]-2-yl]-1H-tetrazole;
5-[4'-[[1-(2-butynyl)-3-(1,1-dimethoxypropyl)-1H-1,2,4-triazol-5-yl]methyl][1,1'-biphenyl]-2-yl]-1H-tetrazole;
5-[4'-[[1-(2-butynyl)-3-(1,1-dimethoxybutyl)-1H-1,2,4-triazol-5-yl]methyl][1,1'-biphenyl]-2-yl]-1H-tetrazole;
5-[4'-[[1-(2-butynyl)-3-(1,1-dimethoxypentyl)-1H-1,2,4-triazol-5-yl]methyl][1,1'-biphenyl]-2-yl]-1H-tetrazole;
5-[4'-[[1-(2-butynyl)-3-(1-oxopropyl)-1H-1,2,4-triazol-5-yl]methyl][1,1'-biphenyl]-2-yl]-1H-tetrazole;
5-[4'-[[1-(2-butynyl)-3-(1-oxobutyl)-1H-1,2,4-triazol-5-yl]methyl][1,1'-biphenyl]-2-yl]-1H-tetrazole;

5-[4'-[[1-(2-butynyl)-3-(1-oxopentyl)-1H-1,2,4-triazol-5-yl]methyl][1,1'-biphenyl]-2-yl]-1H-tetrazole;
5-[4'-[[1-(2-butynyl)-3-(1,1-difluoroethyl)-1H-1,2,4-triazol-5-yl]methyl][1,1'-biphenyl]-2-yl]-1H-tetrazole;
5-[4'-[[1-(2-butynyl)-3-(1,1-difluoropropyl)-1H-1,2,4-triazol-5-yl]methyl][1,1'-biphenyl]-2-yl]-1H-tetrazole;
5-[4'-[[1-(2-butynyl)-3-(1,1-difluorobutyl)-1H-1,2,4-triazol-5-yl]methyl][1,1'-biphenyl]-2-yl]-1H-tetrazole;
5-[4'-[[1-(2-butynyl)-3-(1,1-difluoropentyl)-1H-1,2,4-triazol-5-yl]methyl][1,1'-biphenyl]-2-yl]-1H-tetrazole;
5-[4'-[[1-(3-butynyl)-3-ethyl-1H-1,2,4-triazol-5-yl]methyl][1,1'-biphenyl]-2-yl]-1H-tetrazole;
5-[4'-[[1-(3-butynyl)-3-propyl-1H-1,2,4-triazol-5-yl]methyl][1,1'-biphenyl]-2-yl]-1H-tetrazole;
5-[4'-[[1-(3-butynyl)-3-isopropyl-1H-1,2,4-triazol-5-yl]methyl][1,1'-biphenyl]-2-yl]-1H-tetrazole;
5-[4'-[[1-(3-butynyl)-3-butyl-1H-1,2,4-triazol-5-yl]methyl][1,1'-biphenyl]-2-yl]-1H-tetrazole;
5-[4'-[[1-(3-butynyl)-3-secbutyl-1H-1,2,4-triazol-5-yl]methyl][1,1'-biphenyl]-2-yl]-1H-tetrazole;
5-[4'-[[1-(3-butynyl)-3-isobutyl-1H-1,2,4-triazol-5-yl]methyl][1,1'-biphenyl]-2-yl]-1H-tetrazole;
5-[4'-[[1-(3-butynyl)-3-tertbutyl-1H-1,2,4-triazol-5-yl]methyl][1,1'-biphenyl]-2-yl]-1H-tetrazole;
5-[4'-[[1-(3-butynyl)-3-isopentyl-1H-1,2,4-triazol-5-yl]methyl][1,1'-biphenyl]-2-yl]-1H-tetrazole;
5-[4'-[[1-(3-butynyl)-3-pentyl-1H-1,2,4-triazol-5-yl]methyl][1,1'-biphenyl]-2-yl]-1H-tetrazole;
5-[4'-[[1-(3-butynyl)-3-mercapto-1H-1,2,4-triazol-5-yl]methyl][1,1'-biphenyl]-2-yl]-1H-tetrazole;
5-[4'-[[1-(3-butynyl)-3-thiomethyl-1H-1,2,4-triazol-5-yl]methyl][1,1'-biphenyl]-2-yl]-1H-tetrazole;
5-[4'-[[1-(3-butynyl)-3-thioethyl-1H-1,2,4-triazol-5-yl]methyl][1,1'-biphenyl]-2-yl]-1H-tetrazole;
5-[4'-[[1-(3-butynyl)-3-thiopropyl-1H-1,2,4-triazol-5-yl]methyl][1,1'-biphenyl]-2-yl]-1H-tetrazole;
5-[4'-[[1-(3-butynyl)-3-hydroxy-1H-1,2,4-triazol-5-yl]methyl][1,1'-biphenyl]-2-yl]-1H-tetrazole;
5-[4'-((1-(3-butynyl)-3-methoxy-1H-1,2,4-triazol-5-yl]methyl][1,1'-biphenyl]-2-yl]-1H-tetrazole;
5-[4'-[[1-(3-butynyl)-3-ethoxy-1H-1,2,4-triazol-5-yl]methyl][1,1'-biphenyl]-2-yl]-1H-tetrazole;
5-[4'-[[1-(3-butynyl)-3-propoxy-1H-1,2,4-triazol-5-yl]methyl][1,1'-biphenyl]-2-yl]-1H-tetrazole;
5-[4'-[[1-(3-butynyl)-3-cyclohexyl-1H-1,2,4-triazol-5-yl]methyl][1,1'-biphenyl]-2-yl]-1H-tetrazole;
5-[4- [[1-(3-butynyl)-3-cyclohexylmethyl-1H-1,2,4-triazol-5-yl]methyl][1,1'-biphenyl]-2-yl]-1H-tetrazole;
5-[4'-[[1-(3-butynyl)-3-(2-cyclohexylethyl)-1H-1,2,4-triazol-5-yl]methyl][1,1'-biphenyl]-2-yl]-1H-tetrazole;
5-[4'-[[1-(3-butynyl)-3-cyclohexanoyl-1H-1,2,4-triazol-5-yl]methyl][1,1'-biphenyl]-2-yl]-1H-tetrazole;
5-[4'-[[1-(3-butynyl)-3-(1-oxo-2-cyclohexylethyl)-1H-1,2,4-triazol-5-yl]methyl][1,1'-biphenyl]-2-yl]-1H-tetrazole;
5-[4'-[[1-(3-butynyl)-3-phenyl-1H-1,2,4-triazol-5-yl]methyl][1,1'-biphenyl]-2-yl]-1H-tetrazole;
5-[4'-[[1-(3-butynyl)-3-phenylmethyl-1H-1,2,4-triazol-5-yl]methyl][1,1'-biphenyl]-2-yl]-1H-tetrazole;
5-[4'-[[1-(3-butynyl)-3-(2-phenylethyl)-1H-1,2,4-triazol-5-yl]methyl][1,1'-biphenyl]-2-yl]-1H-tetrazole;
5-[4'-[[1-(3-butynyl)-3-benzoyl-1H-1,2,4-triazol-5-yl]methyl][1,1'-biphenyl]-2-yl]-1H-tetrazole;
5-[4'-[[1-(3-butynyl)-3-(1-oxo-2-phenylethyl)-1H-1,2,4-triazol-5-yl]methyl][1,1'-biphenyl]-2-yl]-1H-tetrazole;
5-[4'-[[1-(3-butynyl)-3-(1,1-dimethoxypropyl)-1H-1,2,4-triazol-5-yl]methyl][1,1'-biphenyl]-2-yl]-1H-tetrazole;
5-[4'-[[1-(3-butynyl)-3-(1,1-dimethoxybutyl)-1H-1,2,4-triazol-5-yl]methyl][1,1'-biphenyl]-2-yl]-1H-tetrazole;
5-[4'-[[1-(3-butynyl)-3-(1,1-dimethoxypentyl)-1H-1,2,4-triazol-5-yl]methyl][1,1'-biphenyl]-2-yl]-1H-tetrazole;
5-[4'-[[1-(3-butynyl)-3-(1-oxopropyl)-1H-1,2,4-triazol-5-yl]methyl][1,1'-biphenyl]-2-yl]-1H-tetrazole;
5-[4'-[[1-(3-butynyl)-3-(1-oxobutyl)-1H-1,2,4-triazol-5-yl]methyl][1,1'-biphenyl]-2-yl]-1H-tetrazole;
5-[4'-[[1-(3-butynyl)-3-(1-oxopentyl)-1H-1,2,4-triazol-5-yl]methyl][1,1'-biphenyl]-2-yl]-1H-tetrazole;
5-[4'-[[1-(3-butynyl)-3-(1,1-difluoroethyl)-1H-1,2,4-triazol-5-yl]methyl][1,1'-biphenyl]-2-yl]-1H-tetrazole;
5-[4'-[[1-(3-butynyl)-3-(1,1-difluoropropyl)-1H-1,2,4-triazol-5-yl]methyl][1,1'-biphenyl]-2-yl]-1H-tetrazole;
5-[4'-[[1-(3-butynyl)-3-(1,1-difluorobutyl)-1H-1,2,4-triazol-5-yl]methyl][1,1'-biphenyl]-2-yl]-1H-tetrazole;
5-[4'-[[1-(3-butynyl)-3-(1,1-difluoropentyl)-1H-1,2,4-triazol-5-yl]methyl][1,1'-biphenyl]-2-yl]-1H-tetrazole;
5-[4'-[(1-cyclohexyl-3-ethoxy-1H-1,2,4-triazol-5-yl)methyl][1,1'-biphenyl]-2-yl]-1H-tetrazole;
5-[4'-[(1-cyclohexyl-3-propoxy-1H-1,2,4-triazol-5-yl)methyl][1,1'-biphenyl]-2-yl]-1H-tetrazole;
5-[4'-[(1-cyclohexyl-3-isopropyl-1H-1,2,4-triazol-5-yl)methyl][1,1'-biphenyl]-2-yl]-1H-tetrazole;
5-[4'-[(1-cyclohexyl-3-butoxy-1H-1,2,4-triazol-5-yl)methyl][1,1'-biphenyl]-2-yl]-1H-tetrazole;
5-[4'-[(1-cyclohexyl-3-thiomethyl-1H-1,2,4-triazol-5-yl)methyl][1,1'-biphenyl]-2-yl]-1H-tetrazole;
5-[4'-[(1-cyclohexyl-3-thioethyl-1H-1,2,4-triazol-5-yl)methyl][1,1'-biphenyl]-2-yl]-1H-tetrazole;
5-[4'-[(1-cyclohexyl-3-thiopropyl-1H-1,2,4-triazol-5-yl)methyl][1,1'-biphenyl]-2-yl]-1H-tetrazole;
5-[4'-[(1-cyclohexyl-3-thioisopropyl-1H-1,2,4-triazol-5-yl)methyl][1,1'-biphenyl]-2-yl]-1H-tetrazole;
5-[4'-[[1-cyclohexyl-3-(1-butenyl)-1H-1,2,4-triazol-5-yl]methyl][1,1'-biphenyl]-2-yl]-1H-tetrazole;
5-[4'-[[1,3-di(2-butenyl)-1H-1,2,4-triazol-5-yl]methyl][1,1'-biphenyl]-2-yl]-1H-tetrazole;
5-[4'-[[1,3-di(3-butenyl)-1H-1,2,4-triazol-5-yl]methyl][1,1'-biphenyl]-2-yl]-1H-tetrazole;
5-[4'-[[1,3-dihexyl-1H-1,2,4-triazol-5-yl]methyl][1,1'-biphenyl]-2-yl]-1H-tetrazole;
5-[4'-[[1,3-di(2-butynyl)-1H-1,2,4-triazol-5-yl]methyl][1,1'-biphenyl]-2-yl]-1H-tetrazole; and
5-[4'-[[1,3-di(3-butynyl)-1H-1,2,4-triazol-5-yl]methyl][1,1'-biphenyl]-2-yl]-1H-tetrazole.

A family of specific compounds of more particular interest within Formula I consists of compounds and pharmaceutically-acceptable salts thereof, as follows:
4'-[(1-butyl-3-propyl-1H-1,2,4-triazol-5-yl)methyl][1,1'-biphenyl]-2-carboxylic acid;
4'-[(1,3-dibutyl-1H-1,2,4-triazol-5-yl)methyl][1,1'-biphenyl]-2-carboxylic acid;
4'-[(1-butyl-3-isopentyl-1H-1,2,4-triazol-5-yl)methyl][1,1'-biphenyl]-2-carboxylic acid;
4'-[(1-butyl-3-cyclohexylmethyl-1H-1,2,4-triazol-5-yl)methyl][1,1'-biphenyl]-2-carboxylic acid;
4'-[[1-butyl-3-(2-cyclohexylethyl))-1H-1,2,4-triazol-5-yl]methyl][1,1'-biphenyl]-2-carboxylic acid;
4'-[[1-butyl-3-(1,1-difluoro-2-cyclohexylethyl)-1H-1,2,4-triazol-5-yl]methyl][1,1'-biphenyl]-2-carboxylic acid;
4'-[[1-butyl-3-(1,1-difluoro-3-cyclohexylpropyl)-1H-1,2,4-triazol-5-yl]methyl][1,1'-biphenyl]-2-carboxylic acid;
4'-[[1-butyl-3-(1,1-dimethoxybutyl)-1H-1,2,4-triazol-5-yl]methyl][1,1'-biphenyl]-2-carboxylic acid;

4'-[[1-butyl-3-(1-oxobutyl)-1H-1,2,4-triazol-5-yl]methyl][1,1'-biphenyl]-2-carboxylic acid;
4'-[[1-butyl-3-(1-oxopentyl)-1H-1,2,4-triazol-5-yl]methyl][1,1'-biphenyl]-2-carboxylic acid;
4'-[[1-butyl-3-(1,1-difluoroethyl)-1H-1,2,4-triazol-5-yl]methyl][1,1'-biphenyl]-2-carboxylic acid;
4'-[[1-butyl-3-(1,1-difluoropropyl)-1H-1,2,4-triazol-5-yl]methyl][1,1'-biphenyl]-2-carboxylic acid;
4'-[[3-butyl-1-(1,1-difluorobutyl)-1H-1,2,4-triazol-5-yl]methyl][1,1'-biphenyl]-2-carboxylic acid;
4'-[[1-butyl-3-(1,1-difluoropentyl)-1H-1,2,4-triazol-5-yl]methyl][1,1'-biphenyl]-2-carboxylic acid;
4'-[(1-butyl-3-phenylmethyl-1,2,4,-triazol-5-yl)methyl][1,1'-biphenyl]-2-carboxylic acid;
4'-[[1-butyl-3-(2-phenylethyl)-1H-1,2,4-triazol-5-yl]methyl][1,1'-biphenyl]-2-carboxylic acid;
4'-[[1-butyl-3-(1,1-difluoro-2-phenylethyl)-1H-1,2,4-triazol-5-yl]methyl][1,1'-biphenyl]-2-carboxylic acid;
4'-[[1-butyl-3-(1,1-difluoro-3-phenylpropyl)-1H-1,2,4-triazol-5-yl]methyl][1,1'-biphenyl]-2-carboxylic acid;
4'-[(1,3-dipropyl-1H-1,2,4-triazol-5-yl)methyl][1,1'-biphenyl]-2-carboxylic acid;
4'-[(1,3-isopropyl-1H-1,2,4-triazol-5-yl)methyl][1,1'-biphenyl]-2-carboxylic acid;
5-[4'-[(1-propyl-3-butyl-1H-1,2,4-triazol-5-yl)methyl][1,1'-biphenyl]-2-carboxylic acid;
5-[4'-[(1-butyl-3-phenylmethyl-1,2,4,-triazol-5-yl)methyl][1,1'-biphenyl]-2-yl]-1H-tetrazole;
5-[4'-[[1-butyl-3-(2-phenylethyl)-1H-1,2,4-triazol-5-yl]methyl][1,1'-biphenyl]-2-yl]-1H-tetrazole;
5-[4'-[[1-butyl-3-(1,1-difluoro-2-phenylethyl)-1H-1,2,4-triazol-5-yl]methyl][1,1'-biphenyl]-2-yl]-1H-tetrazole;
5-[4'-[[1-butyl-3-(1,1-difluoro-3-phenylpropyl)-1H-1,2,4-triazol-5-yl]methyl][1,1'-biphenyl]-2-yl]-1H-tetrazole;
5-[4'-[(1-butyl-3-cyclohexylmethyl-1H-1,2,4-triazol-5-yl)methyl][1,1'-biphenyl]-2-yl]-1H-tetrazole;
5-[4'-[[1-butyl-3-(2-cyclohexylethyl))-1H-1,2,4-triazol-5-yl]methyl][1,1'-biphenyl]-2-yl]-1H-tetrazole;
5-[4'-[[1-butyl-3-(1,1-difluoro-2-cyclohexylethyl))-1H-1,2,4-triazol-5-yl]methyl][1,1'-biphenyl]-2-yl]-1H-tetrazole;
5-[4'-[[1-butyl-3-(1,1-difluoro-3-cyclohexylpropyl))-1H-1,2,4-triazol-5-yl]methyl][1,1'-biphenyl]-2-yl]-1H-tetrazole;
5-[4'-[(1-butyl-3-cyclohexanoyl-1,2,4,-triazol-5-yl)methyl][1,1'-biphenyl]-2-yl]-1H-tetrazole;
4'-[[1-propyl-3-(1,1-difluoroethyl)-1H-1,2,4-triazol-5-yl]methyl][1,1'-biphenyl]-2-carboxylic acid;
4'-[[1-propyl-3-(1,1-difluoropropyl)-1H-1,2,4-triazol-5-yl]methyl][1,1'-biphenyl]-2-carboxylic acid;
4'-[[1-propyl-3-(1,1-difluorobutyl)-1H-1,2,4-triazol-5-yl]methyl][1,1'-biphenyl]-2-carboxylic acid;
4'-[[1-propyl-3-(1,1-difluoropentyl)-1H-1,2,4-triazol-5-yl]methyl][1,1'-biphenyl]-2-carboxylic acid;
4'-[[1-ethyl-3-(1,1-difluorobutyl)-1H-1,2,4-triazol-5-yl]methyl][1,1'-biphenyl]-2-carboxylic acid;
4'-[(1,3-disecbutyl-1H-1,2,4-triazol-5-yl)methyl][1,1'-biphenyl]-2-carboxylic acid;
4'-[[1-secbutyl-3-(1,1-difluorobutyl)-1H-1,2,4-triazol-5-yl]methyl][1,1'-biphenyl]-2-carboxylic acid;
4'-[(1,3-diisobutyl-1H-1,2,4-triazol-5-yl)methyl][1,1'-biphenyl]-2-carboxylic acid;
4'-[[1-isobutyl-3-(1,1-difluorobutyl)-1H-1,2,4-triazol-5-yl]methyl][1,1'-biphenyl]-2-carboxylic acid;
4'-[(1,3-ditertbutyl-1H-1,2,4-triazol-5-yl)methyl][1,1'-biphenyl]-2-carboxylic acid;
4'-[[1-tertbutyl-3-(1,1-difluorobutyl)-1H-1,2,4-triazol-5-yl]methyl][1,1'-biphenyl]-2-carboxylic acid;
4'-[(1,3-dipentyl-1H-1,2,4-triazol-5-yl)methyl][1,1'-biphenyl]-2-carboxylic acid;
4'-[[1-pentyl-3-(1,1-difluorobutyl)-1H-1,2,4-triazol-5-yl]methyl][1,1'-biphenyl]-2-carboxylic acid;
4'-[(1,3-diisopentyl-1H-1,2,4-triazol-5-yl)methyl][1,1'-biphenyl]-2-carboxylic acid;
4'-[[1-isopentyl-3-(1,1-difluorobutyl)-1H-1,2,4-triazol-5-yl]methyl][1,1'-biphenyl]-2-carboxylic acid;
4'-[[1-(2-butenyl)-3-(1,1-difluorobutyl)-1H-1,2,4-triazol-5-yl]methyl][1,1'-biphenyl]-2-carboxylic acid;
4'-[[1-(3-butenyl)-3-(1,1-difluorobutyl)-1H-1,2,4-triazol-5-yl]methyl][1,1'-biphenyl]-2-carboxylic acid;
4'-[[1-(2-butynyl)-3-(1,1-difluorobutyl)-1H-1,2,4-triazol-5-yl]methyl][1,1'-biphenyl]-2-carboxylic acid;
4'-[[1-(3-butynyl)-3-(1,1-difluorobutyl)-1H-1,2,4-triazol-5-yl]methyl][1,1'-biphenyl]-2-carboxylic acid;
4'-[[1,3-di(2-butenyl)-1H-1,2,4-triazol-5-yl]methyl][1,1'-biphenyl]-2-carboxylic acid;
4'-[[1,3-di(3-butenyl)-1H-1,2,4-triazol-5-yl]methyl][1,1'-biphenyl]-2-carboxylic acid;
4'-[[1,3-di(2-butynyl)-1H-1,2,4-triazol-5-yl]methyl][1,1'-biphenyl]-2-carboxylic acid;
4'-[[1,3-di(3-butynyl)-1H-1,2,4-triazol-5-yl]methyl][1,1'-biphenyl]-2-carboxylic acid;
5-[4'-[(1-butyl-3-propyl-1H-1,2,4-triazol-5-yl)methyl][1,1'-biphenyl]-2-yl]-1H-tetrazole;
5-[4'-[(1,3-dibutyl-1H-1,2,4-triazol-5-yl)methyl][1,1'-biphenyl]-2-yl]-1H-tetrazole;
5-[4'-[(1-butyl-3-isopentyl-1H-1,2,4-triazol-5-yl)methyl][1,1'-biphenyl]-2-yl]-1H-tetrazole;
5-[4'-[[1-butyl-3-(1,1 dimethoxybutyl)-1H-1,2,4-triazol-5-yl]methyl][1,1'-biphenyl]-2-yl]-1H-tetrazole;
5-[4'-[[1-butyl-3-(1-oxobutyl)-1H-1,2,4-triazol-5-yl]methyl][1,1'-biphenyl]-2-yl]-1H-tetrazole;
5-[4'-[[1-butyl-3-(1,1-difluoroethyl)-1H-1,2,4-triazol-5-yl]methyl][1,1'-biphenyl]-2-yl]-1H-tetrazole;
5-[4'-[[1-butyl-3-(1,1-difluoropropyl)-1H-1,2,4-triazol-5-yl]methyl][1,1'-biphenyl]-2-yl]-1H-tetrazole;
5-[4'-[[1-butyl-3-(1,1-difluorobutyl)-1H-1,2,4-triazol-5-yl]methyl][1,1'-biphenyl]-2-yl]-1H-tetrazole;
5-[4'-[[1-butyl-3-(1,1-difluoropentyl)-1H-1,2,4-triazol-5-yl]methyl][1,1'-biphenyl]-2-yl]-1H-tetrazole;
5-[4'-[(1,3-dipropyl-1H-1,2,4-triazol-5-yl)methyl][1,1'-biphenyl]-2-yl]-1H-tetrazole;
5-[4'-[(1,3-isopropyl-1H-1,2,4-triazol-5-yl)methyl][1,1'-biphenyl]-2-yl]-1H-tetrazole;
5-[4'-[(1-propyl-3-isopentyl-1H-1,2,4-triazol-5-yl)methyl][1,1'-biphenyl]-2-yl]-1H-tetrazole;
5-[4'-[[1-propyl-3-(1,1-dimethoxybutyl)-1H-1,2,4-triazol-5-yl]methyl][1,1'-biphenyl]-2-yl]-1H-tetrazole;
5-[4'-[[1-propyl-3-(1-oxobutyl)-1H-1,2,4-triazol-5-yl]methyl][1,1'-biphenyl]-2-yl]-1H-tetrazole;
5-[4'-[[1-propyl-3-(1,1-difluoroethyl)-1H-1,2,4-triazol-5-yl]methyl][1,1'-biphenyl]-2-yl]-1H-tetrazole;
5-[4'-[[1-propyl-3-(1,1-difluoropropyl)-1H-1,2,4-triazol-5-yl]methyl][1,1'-biphenyl]-2-yl]-1H-tetrazole;
5-[4'-[[1-propyl-3-(1,1-difluorobutyl)-1H-1,2,4-triazol-5-yl]methyl][1,1'-biphenyl]-2-yl]-1H-tetrazole;
5-[4'-[[1-propyl-3-(1,1-difluoropentyl)-1H-1,2,4-triazol-5-yl]methyl][1,1'-biphenyl]-2-yl]-1H-tetrazole;
5-[4'-[[1-ethyl-3-(1,1-difluorobutyl)-1H-1,2,4-triazol-5-yl]methyl][1,1'-biphenyl]-2-yl]-1H-tetrazole;
5-[4'-[(1-secbutyl-3-propyl-1H-1,2,4-triazol-5-yl)methyl][1,1'-biphenyl]-2-yl]-1H-tetrazole;
5-[4'-[(1-secbutyl-3-butyl-1H-1,2,4-triazol-5-yl)methyl][1,1'-biphenyl]-2-yl]-1H-tetrazole;

5-[4'-[(1,3-disecbutyl-1H-1,2,4-triazol-5-yl)methyl][1,1'-biphenyl]-2-yl]-1H-tetrazole;
5-[4'-[(1-secbutyl-3-isopentyl-1H-1,2,4-triazol-5-yl)methyl][1,1'-biphenyl]-2-yl]-1H-tetrazole;
5-[4'-[[1-secbutyl-3-(1,1-difluoroethyl)-1H-1,2,4-triazol-5-yl]methyl][1,1'-biphenyl]-2-yl]-1H-tetrazole;
5-[4'-[[1-secbutyl-3-(1,1-difluoropropyl)-1H-1,2,4-triazol-5-yl]methyl][1,1'-biphenyl]-2-yl]-1H-tetrazole;
5-[4'-[[1-secbutyl-3-(1,1-difluorobutyl)-1H-1,2,4-triazol-5-yl]methyl][1,1'-biphenyl]-2-yl]-1H-tetrazole;
5-[4'-[[1-secbutyl-3-(1,1-difluoropentyl)-1H-1,2,4-triazol-5-yl]methyl][1,1'-biphenyl]-2-yl]-1H-tetrazole;
5-[4'-[(1-isobutyl-3-propyl-1H-1,2,4-triazol-5-yl)methyl][1,1'-biphenyl]-2-yl]-1H-tetrazole;
5-[4'-[(1-isobutyl-3-butyl-1H-1,2,4-triazol-5-yl)methyl][1,1'-biphenyl]-2-yl]-1H-tetrazole;
5-[4'-[(1,3-diisobutyl-1H-1,2,4-triazol-5-yl)methyl][1,1'-biphenyl]-2-yl]-1H-tetrazole;
5-[4'-[(1-isobutyl-3-isopentyl-1H-1,2,4-triazol-5-yl)methyl][1,1'-biphenyl]-2-yl]-1H-tetrazole;
5-[4'-[[1-isobutyl-3-(1,1-difluoroethyl)-1H-1,2,4-triazol-5-yl]methyl][1,1'-biphenyl]-2-yl]-1H-tetrazole;
5-[4'-[[1-isobutyl-3-(1,1-difluoropropyl)-1H-1,2,4-triazol-5-yl]methyl][1,1'-biphenyl]-2-yl]-1H-tetrazole;
5-[4'-[[1-isobutyl-3-(1,1-difluorobutyl)-1H-1,2,4-triazol-5-yl]methyl][1,1'-biphenyl]-2-yl]-1H-tetrazole;
5-[4'-[[1-isobutyl-3-(1,1-difluoropentyl)-1H-1,2,4-triazol-5-yl]methyl][1,1'-biphenyl]-2-yl]-1H-tetrazole;
5-[4'-[(1-tertbutyl-3-propyl-1H-1,2,4-triazol-5-yl)methyl][1,1'-biphenyl]-2-yl]-1H-tetrazole;
5-[4'-[(1-tertbutyl-3-butyl-1H-1,2,4-triazol-5-yl)methyl][1,1'-biphenyl]-2-yl]-1H-tetrazole;
5-[4'-[(1,3-ditertbutyl-1H-1,2,4-triazol-5-yl)methyl][1,1'-biphenyl]-2-yl]-1H-tetrazole;
5-[4'-[(1-tertbutyl-3-isopentyl-1H-1,2,4-triazol-5-yl)methyl][1,1'-biphenyl]-2-yl]-1H-tetrazole;
5-[4'-[[1-tertbutyl-3-(1,1-difluoroethyl)-1H-1,2,4-triazol-5-yl]methyl][1,1,-biphenyl]-2-yl]-1H-tetrazole;
5-[4'-[[1-tertbutyl-3-(1,1-difluoropropyl)-1H-1,2,4-triazol-5-yl]methyl][1,1'-biphenyl]-2-yl]-1H-tetrazole;
5-[4'-[[1-tertbutyl-3-(1,1-difluorobutyl)-1H-1,2,4-triazol-5-yl]methyl][1,1'-biphenyl]-2-yl]-1H-tetrazole;
5-[4'-[[1-tertbutyl-3-(1,1-difluoropentyl)-1H-1,2,4-triazol-5-yl]methyl][1,1'-biphenyl]-2-yl]-1H-tetrazole;
5-[4'-[(1-pentyl-3-propyl-1H-1,2,4-triazol-5-yl)methyl][1,1'-biphenyl]-2-yl]-1H-tetrazole;
5-[4'-[(1-pentyl-3-butyl-1H-1,2,4-triazol-5-yl)methyl][1,1'-biphenyl]-2-yl]-1H-tetrazole;
5-[4'-[(1,3-dipentyl-1H-1,2,4-triazol-5-yl)methyl][1,1'-biphenyl]-2-yl]-1H-tetrazole;
5-[4'-[(1-pentyl-3-isopentyl-1H-1,2,4-triazol-5-yl)methyl][1,1'-biphenyl]-2-yl]-1H-tetrazole;
5-[4'-[[1-pentyl-3-(1,1-difluoroethyl)-1H-1,2,4-triazol-5-yl]methyl][1,1'-biphenyl]-2-yl]-1H-tetrazole;
5-[4'-[[1-pentyl-3-(1,1-difluoropropyl)-1H-1,2,4-triazol-5-yl]methyl][1,1'-biphenyl]-2-yl]-1H-tetrazole;
5-[4'-[[1-pentyl-3-(1,1-difluorobutyl)-1H-1,2,4-triazol-5-yl]methyl][1,1'-biphenyl]-2-yl]-1H-tetrazole;
5-[4'-[[1-pentyl-3-(1,1-difluoropentyl)-1H-1,2,4-triazol-5-yl]methyl][1,1'-biphenyl]-2-yl]-1H-tetrazole;
5-[4'-[(1-isopentyl-3-ethyl-1H-1,2,4-triazol-5-yl)methyl][1,1'-biphenyl]-2-yl]-1H-tetrazole;
5-[4'-[(1-isopentyl-3-propyl-1H-1,2,4-triazol-5-yl)methyl][1,1'-biphenyl]-2-yl]-1H-tetrazole;
5-[4'-[(1-isopentyl-3-butyl-1H-1,2,4-triazol-5-yl)methyl][1,1'-biphenyl]-2-yl]-1H-tetrazole;
5-[4'-[(1,3-diisopentyl-1H-1,2,4-triazol-5-yl)methyl][1,1'-biphenyl]-2-yl]-1H-tetrazole;
5-[4'-[[1-isopentyl-3-(1,1-difluoroethyl)-1H-1,2,4-triazol-5-yl]methyl][1,1'-biphenyl]-2-yl]-1H-tetrazole;
5-[4'-[[1-isopentyl-3-(1,1-difluoropropyl)-1H-1,2,4-triazol-5-yl]methyl][1,1'-biphenyl]-2-yl]-1H-tetrazole;
5-[4'-[[1-isopentyl-3-(1,1-difluorobutyl)-1H-1,2,4-triazol-5-yl]methyl][1,1'-biphenyl]-2-yl]-1H-tetrazole;
5-[4'-[[1-isopentyl-3-(1,1-difluoropentyl)-1H-1,2,4-triazol-5-yl]methyl][1,1'-biphenyl]-2-yl]-1H-tetrazole;
5-[4'-[[1-(2-butenyl)-3-(1,1-difluorobutyl)-1H-1,2,4-triazol-5-yl]methyl][1,1'-biphenyl]-2-yl]-1H-tetrazole;
5-[4'-[[1-(3-butenyl)-3-(1,1-difluorobutyl)-1H-1,2,4-triazol-5-yl]methyl][1,1'-biphenyl]-2-yl]-1H-tetrazole;
5-[4'-[[1-(2-butynyl)-3-(1,1-difluorobutyl)-1H-1,2,4-triazol-5-yl]methyl][1,1'-biphenyl]-2-yl]-1H-tetrazole;
5-[4'-[[1-(3-butynyl)-3-(1,1-difluorobutyl)-1H-1,2,4-triazol-5-yl]methyl][1,1'-biphenyl]-2-yl]-1H-tetrazole;
5-[4'-[[1,3-di(2-butenyl)-1H-1,2,4-triazol-5-yl]methyl][1,1'-biphenyl]-2-yl]-1H-tetrazole;
5-[4'-[[1,3-di(3-butenyl)-1H-1,2,4-triazol-5-yl]methyl][1,1'-biphenyl]-2-yl]-1H-tetrazole;
5-[4'-[[1,3-di(2-butynyl)-1H-1,2,4-triazol-5-yl]methyl][1,1'-biphenyl]-2-yl]-1H-tetrazole; and
5-[4'-[[1,3-di(3-butynyl)-1H-1,2,4-triazol-5-yl]methyl][1,1'-biphenyl]-2-yl]-1H-tetrazole.

The term "hydrido" denotes a single hydrogen atom (H) which may be attached, for example, to a carbon atom to form a hydrocarbyl group or attached to an oxygen atom to form an hydroxyl group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atomms. The term "cycloalkyl" embraces cyclic radicals having three to about ten ring carbon atoms, preferably three to about six carbon atoms, such as cyclopropyl and cyclobutyl. The term "cycloalkylalkyl" is exemplified by cyclohexylmethyl and cyclohexylethyl, either of which may be optionally attached to a substitutable position of Formula I through a carbonyl moiety. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. Preferably, when the difluoroalkyl group is attached at the triazole ring $R^1$ and $R^2$ positions of Formula I, the two fluoro atoms are substituted on the carbon atom which is attached directly to the triazole ring. Such preferred difluoroalkyl group may be characterized as an "alphacarbon difluoro-substituted difluoroalkyl group" The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The terms "aralkyl" and "arylalkyl" embrace aryl-substituted alkyl radicals such as benzyl, diphenylmethyl, triphenylmethyl, phenylethyl, phenylbutyl and diphenylethyl. Aralkyl groups may be attached to a carbonyl to form a radical attachable through the carbonyl to a substitutable position on Formula I. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to a hypertensive condition if not treated to prevent or control such hypertension.

Included within the family of compounds of Formula I are the tautomeric forms of the described compounds and all diastereoisomers thereof and the pharmaceutically-acceptable salts thereof. The biphenylalkyl 1,3,5-trisubstituted-1,2,4-triazole compounds of the invention embrace two major sub-sets of triazole derivatives. A first sub-set of such derivatives consists of those 1,3,5-trisubstituted-1,2,4-triazoles having the biphenylalkyl substituent at the five-position of the triazole and having the $R^1$ and $R^2$ substituents at the one- and three-positions, respectively, of the triazole, as depicted in Formula I and exemplified by Examples 1 and 3, herein. A second sub-set of such derivatives consists of those 1,3,5-trisubstituted-1,2,4-triazoles having the biphenylalkyl substituent at the three-position of the triazole and having the $R^1$ and $R^2$ substituents at the one- and five-positions, respectively, of the triazole, as exemplified by Examples 2 and 4, herein. Both of the first and second sub-sets described above are embraced as compounds of the invention.

The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–III, wherein each of the substituents $R^1$ and $R^2$ are as defined for Formula I above, except where further noted.

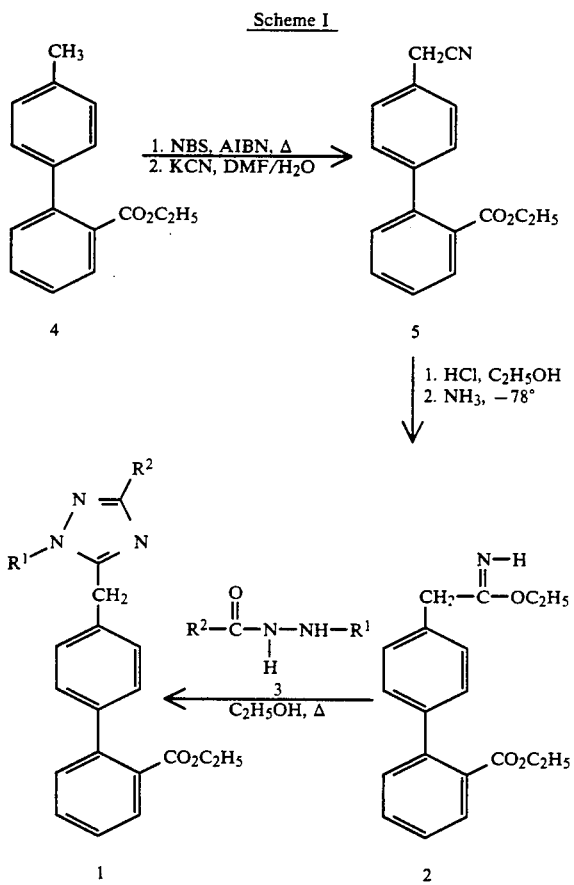

$R^1 = H, C_2H_9(n),$ etc.

Synthetic Scheme I shows the preparation of 3,5-disubstituted 1H-1,2,4-triazoles 1 ($R^1=H$) from the iminoester 2 and the hydrazide 3 ($R^1=H$) and the regiospecific preparation of 1,3,5-trisubstituted 1H-1,2,4-triazoles 1 ($R^1=C_4H_9(n)$, etc.) from the iminoester 2 and the hydrazide 3 ($R^1=C_4H_9(n)$, etc.). In step 1, the benzyl group of 4 is brominated with NBS and subsequently converted to the cyanobenzyl derivative 5 by reaction with potassium cyanide. In step 2, the nitrile is reacted with anhydrous hydrogen chloride/ethanol to give the iminoester hydrochloride which is subsequently converted to the free iminoester 2 on treatment with ammonia. In step 3, the iminoester 2 is reacted with the appropriate hydrazide 3 to give the desired triazole 1.

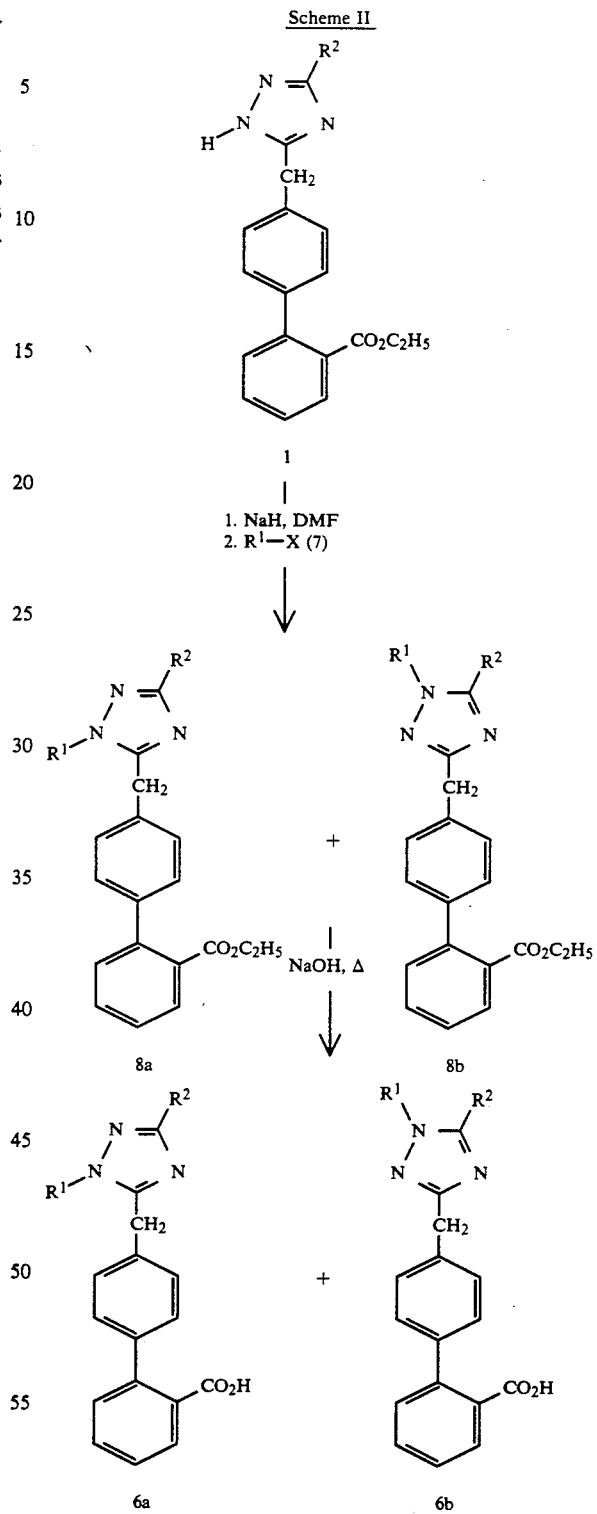

Synthetic Scheme II shows the preparation of the two regioisomeric 1,3,5-trisubstituted 1H-1,2,4-triazoles 6a and 6b from the corresponding 3,5-disubstituted triazole 1 and the appropriate alkylating reagent 7. In step 1, the triazole 1 is treated with an appropriate base, such as sodium hydride, to generate the corresponding anion which is subsequently reacted with an alkylating reagent 7 to give a mixture of regioisomeric triazole esters 8a and 8b. In step 2, the mixture of esters is reacted with aqueous sodium hydroxide/ethanol to give a mixture of regioisomeric triazole acids 6a and 6b which may be subsequently separated by chromatographic methods. Or, the regioisomers 8a and 8b may be separated by chromatographic methods and each regioisomer subsequently reacted with aqueous sodium hydroxide/ethanol to provide 6a or 6b, respectively.

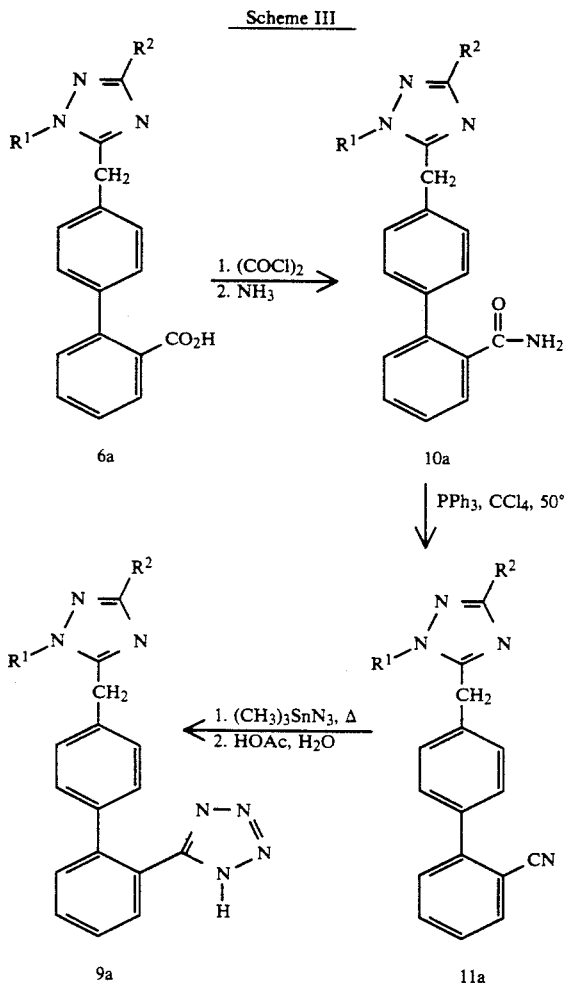

Synthetic Scheme III shows the conversion of the acid derivatives 6a to the corresponding tetrazole derivative 9a. In step 1, the acid 6a is reacted with oxalyl chloride and subsequently with ammonia to give the corresponding primary amide derivative 10a. In step 2, the amide 10a is reacted with triphenylphosphine/carbon tetrachloride to give the nitrile 11a. In step 3, the nitrile 11a is reacted with trimethyltin azide to give the corresponding trimethyltin tetrazole which is subsequently reacted with acetic acid/water to give the desired tetrazole derivative 9a. The sequence of reactions outlined in Scheme III may be employed on each individual regioisomer 6a or 6b, or on a mixture of 6a and 6b with subsequent separation by chromatographic methods of the regioisomers 9a and 9b thus produced.

The following Examples 1-4 are detailed descriptions of the methods of preparation of compounds of Formula I. These detailed preparations fall within the scope of, and serve to exemplify, the above described General Synthetic Procedures which form part of the invention. These Examples 1-4 are presented for illustrative purposes only and are not intended as a restriction on the scope of the invention. All parts are by weight unless otherwise indicated.

EXAMPLE 1

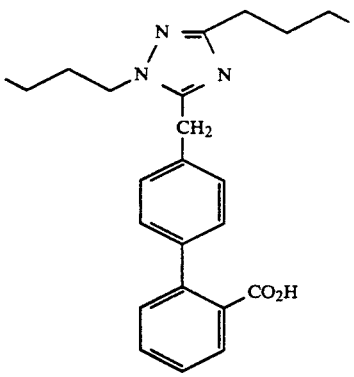

4'[1,3-dibutyl-1H-1,2,4-triazol-5-yl)methyl][1,1'-biphenyl]-2-carboxylic acid

Step 1: Preparation of 4'-cyanomethylbiphenyl-2-carboxylate

Under nitrogen, a sodium ethoxide solution was prepared by reacting 4.05 g (176 mmol) of metallic sodium with 400 mL of absolute ethanol. A 20.0 g (88 mmol) sample of methyl 4'-methylbiphenyl-2-carboxylate (Chemo Dynamics Inc.) was added and the reaction was allowed to stir at reflux for 5 days. The reaction was concentrated in vacuo and partitioned between water and ether. The organic layer was dried (MgSO$_4$) and reconcentrated in vacuo to give 17.9 g (85%) of ethyl 4'-methylbiphenyl-2-carboxylate (4 in Scheme I): NMR (CDCl$_3$) δ 1.06 (t, J=7 Hz, 3H), 2.52 (s, 3H), 4.14 (q, J=7 Hz, 2H), 7.18-7.27 (m, 4H), 7.35-7.44 (m, 2H), 7.48-7.56 (m, 1H), 7.83 (d, J=8 Hz, 1H). A 17.9 g (75 mmol) sample of the ethyl ester was dissolved in carbon tetrachloride and treated under nitrogen with 13.35 g (75 mmol) of N-bromosuccinimide (NBS) and 0.57 g (3.5 mmol) of azobisisobutyronitrile (AIBN). The reaction was stirred at reflux for 28 h, filtered, and concentrated in vacuo. Purification by silica gel chromatography (Waters Prep-500A) using ethyl acetate/hexane (5:95) gave 20.4 g (85%) of ethyl 4'-bromomethylbiphenyl-2-carboxylate as a pale yellow oil: NMR (CDCl$_3$) δ 1.02 (t, J=7 Hz, 3H), 4.10 (q, J=7 Hz, 2H), 4.58 (s, 2H), 7.24-7.48 (m, 5H), 7.48-7 62 (m, 2H), 7.85 (dd, J=8 and 2 Hz, 1H). A 20.37 g (64 mmol) sample of the bromide was dissolved in 440 mL of dimethylformamide (DMF)/water (10:1) and treated with 4.58 (70 mmol) of potassium cyanide. The reaction was stirred at ambient temperature for 72 h, concentrated in vacuo, and partitioned between water and methylene chloride; the organic layer was dried (MgSO$_4$) and reconcentrated in vacuo. Purification by silica gel chromatography (Waters Prep-500A) using ethyl acetate/hexane (20:80) gave 11.3 g (67%) of ethyl 4'-cyanomethylbiphenyl-2-carboxylate (5 in Scheme I) as a colorless solid: mp 65.5°-67.0° C.; NMR (CDCl$_3$) δ 1.07 (t, J=7 Hz, 3H), 3.80 (s, 2H), 4.12 (q, J=7 Hz, 2H), 7.30-7.39 (m, 5H), 7.43 (td, J=8 and 2 Hz, 1H), 7.54 (td, J=8 and 2H, 1H), 7.87 (dd, J=8 Hz, 1H).

Step 2: Preparation of ethyl 4'-[(3-butyl-1H-1,2,4-triazol-5-yl)methyl][1,1'-biphenyl]-2-carboxylate A 11.3 g (43 mmol) sample of the nitrile from step 1 was dissolved in 122 mL of anhydrous ether to which 2.7 mL of absolute ethanol was added and treated at −15° C. with 9 g (25 mmol) of anhydrous hydrogen chloride. The reaction was stirred at 5° C. for 23 days, cooled to −78° C., and treated with 5.7 g (34 mmol) of anhydrous ammonia. The suspension was filtered and the filtrate concentrated in vacuo providing 7.79 g (58%) of crude imidate ester (2 in Scheme I) as a golden viscous oil: NMR (CDCl$_3$) δ 1.02 (t, J=7 Hz, 3H), 1.17–1.37 (m, 3H), 3.59 (s, 2H), 4.04–4.24 (m, 4H), 7.21–7.46 (m, 6H), 7.48–7.57 (m, 1H), 7.79–7.87 (m, 1H). A 7.79 g (25 mmol) sample of the crude imidate was dissolved in 78 mL of absolute ethanol and treated with 3.0 g (26 mmol) of valeric acid hydrazide; the reaction was stirred under nitrogen at reflux for 6 days and then concentrated in vacuo. Purification by silica gel chromatography using ethyl acetate gave 3.66 g (23% from nitrile) of the triazole product (1 in Scheme I): NMR (CDCl$_3$) δ 0.93 (t, J=7 Hz, 3H), 1.04 (t, J=7 Hz, 3H), 1.32–1.46 (m, 2H), 1.67–1.78 (m, 2H), 2.73 (t, J=7 Hz, 2H), 4.11 (q, J=7 Hz, 2H), 4.13 (s, 2H), 7.21–7.36 (m, 5H), 7.40 (td, J=8 and 2 Hz, 1H), 7.51 (td, J=8 and 2 Hz, 1H), 7.82 (dd, J=8 and 2 Hz, 1H).

Step 3: Preparation of 4'-[(1,3-dibutyl-1H-1,2,4-triazol-5-yl)methyl][1,1'-biphenyl]-2-carboxylic acid Under nitrogen, a 3.66 g (10 mmol) sample of the triazole from step 2 was dissolved in 50 mL of DMF and treated 620 mg (13 mmol) of sodium hydride; the solution was cooled to 0° C. and treated with 1.4 g (10 mmol) of butyl bromide. The reaction was stirred at ambient temperature for 6 h, concentrated in vacuo, and partitioned between water and methylene chloride. The organic layer was dried (MgSO$_4$) and reconcentrated to give 4.19 g (100%) of a mixture of triazole isomers (8a and 8b in Scheme II). The mixture of triazole isomers was dissolved in 150 mL of ethanol and 150 mL of 2.5M sodium hydroxide. The reaction was stirred at reflux overnight, the ethanol removed in vacuo, and the pH adjusted to pH 2 with dilute hydrochloric acid. The water was decanted giving 3.19 g (83%) of a mixture of the two isomeric triazole acids (6a and 6b in Scheme II) as a very viscous oil. A small sample of this material was purified by reverse phase chromatography (Waters Deltaprep-3000) using isocratic acetonitrile/water (45:55) (0.05% TFA); the slower moving regioisomer was determined to be 4'-[1,3-dibutyl-1H-1,2,4-triazol-5-yl)methyl][1,1'-biphenyl]-2-carboxylic acid (6a in Scheme II): NMR (CDCl$_3$) δ 0.90 (t, J=7 Hz, 3H), 0.93 (t, J=7 Hz, 3H), 1.20–1.35 (m, 2H), 1.35–1.49 (m, 2H), 1.65–1.86 (m, 4H), 2.85 (t, J=7 Hz, 2H), 3.98–4.11 (m, 2H), 4.32–4.50 (br s, 2H), 7.21–7.38 (m, 5H), 7.45 (td, J=8 and 2 Hz, 1H), 7.56 (td, J=8 and 2 Hz, 1H), 7.95 (dd, J=8 and 2 Hz, 1H); MS (FAB) m/e (rel intensity) 392 (100), 318(19), 181(8), 165(10); HRMS. Calc'd for M+H: 392.2338. Found: 392.2301.

EXAMPLE 2

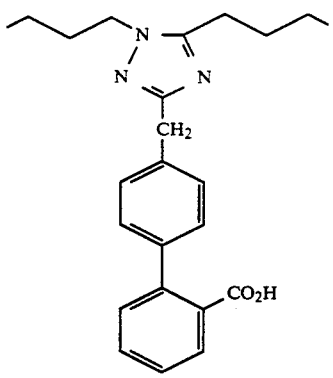

4'-[1,5-dibutyl-1H-1,2,4-triazol-3-yl)methyl][1,1'-biphenyl]-2-carboxylic acid

The faster moving regioisomer from step 3 of Example 1 was determined to be 4'-[1,5-dibutyl-1H-1,2,4-triazol-3-yl)methyl][1,1'-biphenyl]-2-carboxylic acid (6b in Scheme II): mp 135°–139° C.; NMR (CDCl$_3$) δ 0.92 (t, J=7 Hz, 3H), 0.95 (t, J=7 Hz, 3H), 1.21–1.47 (m, 4H), 1.62–1.87 (m, 4H), 2.70–2.86 (m, 2H), 3.84 (s, 2H), 3.91–4.05 (m, 2H), 7.17–7.54 (m, 7H), 7.87 (d, J=8 Hz, 1H); MS (FAB) m/e (rel intensity) 392 (100), 374(4); HRMS. Calc'd for M+H: 392.2338. Found: 392.2306.

EXAMPLE 3

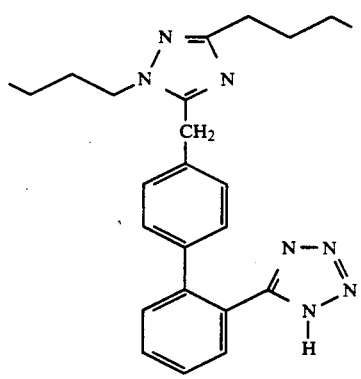

5-[4'-[(1,3-dibutyl-1H-1,2,4-triazol-5-yl)methyl][1,1'-biphenyl]-2-yl]-1H-tetrazole

Step 1: Preparation of 4'-[1,3-dibutyl-1H-1,2,4-triazol-5-yl)methyl][1,1'-biphenyl]-2-carboxylic acid, amide and 4'-[1,5-dibutyl-1H-1,2,4-triazol-3-yl)methyl][1,1'-biphenyl]-2-carboxylic acid, amide A 3.08 g (8.0 mmol) sample of the mixture of regioisomeric acids (from step 3 of Example 1) was dissolved in 33 mL of chloroform and treated with 13.1 g (10 mmol) of oxalyl chloride; the reaction was stirred under nitrogen overnight and concentrated in vacuo. The residue was redissolved in 36 mL of chloroform to which 4 mL of pentane was added and then treated at −78° C. with anhydrous ammonia; the stirred reaction was allowed to warm to ambient temperature overnight under nitrogen and then was concentrated in vacuo to give 3.87 g of crude material which was a mixture of regioisomeric amides (10a and 10b from Scheme III); no purification was attempted.

Step 2: Preparation of 2-[4'-[(1,3-dibutyl-1H-1,2,4-triazol-5-yl)methyl]phenyl]-benzonitrile and 2-[4'-[1,5-dibutyl-1H-1,2,4-triazol-3-yl)methyl]phenyl]-benzonitrile The crude mixture of amides from step 1 was dissolved in 35 mL of anhydrous tetrahydrofuran (THF) and treated with 5.62 g (21 mmol) of triphenylphosphine and 16.4 mL of carbon tetrachloride. Under nitrogen, the reaction was stirred at 50° C. overnight, filtered, and concentrated in vacuo. The residue was dissolved in methylene chloride, washed with aqueous sodium bicarbonate, dried (MgSO$_4$), and concentrated in vacuo. Purification by silica gel chromatography (Waters Prep-500A) using ethyl acetate/hexane (40:60) gave 1.9 g (63%) of a mixture of regioisomeric nitriles (11a and 11b in Scheme III): NMR (CDCl$_3$) δ 0.86 (t, J=7 Hz, 3H), 0.91-1.01 (m, 9H), 1.16-1.31 (m, 2H), 1.31-1.49 (m, 6H), 1.60-1.89 (m, 8H), 2.70 (q, J=7 Hz, 4H), 3.93 (t, J,=7 Hz, 2H), 4.00 (t, J=7 Hz, 2H), 4.08 (s, 2H), 4.19 (s, 2H), 7.32 (d, J=8 Hz, 2H), 7.37-7.55 (m, 10H), 7.58-7.67 (m, 2H), 7.81-7.88 (m, 2H).

Step 3: Preparation of 5-[4'-[(1,3-dibutyl-1H-1,2,4-triazol-5-yl)methyl][1,1'-biphenyl]-2-yl]-1H-tetrazole The purified mixture of regioisomeric nitriles (5 mmol) from step 2 was dissolved in 19 mL of xylene and treated with 2.1 g (10 mmol) of trimethyltin azide; the reaction was stirred under nitrogen at reflux for 2 days and then concentrated in vacuo. The residue was dissolved in 35 mL of acetic acid/water (90:10), stirred at ambient temperature overnight, and concentrated in vacuo. Purification by reverse phase chromatography (Waters Deltaprep-3000) using isocratic acetonitrile/water (40:60) (0.05% TFA) provided 5-[4'-[(1,3-dibutyl-1H-1,2,4-triazol-5-yl)methyl][1,1'-biphenyl]-2-yl]-1H-tetrazole as the slower moving regioisomer (9a in Scheme III): NMR (CDCl$_3$) δ 0.91 (t, J=7 Hz, 3H), 0.95 (t, J=7 Hz, 3H), 1.22-1.44 (m, 4H), 1.52-1.74 (m, 2H), 1.74-1.86 (m, 2H), 2.70 (t, J=7 Hz, 2H), 4.04 (t, J=7 Hz, 2H), 4.11 (s, 2H), 7.14-7.25 (m, 4H), 7.45 (dd, J=8 and 2 Hz, 1H), 7.49-7.63 (m, 2H), 8.05 (dd, J=8 and 2 Hz, 1H); MS (FAB) m/e (rel intensity) 416 (100), 388 (40), 207 (7); HRMS. Calc'd for M+H: 416.2563. Found: 416.2538.

EXAMPLE 4

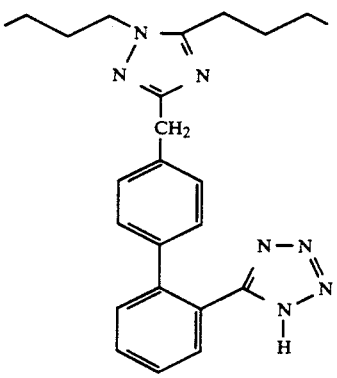

-continued
5-[4'-[(1,5-dibutyl-1H-1,2,4-triazol-3-yl)methyl][1,1'-biphenyl]-2-yl]-1H-tetrazole The faster moving regioisomer from step 3 of Example 3 was determined to be 5-[4'-[(1,5-dibutyl-1H-1,2,4-triazol-3-yl)methyl][1,1'-biphenyl]-2-yl]-1H-tetrazole (9b in Scheme III): NMR (CDCl$_3$) δ 0.94 (t, (J=7 Hz, 3H), 1.00 (t, J=7 Hz, 3H), 1.32-1.50 (m, 4H), 1.71-1.84 (m, 2H), 1.84-1.96 (m, 2H), 2.87-3.02 (m, 2H), 4.09 (t, J=7 Hz, 2H), 4.15 (s, 2H), 7.17-7.34 (m, 4H), 7.44-7.62 (m, 3H), 8.10 (d, J=8 Hz, 1H); MS (FAB) m/e (rel intensity) 416 (100), 388 (60), 207 (20); HRMS. Calc'd for M+H: 416.2563. Found: 416.2524.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120-124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500 x g for 20 min., and the supernatant was recentrifuged at 100,000 x g for 60 min. The pellet was resuspended in buffer consisting of 2 mM EDTA. and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 10$^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-AII from the high affinity AII receptor. Binding data were analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2-2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (MM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded ($3 \times 10^{-10}$ to $1 \times 10^{-5}$M). Each concentration of AII was allowed to elicit its maximal contraction, and then AII was washed out repeatedly for 30 minutes before rechallenging with a higher concentration of AII. Aorta rings were exposed to the test antagonist at $10^{-5}$M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [*Br. J. Pharmacol. Chemother.*, 2,189-206 (1947)]. The pA$_2$ value is the concentration of the antagonist which increases the EC$_{50}$ value for AII by a factor of two. Each test antagonist was evaluated in aorta rings from two rabbits. Results are reported in Table I.

TABLE I

| In Vitro Angiotensin II Activity of Compounds of the Invention | | |
|---|---|---|
| Test Compound Example # | [1]Assay A IC$_{50}$ (nM) | [2]Assay B pA$_2$ |
| 1 | 240 | 7.20/7.05 |
| 2 | 12,000 | 4.96 |
| 3 | 16 | 8.63/8.40 |
| 4 | 6,700 | 5.30 |

NT = NOT TESTED
[1]Assay A: Angiotensin II Binding Activity
[2]Assay B: In Vitro Vascular Smooth Muscle Response Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a glaucoma disorder, said method comprising administering to a subject having such disorder a therapeutically-effective amount of a compound of Formula I:

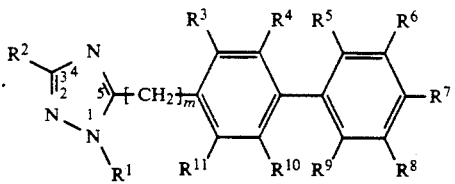

wherein m is one; wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl n-butyl, sec-butyl, isobutyl, isopentyl, tert-butyl, n-pentyl, neopentyl, 1-oxoethyl, 1-oxopropyl, 1-oxobutyl, 1-oxopentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein at least one of $R^5$, $R^6$, $R^8$ and $R^9$ is an acidic group and each of the remaining of $R^3$ through $R^{11}$ is hydrido, said acidic group selected from COOH and

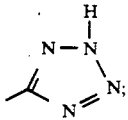

or a tautomer thereof or a pharmaceutically-acceptable salt thereof.

2. The method of claim 1 wherein m is one; wherein $R^1$ is selected from ethyl, n-propyl, isopropyl, n-butyl, sec-butyl, isobutyl, tert-butyl, isopentyl, n-pentyl, neopentyl, benzyl, cyclohexyl, cyclohexylmethyl and hydroxyalkyl; wherein $R^2$ is selected from ethyl, n-propyl, isopropyl, n-butyl, sec-butyl, isobutyl, isopentyl, n-pentyl, 1-oxo-2-phenylethyl, 1-oxo-2-cyclohexylethyl, 1,1-difluoro-2-phenylethyl, 1,1-difluoro-2-cyclohexylethyl, propylthio and butylthio; wherein each of $R^3$, $R^4$, $R^6$, $R^7$, $R^8$, $R^{10}$ and $R^{11}$ is hydrido; wherein one of $R^5$ and $R^9$ is hydrido and the other of $R^5$ and $R^9$ is an acidic group selected from COOH and

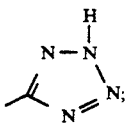

or a tautomer thereof or a pharmaceutically-acceptable salt thereof.

3. The method of claim 2 wherein said compound is selected from compounds, and their pharmaceutically-acceptable salts, of the group consisting of:

4'-[(1-butyl-3-propyl-1H-1,2,4-triazol-5-yl)methyl][1,1'-biphenyl]-2-carboxylic acid;

4'-[(1,3-dibutyl-1H-1,2,4-triazol-5-yl)methyl][1,1'-biphenyl]-2-carboxylic acid;

4'-[(1-butyl-3-isopentyl-1H-1,2,4-triazol-5-yl)methyl][1,1'-biphenyl]-2-carboxylic acid;

4'-[(1-butyl-3-cyclohexylmethyl-1H-1,2,4-triazol-5-yl)methyl][1,1'-biphenyl]-2-carboxylic acid;

4'-[[1-butyl-3-(2-cyclohexylethyl))-1H-1,2,4-triazol-5-yl]methyl][1,1'-biphenyl]-2-carboxylic acid;

4'-[[1-butyl-3-(1,1-difluoryl-2-cyclohexylethyl)-1H-1,2,4-triazol-5-yl]methyl][1,1'-biphenyl]-2-carboxylic acid;

4'-[[1-butyl-3-(1,1-difluoryl-3-cyclohexylpropyl)-1H-1,2,4-triazol-5-yl]methyl][1,1'-biphenyl]-2-carboxylic acid;

4'-[[1-butyl-3-(1,1-dimethoxybutyl)-1H-1,2,4-triazol-5-yl]methyl][1,1'-biphenyl]-2-carboxylic acid;

4'-[[1-butyl-3-(1-oxobutyl)-1H-1,2,4-triazol-5-yl]methyl][1,1'-biphenyl]-2-carboxylic acid;

4'-[[1-butyl-3-(1-oxopentyl)-1H-1,2,4-triazol-5-yl]methyl][1,1'-biphenyl]-2-carboxylic acid;

4'-[[1-butyl-3-(1,1-difluoroethyl)-1H-1,2,4-triazol-5-yl]methyl][1,1'-biphenyl]-2-carboxylic acid;

4'-[[1-butyl-3-(1,1-difluoropropyl)-1H-1,2,4-triazol-5-yl]methyl][1,1'-biphenyl]-2-carboxylic acid;

4'-[[1-butyl-3-(1,1-difluorobutyl)-1H-1,2,4-triazol-5-yl]methyl][1,1'-biphenyl]-2-carboxylic acid;

4'-[[1-butyl-3-(1,1-difluoropentyl)-1H-1,2,4-triazol-5-yl]methyl][1,1'-biphenyl]-2-carboxylic acid;

4'-[(1-butyl-3-phenylmethyl-1,2,4,-triazol-5-yl)methyl][1,1'-biphenyl]-2-carboxylic acid;

4'-[[1-butyl-3-(2-phenylethyl)-1H-1,2,4-triazol-5-yl]methyl][1,1'-biphenyl]-2-carboxylic acid;

4'-[[1-butyl-3-(1,1-difluoryl-2-phenylethyl)-1H-1,2,4-triazol-5-yl]methyl][1,1'-biphenyl]-2-carboxylic acid;

4'-[[1-butyl-3-(1,1-difluoryl-3-phenylpropyl)-1H-1,2,4-triazol-5-yl]methyl][1,1'-biphenyl]-2-carboxylic acid;

4'-[(1,3-dipropyl-1H-1,2,4-triazol-5-yl)methyl][1,1'-biphenyl]-2-carboxylic acid;

4'-[(1,3-isopropyl-1H-1,2,4-triazol-5-yl)methyl][1,1'-biphenyl]-2-carboxylic acid;

4'-[(1-propyl-3-butyl-1H-1,2,4-triazol-5-yl)methyl][1,1'-biphenyl]-2-carboxylic acid;

5-[4'-[(1-butyl-3-phenylmethyl-1,2,4,-triazol-5-yl)methyl][1,1'-biphenyl]-2-yl]-1H-tetrazole;

5-[4'-[[1-butyl-3-(2-phenylethyl)-1H-1,2,4-triazol-5-yl]methyl][1,1'-biphenyl]-2-yl]-1H-tetrazole;

5-[4'-[[1-butyl-3-(1,1-difluoryl-2-phenylethyl)-1H-1,2,4-triazol-5-yl]methyl][1,1'-biphenyl]-2-yl]-1H-tetrazole;

5-[4'-[[1-butyl-3-(1,1-difluoryl-3-phenylpropyl)-1H-1,2,4-triazol-5-yl]methyl][1,1'-biphenyl]-2-yl]-1H-tetrazole;

5-[4'-[(1-butyl-3-cyclohexylmethyl-1H-1,2,4-triazol-5-yl)methyl][1,1'-biphenyl]-2-yl]-1H-tetrazole;

5-[4'-[[1-butyl-3-(2-cyclohexylethyl))-1H-1,2,4-triazol-5-yl]methyl][1,1'-biphenyl]-2-yl]-1H-tetrazole;

5-[4'-[[1-butyl-3-(1,1-difluoryl-2-cyclohexylethyl))-1H-1,2,4-triazol-5-yl]methyl][1,1'-biphenyl]-2-yl]-1H-tetrazole;

5-[4'-[[1-butyl-3-(1,1-difluoryl-3-cyclohexylpropyl))-1H-1,2,4-triazol-5-yl]methyl][1,1'-biphenyl]-2-yl]-1H-tetrazole;

5-[4'-[(1-butyl-3-cyclohexanoyl-1,2,4,-triazol-5-yl)methyl][1,1'-biphenyl]-2-yl]-1H-tetrazole;

4'-[[1-propyl-3-(1,1-difluoroethyl)-1H-1,2,4-triazol-5-yl]methyl][1,1'-biphenyl]-2-carboxylic acid;

4'-[[1-propyl-3-(1,1-difluoropropyl)-1H-1,2,4-triazol-5-yl]methyl][1,1'-biphenyl]-2-carboxylic acid;

4'-[[1-propyl-3-(1,1-difluorobutyl)-1H-1,2,4-triazol-5-yl]methyl][1,1'-biphenyl]-2-carboxylic acid;
4'-[[1-propyl-3-(1,1-difluoropentyl)-1H-1,2,4-triazol-5-yl]methyl][1,1'-biphenyl]-2-carboxylic acid;
4'-[[1-ethyl-3-(1,1-difluorobutyl)-1H-1,2,4-triazol-5-yl]methyl][1,1'-biphenyl]-2-carboxylic acid;
4'-[(1,3-disecbutyl-1H-1,2,4-triazol-5-yl)methyl][1,1'-biphenyl]-2-carboxylic acid;
4'-[[1-secbutyl-3-(1,1-difluorobutyl)-1H-1,2,4-triazol-5-yl]methyl][1,1'-biphenyl]-2-carboxylic acid;
4'-[(1,3-diisobutyl-1H-1,2,4-triazol-5-yl)methyl][1,1'-biphenyl]-2-carboxylic acid;
4'-[[1-isobutyl-3-(1,1-difluorobutyl)-1H-1,2,4-triazol-5-yl]methyl][1,1'-biphenyl]-2-carboxylic acid;
4'-[(1,3-ditertbutyl-1H-1,2,4-triazol-5-yl)methyl][1,1'-biphenyl]-2-carboxylic acid;
4'-[[1-tertbutyl-3-(1,1-difluorobutyl)-1H-1,2,4-triazol-5-yl]methyl][1,1'-biphenyl]-2-carboxylic acid;
4'-[(1,3-dipentyl-1H-1,2,4-triazol-5-yl)methyl][1,1'-biphenyl]-2-carboxylic acid;
4'-[[1-pentyl-3-(1,1-difluorobutyl)-1H-1,2,4-triazol-5-yl]methyl][1,1'-biphenyl]-2-carboxylic acid;
4'-[(1,3-diisopentyl-1H-1,2,4-triazol-5-yl)methyl][1,1'-biphenyl]-2-carboxylic acid;
4'-[[1-isopentyl-3-(1,1-difluorobutyl)-1H-1,2,4-triazol-5-yl]methyl][1,1'-biphenyl]-2-carboxylic acid;
5-[4'-[(1-butyl-3-propyl-1H-1,2,4-triazol-5-yl)methyl][1,1'-biphenyl]-2-yl]-1H-tetrazole;
5-[4'-[(1,3-dibutyl-1H-1,2,4-triazol-5-yl)methyl][1,1'-biphenyl]-2-yl]-1H-tetrazole;
5-[4'-[(1-butyl-3-isopentyl-1H-1,2,4-triazol-5-yl)methyl][1,1'-biphenyl]-2-yl]-1H-tetrazole;
5-[4'-[[1-butyl-3-(1,1 dimethoxybutyl)-1H-1,2,4-triazol-5-yl]methyl][1,1'-biphenyl]-2-yl]-1H-tetrazole;
5-[4'-[[1-butyl-3-(1-oxobutyl)-1H-1,2,4-triazol-5-yl]methyl][1,1'-biphenyl]-2-yl]-1H-tetrazole;
5-[4'-[[1-butyl-3-(1,1-difluoroethyl)-1H-1,2,4-triazol-5-yl]methyl][1,1'-biphenyl]-2-yl]-1H-tetrazole;
5-[4'-[[1-butyl-3-(1,1-difluoropropyl)-1H-1,2,4-triazol-5-yl]methyl][1,1'-biphenyl]-2-yl]-1H-tetrazole;
5-[4'-[[1-butyl-3-(1,1-difluorobutyl)-1H-1,2,4-triazol-5-yl]methyl][1,1'-biphenyl]-2-yl]-1H-tetrazole;
5-[4'-[[1-butyl-3-(1,1-difluoropentyl)-1H-1,2,4-triazol-5-yl]methyl][1,1'-biphenyl]-2-yl]-1H-tetrazole;
5-[4'-[(1,3-dipropyl-1H-1,2,4-triazol-5-yl)methyl][1,1'-biphenyl]-2-yl]-1H-tetrazole;
5-[4'-[(1,3-isopropyl-1H-1,2,4-triazol-5-yl)methyl][1,1'-biphenyl]-2-yl]-1H-tetrazole;
5-[4'-[(1-propyl-3-isopentyl-1H-1,2,4-triazol-5-yl)methyl][1,1'-biphenyl]-2-yl]-1H-tetrazole;
5-[4'-[[1-propyl-3-(1,1-dimethoxybutyl)-1H-1,2,4-triazol-5-yl]methyl][1,1'-biphenyl]-2-yl]-1H-tetrazole;
5-[4'-[[1-propyl-3-(1-oxobutyl)-1H-1,2,4-triazol-5-yl]methyl][1,1'-biphenyl]-2-yl]-1H-tetrazole;
5-[4'-[[1-propyl-3-(1,1-difluoroethyl)-1H-1,2,4-triazol-5-yl]methyl][1,1'-biphenyl]-2-yl]-1H-tetrazole;
5-[4'-[[1-propyl-3-(1,1-difluoropropyl)-1H-1,2,4-triazol-5-yl]methyl][1,1'-biphenyl]-2-yl]-1H-tetrazole;
5-[4'-[[1-propyl-3-(1,1-difluorobutyl)-1H-1,2,4-triazol-5-yl]methyl][1,1'-biphenyl]-2-yl]-1H-tetrazole;
5-[4'-[[1-propyl-3-(1,1-difluoropentyl)-1H-1,2,4-triazol-5-yl]methyl][1,1'-biphenyl]-2-yl]-1H-tetrazole;
5-[4'-[[1-ethyl-3-(1,1-difluorobutyl)-1H-1,2,4-triazol-5-yl]methyl][1,1'-biphenyl]-2-yl]-1H-tetrazole;
5-[4'-[(1-secbutyl-3-propyl-1H-1,2,4-triazol-5-yl)methyl][1,1'-biphenyl]-2-yl]-1H-tetrazole;
5-[4'-[(1-secbutyl-3-butyl-1H-1,2,4-triazol-5-yl)methyl][1,1'-biphenyl]-2-yl]-1H-tetrazole;
5-[4'-[(1,3-disecbutyl-1H-1,2,4-triazol-5-yl)methyl][1,1'-biphenyl]-2-yl]-1H-tetrazole;
5-[4'-[(1-secbutyl-3-isopentyl-1H-1,2,4-triazol-5-yl)methyl][1,1'-biphenyl]-2-yl]-1H-tetrazole;
5-[4'-[[1-secbutyl-3-(1,1-difluoroethyl)-1H-1,2,4-triazol-5-yl]methyl][1,1'-biphenyl]-2-yl]-1H-tetrazole;
5-[4'-[[1-secbutyl-3-(1,1-difluoropropyl)-1H-1,2,4-triazol-5-yl]methyl][1,1'-biphenyl]-2-yl]-1H-tetrazole;
5-[4'-[[1-secbutyl-3-(1,1-difluorobutyl)-1H-1,2,4-triazol-5-yl]methyl][1,1'-biphenyl]-2-yl]-1H-tetrazole;
5-[4'-[[1-secbutyl-3-(1,1-difluoropentyl)-1H-1,2,4-triazol-5-yl]methyl][1,1'-biphenyl]-2-yl]-1H-tetrazole;
5-[4'-[(1-isobutyl-3-propyl-1H-1,2,4-triazol-5-yl)methyl][1,1'-biphenyl]-2-yl]-1H-tetrazole;
5-[4'-[(1-isobutyl-3-butyl-1H-1,2,4-triazol-5-yl)methyl][1,1'-biphenyl]-2-yl]-1H-tetrazole;
5-[4'-[(1,3-diisobutyl-1H-1,2,4-triazol-5-yl)methyl][1,1'-biphenyl]-2-yl]-1H-tetrazole;
5-[4'-[(1-isobutyl-3-isopentyl-1H-1,2,4-triazol-5-yl)methyl][1,1'-biphenyl]-2-yl]-1H-tetrazole;
5-[4'-[[1-isobutyl-3-(1,1-difluoroethyl)-1H-1,2,4-triazol-5-yl]methyl][1,1'-biphenyl]-2-yl]-1H-tetrazole;
5-[4'-[[1-isobutyl-3-(1,1-difluoropropyl)-1H-1,2,4-triazol-5-yl]methyl][1,1'-biphenyl]-2-yl]-1H-tetrazole;
5-[4'-[[1-isobutyl-3-(1,1-difluorobutyl)-1H-1,2,4-triazol-5-yl]methyl][1,1'-biphenyl]-2-yl]-1H-tetrazole;
5-[4'-[[1-isobutyl-3-(1,1-difluoropentyl)-1H-1,2,4-triazol-5-yl]methyl][1,1'-biphenyl]-2-yl]-1H-tetrazole;
5-[4'-[(1-tertbutyl-3-propyl-1H-1,2,4-triazol-5-yl)methyl][1,1'-biphenyl]-2-yl]-1H-tetrazole;
5-[4'-[(1-tertbutyl-3-butyl-1H-1,2,4-triazol-5-yl)methyl][1,1'-biphenyl]-2-yl]-1H-tetrazole;
5-[4'-[(1,3-ditertbutyl-1H-1,2,4-triazol-5-yl)methyl][1,1'-biphenyl]-2-yl]-1H-tetrazole;
5-[4'-[(1-tertbutyl-3-isopentyl-1H-1,2,4-triazol-5-yl)methyl][1,1'-biphenyl]-2-yl]-1H-tetrazole;
5-[4'-[[1-tertbutyl-3-(1,1-difluoroethyl)-1H-1,2,4-triazol-5-yl]methyl][1,1,-biphenyl]-2-yl]-1H-tetrazole;
5-[4'-[[1-tertbutyl-3-(1,1-difluoropropyl)-1H-1,2,4-triazol-5-yl]methyl][1,1'-biphenyl]-2-yl]-1H-tetrazole;
5-[4'-[[1-tertbutyl-3-(1,1-difluorobutyl)-1H-1,2,4-triazol-5-yl]methyl][1,1'-biphenyl]-2-yl]-1H-tetrazole;
5-[4'-[[1-tertbutyl-3-(1,1-difluoropentyl)-1H-1,2,4-triazol-5-yl]methyl][1,1'-biphenyl]-2-yl]-1H-tetrazole;
5-[4'-[(1-pentyl-3-propyl-1H-1,2,4-triazol-5-yl)methyl][1,1'-biphenyl]-2-yl]-1H-tetrazole;
5-[4'-[(1-pentyl-3-butyl-1H-1,2,4-triazol-5-yl)methyl][1,1'-biphenyl]-2-yl]-1H-tetrazole;
5-[4'-[(1,3-dipentyl-1H-1,2,4-triazol-5-yl)methyl][1,1'-biphenyl]-2-yl]-1H-tetrazole;
5-[4'-[(1-pentyl-3-isopentyl-1H-1,2,4-triazol-5-yl)methyl][1,1'-biphenyl]-2-yl]-1H-tetrazole;
5-[4'-[[1-pentyl-3-(1,1-difluoroethyl)-1H-1,2,4-triazol-5-yl]methyl][1,1'-biphenyl]-2-yl]-1H-tetrazole;
5-[4'-[[1-pentyl-3-(1,1-difluoropropyl)-1H-1,2,4-triazol-5-yl]methyl][1,1'-biphenyl]-2-yl]-1H-tetrazole;
5-[4'-[[1-pentyl-3-(1,1-difluorobutyl)-1H-1,2,4-triazol-5-yl]methyl][1,1'-biphenyl]-2-yl]-1H-tetrazole;
5-[4'-[[1-pentyl-3-(1,1-difluoropentyl)-1H-1,2,4-triazol-5-yl]methyl][1,1'-biphenyl]-2-yl]-1H-tetrazole;
5-[4'-[(1-isopentyl-3-ethyl-1H-1,2,4-triazol-5-yl)methyl][1,1'-biphenyl]-2-yl]-1H-tetrazole;
5-[4'-[(1-isopentyl-3-propyl-1H-1,2,4-triazol-5-yl)methyl][1,1'-biphenyl]-2-yl]-1H-tetrazole;
5-[4'-[(1-isopentyl-3-butyl-1H-1,2,4-triazol-5-yl)methyl][1,1'-biphenyl]-2-yl]-1H-tetrazole;
5-[4'-[(1,3-diisopentyl-1H-1,2,4-triazol-5-yl)methyl][1,1'-biphenyl]-2-yl]-1H-tetrazole;

5-[4'-[[1-isopentyl-3-(1,1-difluoroethyl)-1H-1,2,4-triazol-5-yl]methyl][1,1'-biphenyl]-2-yl]-1H-tetrazole;

5-[4'-[[1-isopentyl-3-(1,1-difluoropropyl)-1H-1,2,4-triazol-5-yl]methyl][1,1'-biphenyl]-2-yl]-1H-tetrazole;

5-[4'-[[1-isopentyl-3-(1,1-difluorobutyl)-1H-1,2,4-triazol-5-yl]methyl][1,1'-biphenyl]-2-yl]-1H-tetrazole;

5-[4'-[[1-isopentyl-3-(1,1-difluoropentyl)-1H-1,2,4-triazol-5-yl]methyl][1,1'-biphenyl]-2-yl]-1H-tetrazole;

5-[4'-[[1-(2-butenyl)-3-(1,1-difluorobutyl)-1H-1,2,4-triazol-5-yl]methyl][1,1'-biphenyl]-2-yl]-1H-tetrazole;

5-[4'-[[1-(3-butenyl)-3-(1,1-difluorobutyl)-1H-1,2,4-triazol-5-yl]methyl][1,1'-biphenyl]-2-yl]-1H-tetrazole;

5-[4'-[[1-(2-butynyl)-3-(1,1-difluorobutyl)-1H-1,2,4-triazol-5-yl]methyl][1,1'-biphenyl]-2-yl]-1H-tetrazole;

5-[4'-[[1-(3-butynyl)-3-(1,1-difluorobutyl)-1H-1,2,4-triazol-5-yl]methyl][1,1'-biphenyl]-2-yl]-1H-tetrazole;

5-[4'-[[1,3-di(2-butenyl)-1H-1,2,4-triazol-5-yl]methyl][1,1'-biphenyl]-2-yl]-1H-tetrazole;

5-[4'-[[1,3-di(3-butenyl)-1H-1,2,4-triazol-5-yl]methyl][1,1'-biphenyl]-2-yl]-1H-tetrazole;

5-[4'-[[1,3-di(2-butynyl)-1H-1,2,4-triazol-5-yl]methyl][1,1'-biphenyl]-2-yl]-1H-tetrazole; and 5-[4'-[[1,3-di(3-butynyl)-1H-1,2,4-triazol-5-yl]methyl][1,1'-biphenyl]-2-yl]-1H-tetrazole.

4. The method of claim 3 wherein said compound is 4'[1,3-dibutyl-1H-1,2,4-triazol-5-yl)methyl][1,1'-biphenyl]-2-carboxylic acid or a pharmaceutically-acceptable salt thereof.

5. The method of claim 3 wherein said compound is 5-[4'-[(1,3-dibutyl-1H-1,2,4-triazol-5-yl)methyl][1,1'-biphenyl]-2-yl]-1H-tetrazole or a pharmaceutically-acceptable salt thereof.

* * * * *